United States Patent
Zhao et al.

(10) Patent No.: US 10,908,169 B2
(45) Date of Patent: *Feb. 2, 2021

(54) REAGENTS AND METHODS FOR DETECTING PROTEIN CROTONYLATION

(71) Applicant: PTM BIO LLC, Chicago, IL (US)

(72) Inventors: Yingming Zhao, Chicago, IL (US); Jeong Soo Yang, Seoul (KR); Hao Luo, Chicago, IL (US); Zhongyi Cheng, Hangzhou (CN)

(73) Assignee: PTM BIO LLC, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/249,363

(22) Filed: Jan. 16, 2019

(65) Prior Publication Data

US 2019/0137512 A1 May 9, 2019

Related U.S. Application Data

(60) Division of application No. 14/531,282, filed on Nov. 3, 2014, now abandoned, which is a continuation of application No. 13/728,024, filed on Dec. 27, 2012, now abandoned, and a continuation-in-part of application No. 13/117,154, filed on May 27, 2011, now Pat. No. 9,625,467.

(60) Provisional application No. 61/580,468, filed on Dec. 27, 2011, provisional application No. 61/349,185, filed on May 27, 2010.

(51) Int. Cl.
| | |
|---|---|
| G01N 33/68 | (2006.01) |
| C07K 7/06 | (2006.01) |
| C07K 7/08 | (2006.01) |
| C12N 15/10 | (2006.01) |
| C07K 16/44 | (2006.01) |

(52) U.S. Cl.
CPC .......... *G01N 33/6875* (2013.01); *C07K 7/06* (2013.01); *C07K 7/08* (2013.01); *C07K 16/44* (2013.01); *C12N 15/1037* (2013.01); *G01N 33/6803* (2013.01); *G01N 33/6842* (2013.01); *G01N 2440/10* (2013.01)

(58) Field of Classification Search
None
See application file for complete search history.

(56) References Cited

U.S. PATENT DOCUMENTS

| | | | |
|---|---|---|---|
| 6,958,212 B1 | 10/2005 | Hubbel et al. | |
| 7,485,416 B2 | 2/2009 | Ott et al. | |
| 7,744,912 B1 | 6/2010 | Hubbel et al. | |
| 9,012,166 B2 | 4/2015 | Nishino et al. | |
| 2012/0135538 A1 | 5/2012 | Zhao | |

FOREIGN PATENT DOCUMENTS

| | | |
|---|---|---|
| EP | 2562264 A1 | 2/2013 |
| WO | 03070894 A2 | 8/2003 |
| WO | 2011132392 A1 | 10/2011 |

OTHER PUBLICATIONS

Flynn et al., A Subset of Human Bromodomains Recognizes Butyryllysine and Crotonyllysine Histone Peptide Modifications, Structure, 23, 10, 2015, 1801-1814 (Year: 2015).*
Bonenfant et al., "Characterization of Histone H2A and H2B Variants and Their Post-translational Modifications by Mass Spectrometry", Molecular & Cellular Proteomics, 5.3, 2006, pp. 541-552.
Boyne et al., "Precise Characterization of Human Histones in the H2A Gene Family by Top Down Mass Spectrometry", Journal of Proteome Research, 2006, vol. 5, pp. 248-253.
Chen et al., "Integrated Approach for Manual Evaluation of Peptides Identified by Searching Protein Sequence Databases with Tandem Mass Spectra", Journal of Proteome Research, 2005, vol. 4, pp. 998-1005.
Chen et al., "PTMap—A Sequence Alignment Software for Unrestricted, Accurate, and Full-spectrum Identification of Post-translational Modification Sites", Proc. Natl. Acad. Sci. USA, vol. 106, 2009, pp. 761-766.
Chu et al., "Mapping Post-translational Modifications of the Histone Variant MacroH2A1 using Tandem Mass Spectrometry", Molecular & Cellular Proteomics, 5.1, vol. 5, 2006, pp. 194-203.
Cosgrove et al., "Regulated Nucleosome Mobility and the Histone Code", Nature Structural & Molecular Biology, vol. 11, No. 11, 2004, pp. 1037-1043.
European Search Report for European Application No. 12 19 9554, dated Mar. 18, 2013, 2 pages.
Garcia et al., "Characterization of Histones and their Post-translational Modifications by Mass Spectrometry", Current Opinion in Chemical Biology, 2007, vol. 11, pp. 66-73.
Garcia et al., "Chemical Derivatization of Histones for Facilitated Analysis by Mass Spectrometry", Nature Protocols, vol. 2, No. 4, 2007, pp. 933-938.
Garcia et al., "Pervasive Combinatorial Modification of Histone H3 in Human Cells", Nature Methods, vol. 4, No. 6, 2007, pp. 487-489.
Gattner et al., Supplemental Information, "Synthesis of ε-N-propionyl-, ε-N-butyryl-, and ε-N-crotonyl-lysine Containing Histone H3 using the Pyrrolysine System", retrieved from http://rsc.org/suppdata/cc/c2/c2cc37836a/c2cc37836a.pdf on Feb. 6, 2017, 30 pages.
Gattner et al., "Synthesis of ε-N-propionyl-, ε-N-butyryl-, and ε-N-crotonyl-lysine Containing Histone H3 using the Pyrrolysine System", Chem. Commun., 2013, 49, pp. 379-381.

(Continued)

*Primary Examiner* — Andrea S Grossman
(74) *Attorney, Agent, or Firm* — RatnerPrestia

(57) ABSTRACT

The invention provides an isolated peptide comprising a crotonylation site, a Kcr-specific affinity reagent that specifically binds to the peptide, and a method for detecting protein crotonylation in a sample using the reagent.

9 Claims, 21 Drawing Sheets

Specification includes a Sequence Listing.

(56) References Cited

OTHER PUBLICATIONS

Jenuwein et al., "Translating the Histone Code", Science, vol. 293, 2001, pp. 1074-1080.
Johnson et al., "Mass Spectrometry Analysis of *Arabidopsis* Histone H3 Reveals Distinct Combinations of Post-transitional Modifications", Nucleic Acids Research, 2004, vol. 32, No. 22, pp. 6511-6518.
Kehoe et al., "Using Phage Display to Select Antibodies Recognizing Post-translational Modifications Independently of Sequence Context", Molecular & Cellular Proteomics, 5.12, pp. 2350-2363.
Kim et al., "Substrate and Functional Diversity of Lysine Acetylation Revealed by a Proteomics Survey", Molecular Cell, 23, Aug. 18, 2006, pp. 607-618.
Kouzarides, T., "Chromatin Modifications and Their Function", Cell, vol. 128, Feb. 23, 2007, pp. 693-705.
Liu et al., "Specific Post-transitional Histone Modifications of Neutrophil extracellular Traps as Immunogens and Potential Targets of Lupus Autoantibodies", Arthritis Research & Therapy, 2012, 14:R25, pp. 1-14.
Luo et al., "Regulation of Intra-S Phase Checkpoint by Ionizing Radiation (IR)-dependent and IR-independent Phosphorylation of SMC3", Journal of Biological Chemistry, vol. 283, No. 28, Jul. 11, 2018, pp. 19176-19183.
Margueron et al., "The Key to Development: Interpreting the Histone Code?", Current Opinion in Genetics & Development, 2005, vol. 15, pp. 163-176.
Martin et al., "Mechanisms of Epigenetic Inheritance", Current Opinion in Genetics & Development, 2007, vol. 19, pp. 266-272.
Medzihradszky et al., "Characterization of Tetrahymena Histone H2B variants and Posttranslational Populations by Electron Capture Dissociation (ECD) Fourier Transform Ion Cyclotron Mass Spectrometry (FT-ICR MS)", Molecular & Cellular Proteomics, 3.9, pp. 872-886.
Mersfelder et al., "The Tale Beyond the Tail: Histone Core Domain Modifications and the Regulation of Chromatin Structure", Nucleic Acids Research, 2006, vol. 34, No. 9, pp. 2653-2662.
Montellier et al., "Histone Crotonylation Specifically Marks the Haploid Male Germ Cell Gene Expression Program", Bioessays, vol. 34, 2011, pp. 187-193.
PTM Biolabs, Pan Anti-butyryllysine Antibody, https://www.ptmbiolabs.com/product/ptm301/, retrieved on Feb. 6, 2017, 7 pages.
Ruthenburg et al., "Multivalent Engagement of Chromatin Modifications by Linked Binding Modules", Nature Reviews, Molecular Cell Biology, vol. 8, Dec. 2007, pp. 983-994.
Sakabe et al., "Beta-N-acetylglucosamine (O-GlcNAc) is Part of the Histone Code", PNAS, vol. 107, No. 46, Nov. 16, 2010, pp. 19915-19920.
Shechter et al., "Extraction, Purification and Analysis of Histones", Nature Protocols, vol. 2, No. 6, 2007, p. 1445-1457.
Siuti et al., "Gene-Specific Characterization of Human Histone H2B by Electron Capture Dissociation", Journal of Proteome Research, 2006, vol. 5, pp. 233-239.
Tan et al., "Identification of 67 Histone Marks and Histone Lysine Crotonylation as a New Type of Histone Modification", Cell 146, Sep. 16, 2011, pp. 1016-1028.
Tateishi et al., "Role of Jhdm2a in Regulating Metabolic Gene Expression and Obesity Resistance", Nature, vol. 458, Apr. 2009, pp. 757-761.
Venter et al., "The Sequence of the Human Genome", Science, vol. 291, Feb. 16, 2001, pp. 1304-1352.
Wisniewski et al., "Mass Spectrometric Mapping of Linker Histone H1 Variants Reveals Multiple Acetylations, Methylations, and Phosphorylation as Well as Differences Between Cell Culture and Tissue", Molecular & Cellular Proteomics 6.1, 2007, pp. 72-87.
Wysocka et al., "A PHD Finger of NURF Couples Histone H3 Lysine 4 Trimethylation with Chromatin Remodelling", Nature, vol. 442, Jul. 6, 2006, pp. 86-90.
Wysocka et al., "WDR5 Associates with Histone H3 Methylated at K4 and is Essential for H3 K4 Methylation and Vertebrate Development", Cell, vol. 121, Jun. 17, 2005, pp. 859-872.
Zee et al., "In Vivo Residue—specific Histone Methylation Dynamics", Journal of Biological Chemistry, vol. 285, No. 5, Jan. 29, 2010, pp. 3341-3350.
Zeng et al., "Bromodomain: An Acetyl-lysine Binding Domain", FEBS Letters, vol. 513, 2002, pp. 124-128.
Zhang et al., "Identification and Verification of Lysine Propionylation and Butyrylation in Yeast Core Histones using PTMap Software", Journal of Proteome Research, 2009, vol. 8, pp. 900-906.
Zhang et al., "MS/MS/MS Reveals False Positive Identification of Histone Serine Methylation", Journal of Proteome Research, Jan. 2010, 9(1), pp. 585-594.
Bao et al., "Identification of 'Erasers' for Lysine Crotonylated Histone Marks Using a Chemical Proteomics Approach", ELife, 2014, vol. 3, pp. 1-18.

\* cited by examiner

FIG. 1
A.
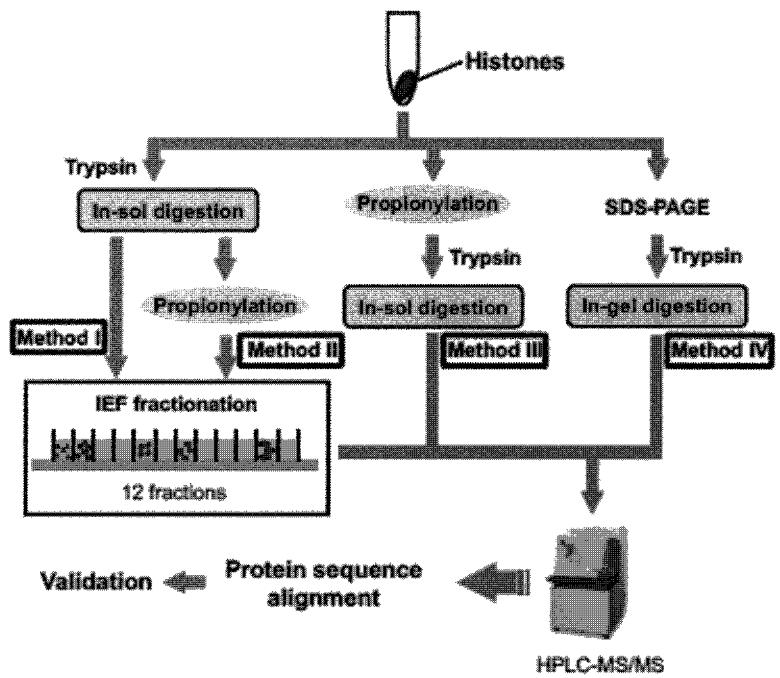
B.
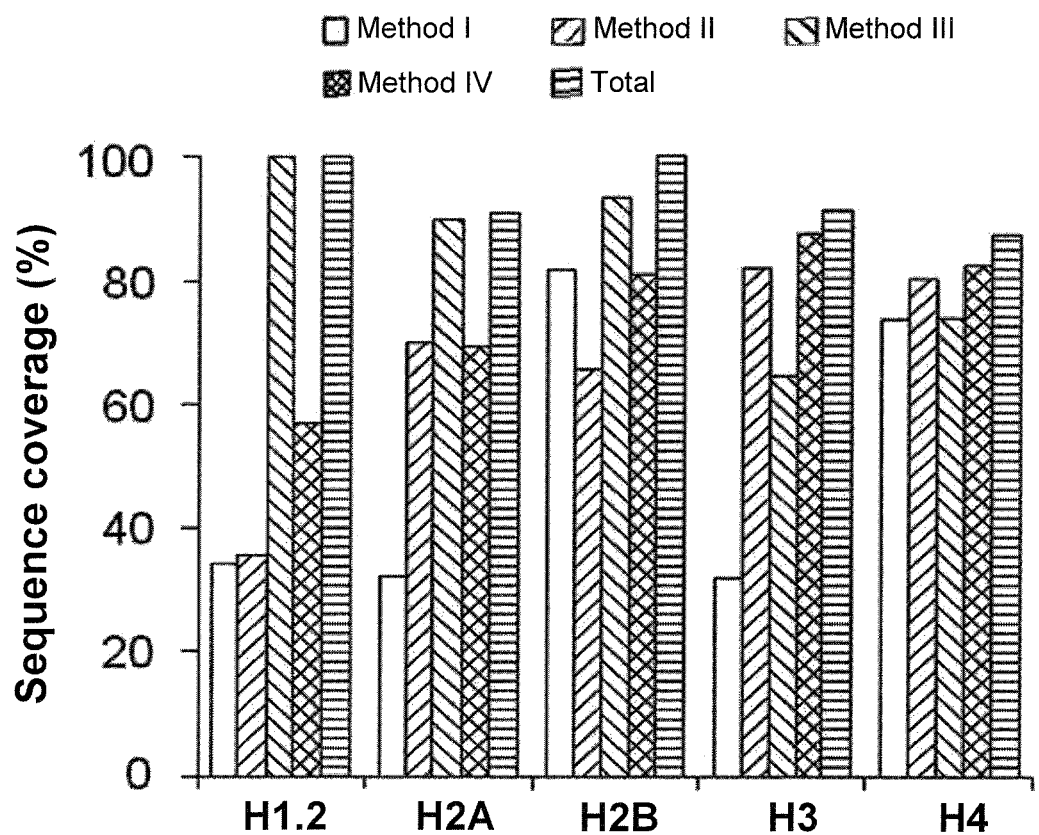

| PTMs | Linker histone | Core histones | | | | Total |
|---|---|---|---|---|---|---|
| | H1.2 | H2A | H2B | H3 | H4 | |
| # of identified sites | 31 | 12 | 31 | 33 | 23 | 130 |
| # of novel sites | 17 | 10 | 19 | 10 | 11 | 67 |
| Kme | 7 | 3 | 6 | - | 2 | 18 |
| Kme2 | - | - | - | - | 1 | 1 |
| Kfo | 1 | - | 2 | 1 | - | 4 |
| Kac | 1 | - | - | 1 | - | 2 |
| Rme | - | 2 | 1 | 2 | 3 | 8 |
| Yoh | 1 | 1 | 2 | - | 2 | 6 |
| Kcr | 7 | 4 | 8 | 6 | 3 | 28 |

D.

H1.2 (SEQ ID NO: 1); H2A (SEQ ID NO: 2); H2B (SEQ ID NO: 3); H3 (SEQ ID NO: 4); H4 (SEQ ID NO: 5).

Kcr: lysine crotonylation    Kac: lysine acetylation

```
            Mouse:                                      Kcr           Kcr
            Human:                                      Kcr           KcrKcr      Kcr
H2A Human:  NH₂-SGRGKQGGKARAKAKTR.........LLRKGNY.........AVLLPKKTESHHKAKGK-COOH
                    5   9   13 15              36                118 119    125
                    Kac Kac Kac Kac            Kac Mouse:          Kcr      KcrKcr KcrKcr  Kcr Kcr        Kcr
            Human:          Kcr      KcrKcr KcrKcr  Kcr Kcr        Kcr
H2B Human:  NH₂-PEPAKSAPAPKKGSKKAVTKAQKK.........RSRKESYSI.........TKYTSSK-COOH
                    5       11 12   15 16    20  23 24           34
                    Kac     Kac     Kac         Kac   Kac Mouse:        Kcr     Kcr           Kcr   Kcr Kcr    Kcr
            Human:        Kcr     Kcr           Kcr   Kcr Kcr    Kcr
H3 Human:   NH₂-ARTKQTARKSTGGKAPRKQLATKAARKS.........RYQKST...RIRGERA-COOH
                    4       9       14  18    23  27       56
                    Kac     Kac     Kac Kac   Kac Kac      Kac Mouse:         Kcr Kcr     Kcr
            Human:         Kcr Kcr     Kcr
H4 Human:   NH₂-SGRGKGGKGLGKGGAKRHRKVLRDNIQG.........TLYGFGG-COOH
                    5   8   12  16    20
                    Kac Kac Kac Kac   Kac Mouse:            Kcr       Kcr    Kcr              Kcr     Kcr
            Human:            Kcr       Kcr    Kcr     Kcr      Kcr     Kcr
H1.2 Human: NH₂-SET...PRKASGP...ALKKAL...GLKSLVSKGTLVQTKG......KAKK...ATVTKKVA.........KK-COOH
                     33         63       84      89          96      158     167
```

FIG. 2
A.
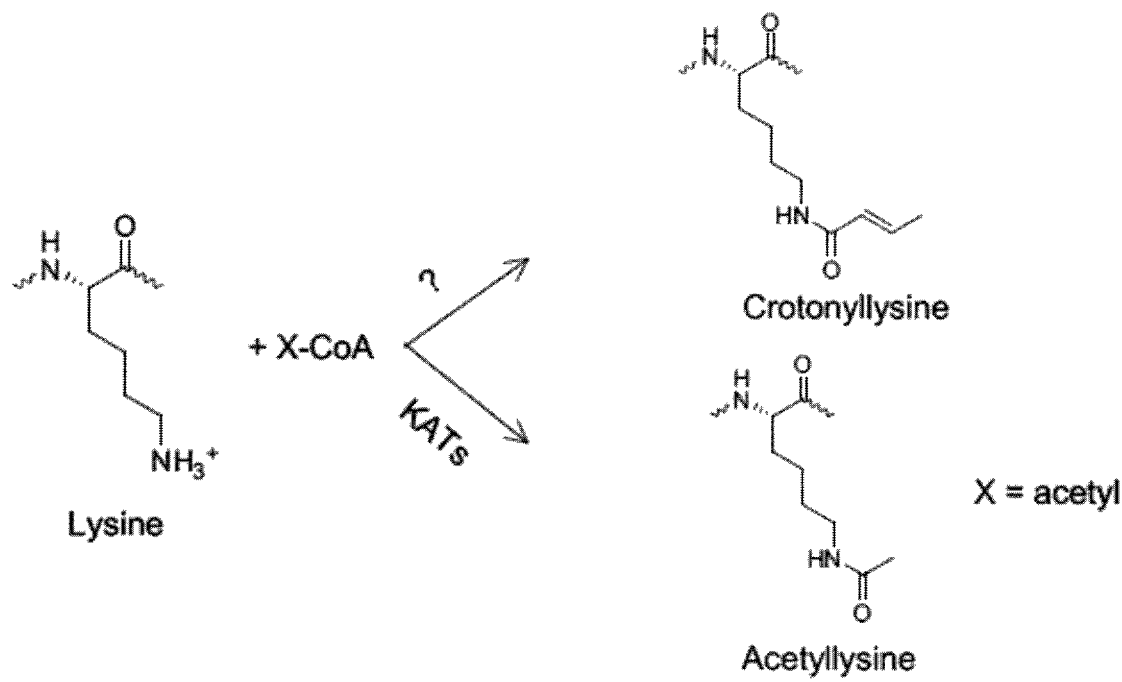
B.
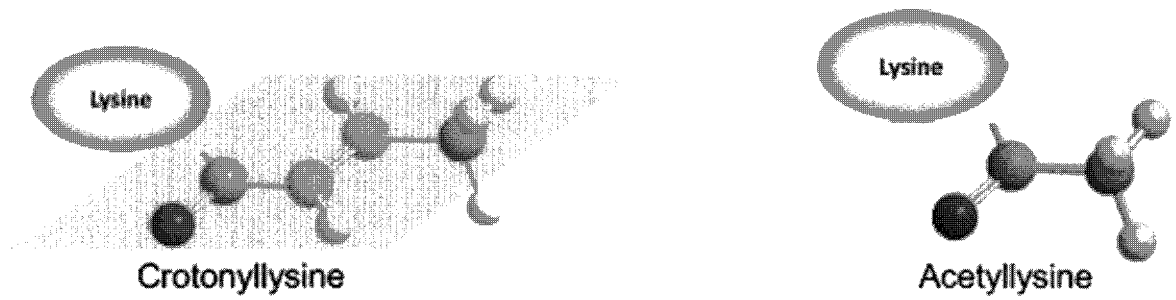

FIG. 2
C.
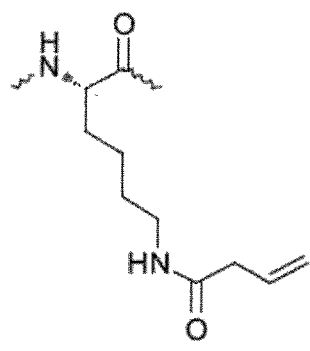
Vinylacetyllysine
(But-3-enoyllysine)
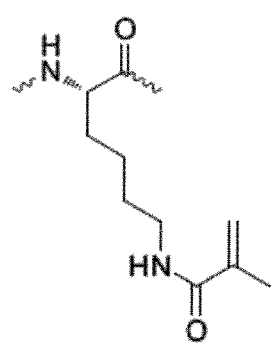
Methacryllysine
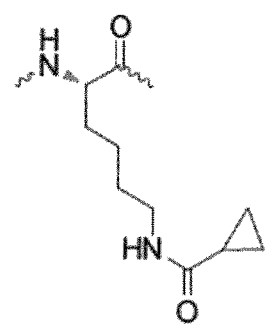
cyclopropanecarboxyllysine
D.
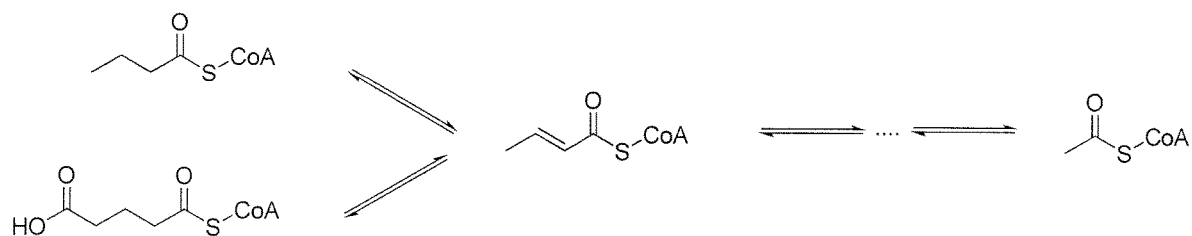

FIG. 3
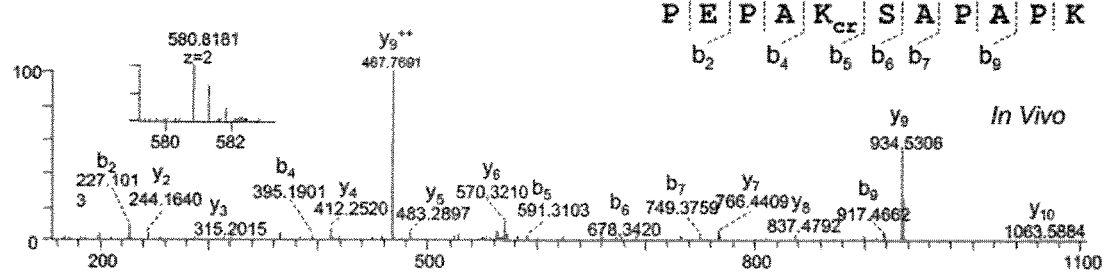
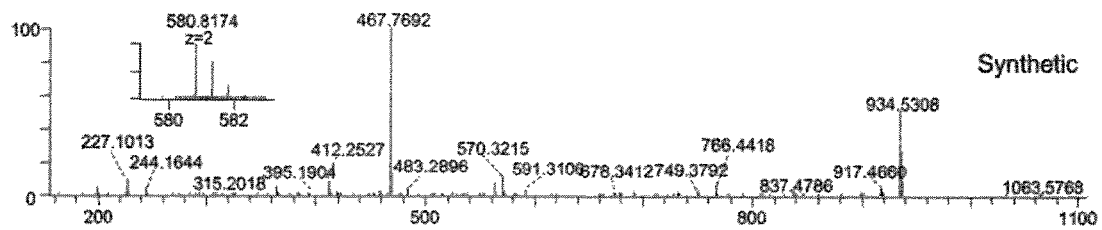
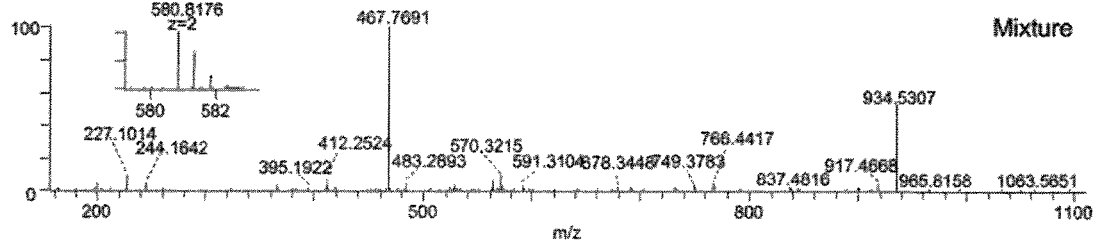
PEPAKcrSAPAPK (SEQ ID NO: 44).

D.

FIG. 4
A.
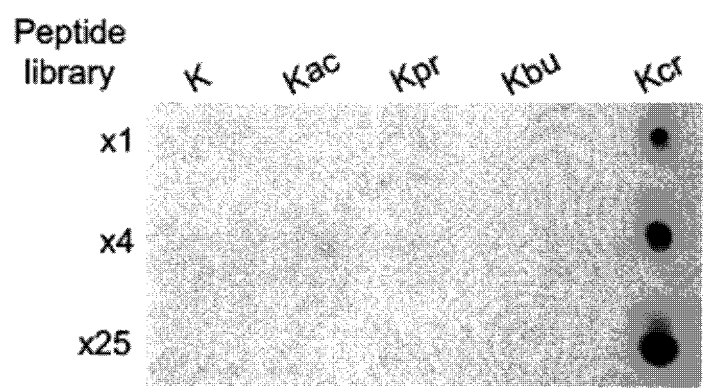
B.
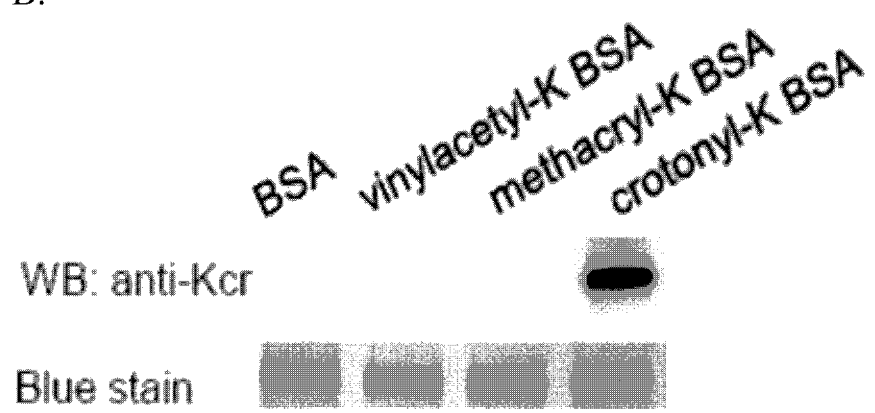

FIG. 4
C.
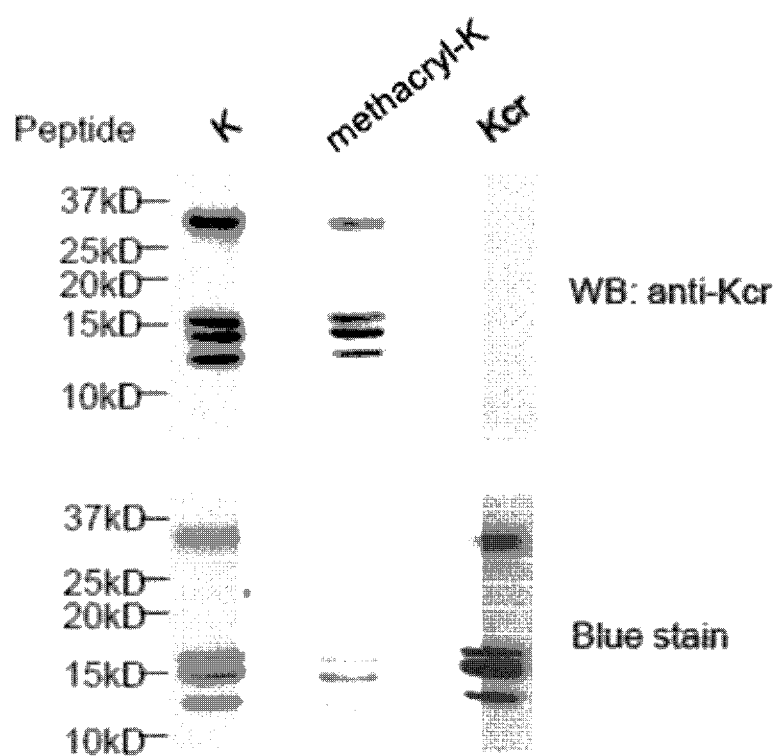
D.
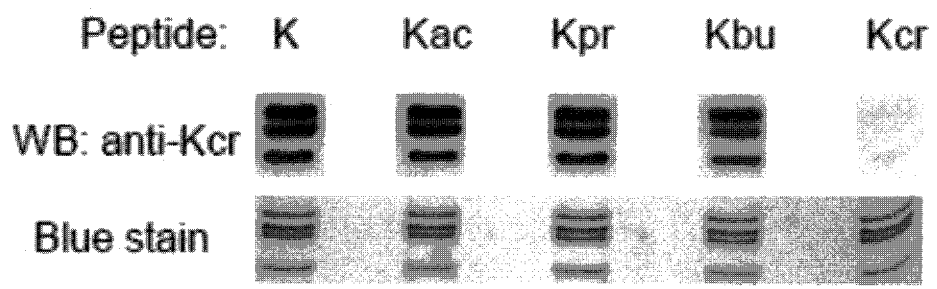

A.

B.

PEPAK$_{D4-cr}$SAPAPK (SEQ ID NO: 44)

FIG. 9

A. P16403 (H12_HUMAN) (SEQ ID NO: 1)

MSETAPAAPAAAPPAEKAPVKKKAAKKAGGTPRKASGPPVSELITKAVAASKERSGVSL
AALKKALAAAGYDVEKNNSRIKLGLKSLVSKGTLVQTKGTGASGSFKLNKKAASGEAK
PKVKKAGGTKPKKPVGAAKKPKKAAGGATPKKSAKKTPKKAKKPAAATVTKKVAKSP
KKAKVAKPKKAAKSAAKAVKPKAAKPKVVKPKKAAPKKK

B. P04908 (H2A1B_HUMAN) (SEQ ID NO: 2)

MSGRGKQGGKARAKAKTRSSRAGLQFPVGRVHRLLRKGNYSERVGAGAPVYLAAVLE
YLTAEILELAGNAARDNKKTRIIPRHLQLAIRNDEELNKLLGRVTIAQGGVLPNIQAVLLP
KKTESHHKAKGK

C. P33778 (H2B1B_HUMAN) (SEQ ID NO: 3)

MPEPSKSAPAPKKGSKKAITKAQKKDGKKRKRSRKESYSIYVYKVLKQVHPDTGISSKA
MGIMNSFVNDIFERIAGEASRLAHYNKRSTITSREIQTAVRLLLPGELAKHAVSEGTKAV
TKYTSSK

D. P84243 (H33_HUMAN) (SEQ ID NO: 4)

MARTKQTARKSTGGKAPRKQLATKAARKSAPSTGGVKKPHRYRPGTVALREIRRYQKS
TELLIRKLPFQRLVREIAQDFKTDLRFQSAAIGALQEASEAYLVGLFEDTNLCAIHAKRVT
IMPKDIQLARRIRGERA

E. P62805 (H4_HUMAN) (SEQ ID NO: 5)

MSGRGKGGKGLGKGGAKRHRKVLRDNIQGITKPAIRRLARRGGVKRISGLIYEETRGVL
KVFLENVIRDAVTYTEHAKRKTVTAMDVVYALKRQGRTLYGFGG

FIG. 10

A. P15864 (H12_MOUSE) (SEQ ID NO: 6)

MSEAAPAAPAAAPPAEKAPAKKKAAKKPAGVRRKASGPPVSELITKAVAASKERSGVS
LAALKKALAAAGYDVEKNNSRIKLGLKSLVSKGILVQTKGTGASGSFKLNKKAASGEA
KPQAKKAGAAKAKKPAGAAKKPKKATGAATPKKAAKKTPKKAKKPAAAAVTKKVAK
SPKKAKVTKPKKVKSASKAVKPKAAKPKVAKAKKVAAKKK

B. P22752 (H2A1_MOUSE) (SEQ ID NO: 7)

MSGRGKQGGKARAKAKTRSSRAGLQFPVGRVHRLLRKGNYSERVGAGAPVYLAAVLE
YLTAEILELAGNAARDNKKTRIIPRHLQLAIRNDEELNKLLGRVTIAQGGVLPNIQAVLLP
KKTESHHKAKGK

C. Q64475 (H2B1B_MOUSE) (SEQ ID NO: 8)

MPEPSKSAPAPKKGSKKAISKAQKKDGKKRKRSRKESYSVYVYKVLKQVHPDTGISSK
AMGIMNSFVNDIFERIASEASRLAHYNKRSTITSREIQTAVRLLLPGELAKHAVSEGTKA
VTKYTSSK

D. P84244 (H33_MOUSE) (SEQ ID NO: 9)

MARTKQTARKSTGGKAPRKQLATKAARKSAPSTGGVKKPHRYRPGTVALREIRRYQKS
TELLIRKLPFQRLVREIAQDFKTDLRFQSAAIGALQEASEAYLVGLFEDTNLCAIHAKRVT
IMPKDIQLARRIRGERA

E. P62806 (H4_MOUSE) (SEQ ID NO: 10)

MSGRGKGGKGLGKGGAKRHRKVLRDNIQGITKPAIRRLARRGGVKRISGLIYEETRGVL
KVFLENVIRDAVTYTEHAKRKTVTAMDVVYALKRQGRTLYGFGG

FIG. 11
A.
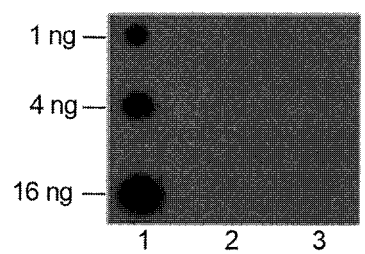
B.
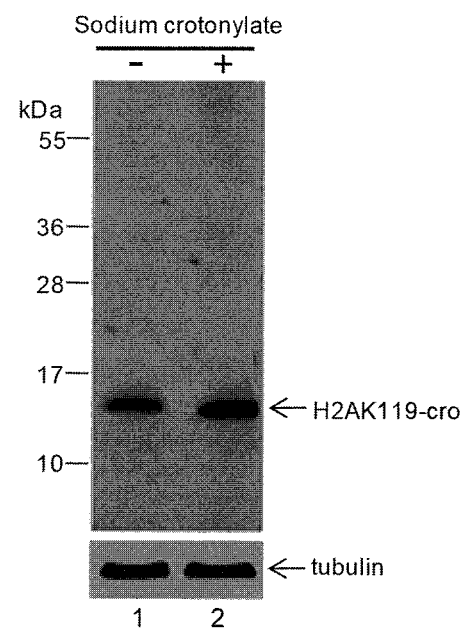
FIG. 12
A.
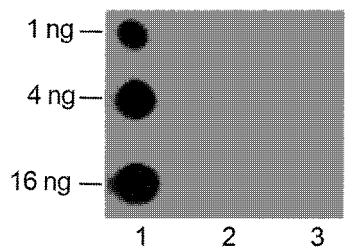
B.
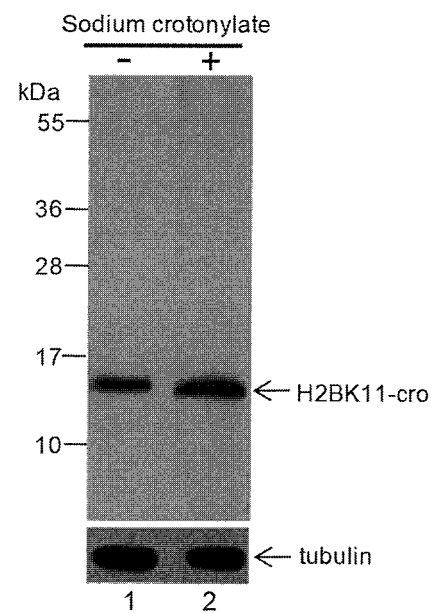

FIG. 13
A.
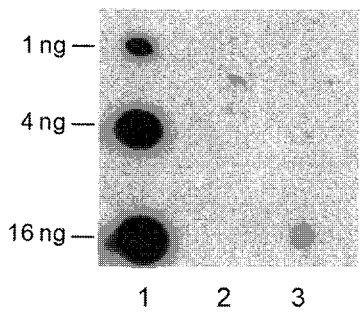
B.
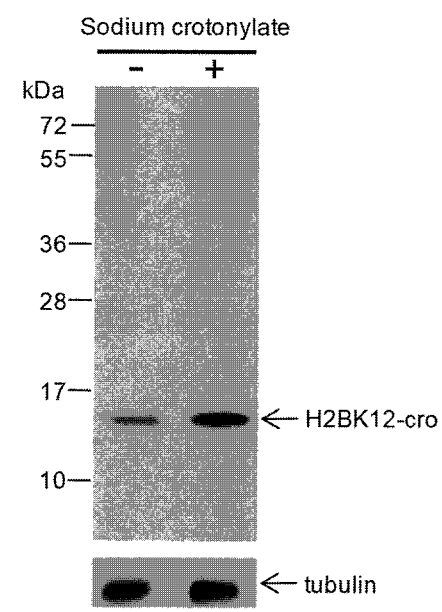
FIG. 14
A.
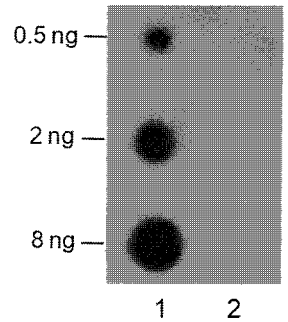
B.
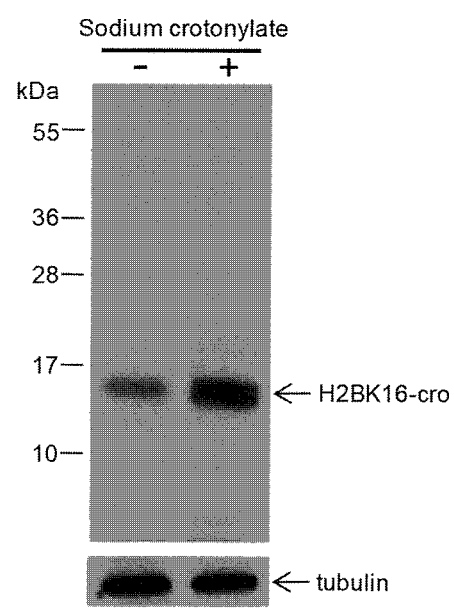

FIG. 15
A.
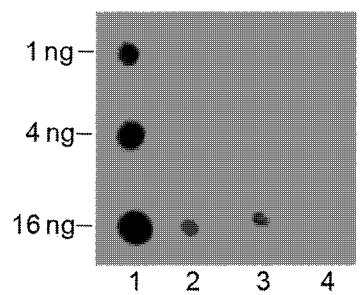
B.
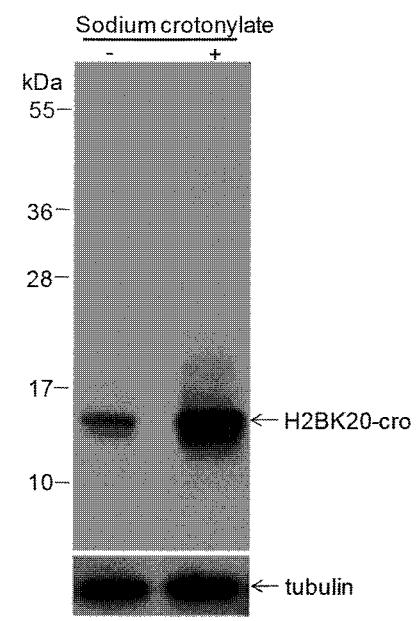
FIG. 16
A.
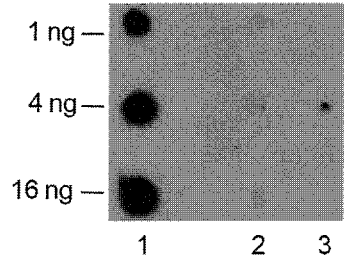
B.
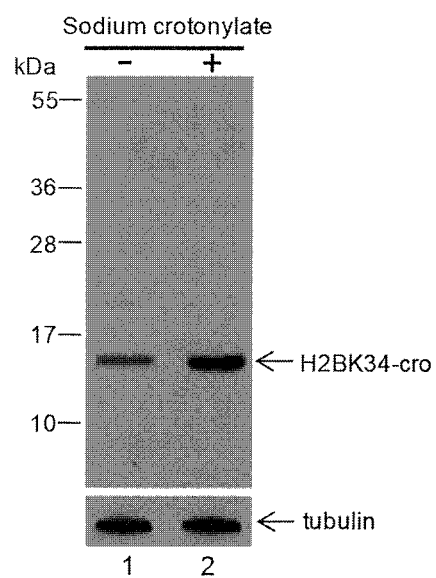

FIG. 17
A.
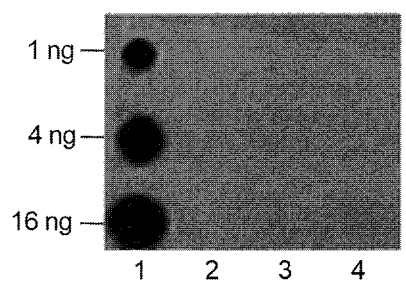
B.
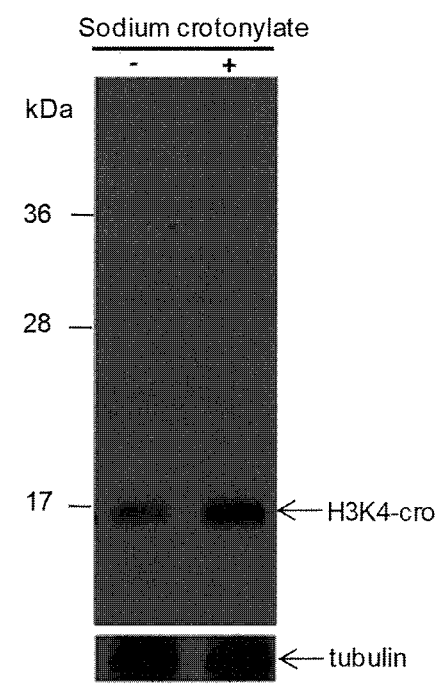
FIG. 18
A.
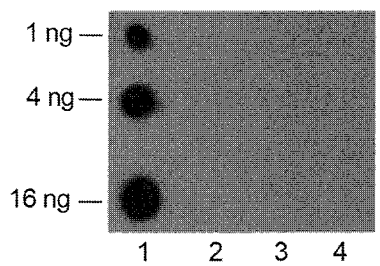
B.
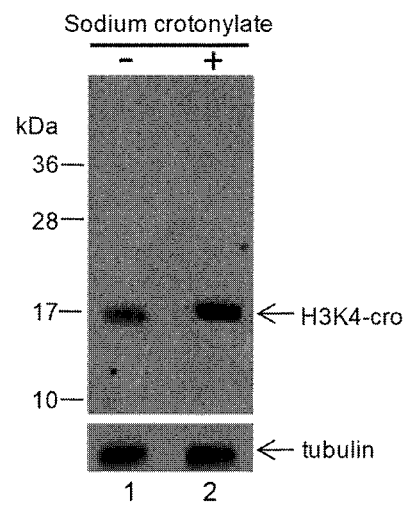

FIG. 19
A.
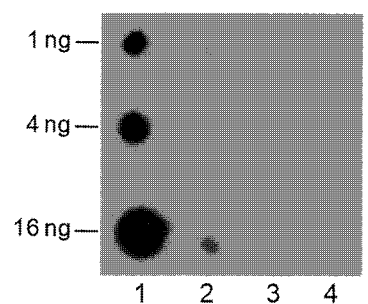
B.
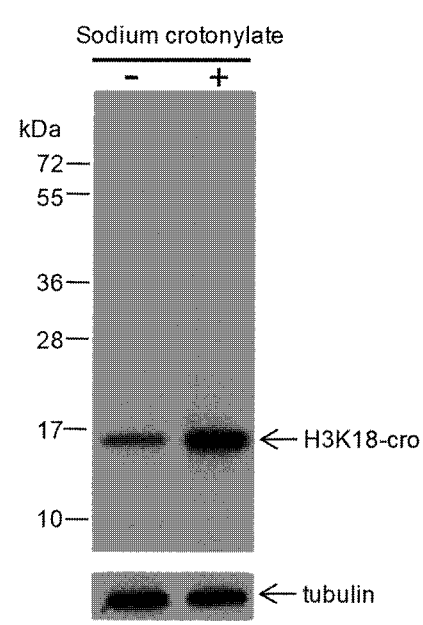
FIG. 20
A.
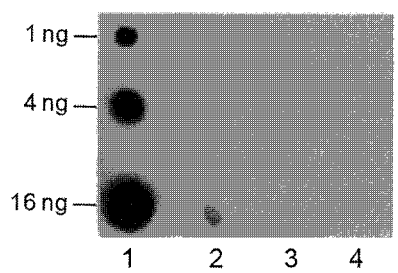
B.
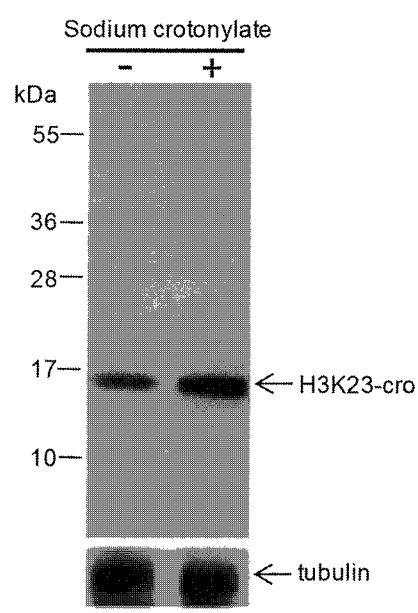

FIG. 21
A.
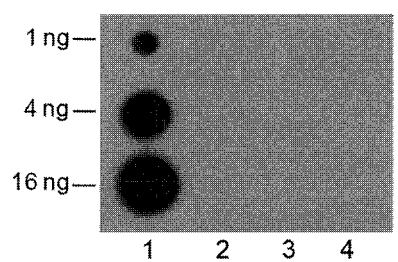
B.
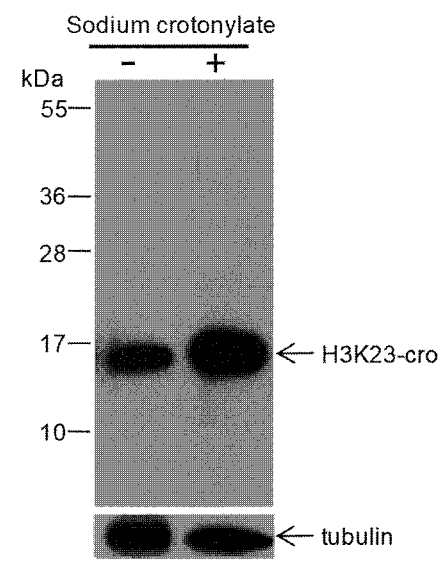
FIG. 22
A.
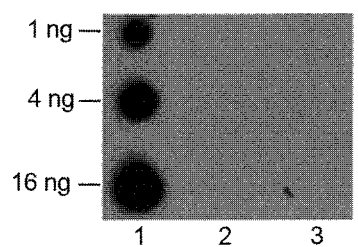
B.
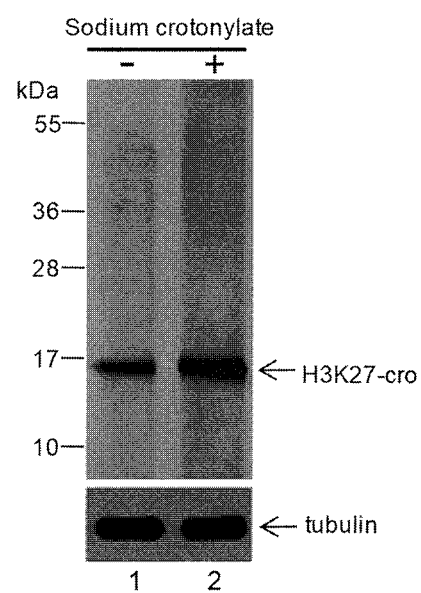

REAGENTS AND METHODS FOR DETECTING PROTEIN CROTONYLATION

CROSS-REFERENCE TO RELATED APPLICATIONS

This application is a divisional application of U.S. application Ser. No. 14/531,282 filed on Nov. 3, 2014, which claims the benefit of U.S. application Ser. No. 13/728,024 filed on Dec. 27, 2012, which claims the benefit of U.S. Provisional Application No. 61/580,468, filed on Dec. 27, 2011, and is a continuation-in-part of U.S. application Ser. No. 13/117,154, filed May 27, 2011, which issued on Apr. 18, 2017 as U.S. Pat. No. 9,625,467, which claims priority to U.S. Provisional Application No. 61/349,185, filed May 27, 2010, and the contents of each of which are incorporated by reference herein, in their entireties and for all purposes.

FIELD OF THE INVENTION

This invention relates to reagents and methods for detecting protein crotonylation. More particularly, it relates to peptides comprising a crotonylation site, and their uses to develop reagents and methods useful for detecting crotonylation in proteins.

BACKGROUND OF THE INVENTION

Molecular anatomy of post-translational modifications that regulate cellular processes and disease progression stands as one of the major goals of post-genomic biological research. To date, more than 300 post-translational modifications have been described, which provide an efficient way to diversify a protein's primary structure and possibly its functions. The remarkable complexity of these molecular networks is exemplified by modifications at the side chain of lysine, one of the fifteen ribosomally-coded amino acid residues known to be modified. The electron-rich and nucleophilic nature of the lysine side chain makes it suitable for undergoing covalent post-translational modification reactions with diverse substrates that are electrophilic. The residue can be potentially modulated by several post-translational modifications including methylation, acetylation, biotinylation, ubiquitination, and sumoylation, which have pivotal roles in cell physiology and pathology.

Histones, for example, are known to be modified by an array of post-translational modifications, including methylation, acetylation, ubiquitination, small ubiquitin-like modification, and ribosylation. A combinatorial array of post-translational modifications in histones, termed the "histone code", dictates the proteins' functions in gene expression and chromatin dynamics. Post-translational modifications of histones have been studied by both biochemistry (Jenuwein, et al. 2001) and mass spectrometry (Garcia, et al. 2007; Boyne, et al. 2006; Medzihradszky, et al. 2004).

Histone is acetylated at lysine residues. Lysine acetylation is an abundant, reversible, and highly regulated post-translational modification. It is generally highly correlated with gene activity. While initially discovered in histones, the modification was later identified in non-histone proteins, such as p53. A recent proteomics screening showed that acetyllysine is abundant and present in substrates that are affiliated with multiple organelles and have diverse functions. Interestingly, the modification is enriched in mitochondrial proteins and metabolic enzymes, implying its roles in fine-tuning the organelle's functions and energy metabolism. The modification plays an important role in diverse cellular processes, such as apoptosis, metabolism, transcription, and stress response. In addition to their roles in fundamental biology, lysine acetylation and its regulatory enzymes (acetyltransferases and deacetylases) are intimately linked to aging and several major diseases such as cancer, neurodegenerative disorders, and cardiovascular diseases.

There remains a need for developing reagents and methods useful for detecting post-translational modifications of histones or nonhistone proteins linked to various diseases and disorders.

SUMMARY OF THE INVENTION

The present invention relates to the use of peptides comprising a crotonylation site to develop reagents and methods for detecting protein crotonylation, especially site specific crotonylation.

An isolated peptide comprising a crotonylation site is provided. The peptide may be derived from a histone protein or a fragment thereof. The peptide may comprise a sequence selected from SEQ ID NOs: 11-43.

The peptide may be crotonylated at a lysine site, which is also called crotonyllysine residue. Examples of the crotonylated peptides include QLATKcrAA (SEQ ID NO: 11), CQLATKcrAA (SEQ ID NO: 12), YQKcrST (SEQ ID NO: 13), CYQKcrSTELL (SEQ ID NO: 14), LLPKKcrTESHHKAK (SEQ ID NO: 15), CLLPKKcrTESHHKAKG (SEQ ID NO: 16), APAPKcrKGS (SEQ ID NO: 17), APAPKcrKGSC (SEQ ID NO: 18), APAPKKcrGS (SEQ ID NO: 17), CAPAPKKcrGS (SEQ ID NO: 19), GSKKcrA (SEQ ID NO: 20), GSKKcrAVTC (SEQ ID NO: 21), TKcrAQKKDG (SEQ ID NO: 22), AVTKcrAQKKDGC (SEQ ID NO: 23), ARTKcrQTAR (SEQ ID NO: 24), ARTKcrQTARC (SEQ ID NO: 25), APRKcrQLA (SEQ ID NO: 26), APRKcrQLATC (SEQ ID NO: 27), QLATKcrAARK (SEQ ID NO: 28), QLATKcrAARKC (SEQ ID NO: 29), AARKcrSAP (SEQ ID NO: 30), AARKcrSAPATGGC (SEQ ID NO: 31), CRLLRKcrGNYAER (SEQ ID NO: 32), CLLPKcrKTESHHKAKG (SEQ ID NO: 16), CLLPKKTESHHKcrAKG (SEQ ID NO: 16), CAVTKAQKcrKDG (SEQ ID NO: 33), CARTKQTARKcrSTG (SEQ ID NO: 34), CSGRGKcrGG (SEQ ID NO: 35) and CGLGKGGAKcrRHR (SEQ ID NO: 36).

The crotonylation site may be selected from the group consisting of human H1.2K33, H1.2K63, H1.2K84, H1.2K89, H1.2K96, H1.2K158, H1.2K167, H2AK36, H2AK118, H2AK119, H2AK125, H2BK5, H2BK11, H2BK12, H2BK15, H2BK16, H2BK20, H2BK23, H2BK34, H3K4, H3K9, H3K18, H3K23, H3K27, H3K56, H4K5, H4K8, H4K12 and H4K16. Preferably, the crotonylation site is human H2AK119, H2BK11, H2BK12, H2BK16, H2BK20, H2BK34, H3K4, H3K18, H3K23, or H3K27.

A method for producing a Kcr-specific affinity reagent is also provided. The Kcr-specific affinity reagent binds specifically to a protein or a fragment thereof comprising a crotonylation site.

Where the Kcr-specific affinity reagent is an antibody, the Kcr-specific affinity reagent may be produced by immunizing a host with a peptide of the present invention. The peptide may comprise a sequence selected from SEQ ID NOs: 11-43.

Where the Kcr-specific affinity reagent is a polypeptide, the Kcr-specific affinity reagent may be produced by screening synthetic peptide library using a peptide of the present invention. The synthetic peptide library may be a phage display library or a yeast display library. The peptide may comprise a sequence selected from SEQ ID NOs: 11-43.

An isolated Kcr-specific affinity reagent is further provided. The isolated Kcr-specific affinity reagent is capable of binding specifically to the peptide of the present invention. The peptide may comprise a sequence selected from SEQ ID NOs: 11-43.

The binding of the Kcr-specific affinity reagent may be dependent on the crotonylation site, but not its surrounding peptide sequence. It may recognize a polypeptide comprising a crotonyllysine residue.

The binding of the Kcr-specific affinity reagent may be dependent on the crotonylation site and its surrounding peptide sequence. It may bind specifically to the peptide when crotonylated at the crotonylation site, but not the peptide when not crotonylated at the crotonylation site. The crotonylation site may be selected from the group consisting of human H1.2K33, H1.2K63, H1.2K84, H1.2K89, H1.2K96, H1.2K158, H1.2K167, H2AK36, H2AK118, H2AK119, H2AK125, H2BK5, H2BK11, H2BK12, H2BK15, H2BK16, H2BK20, H2BK23, H2BK34, H3K4, H3K9, H3K18, H3K23, H3K27, H3K56, H4K5, H4K8, H4K12 and H4K16, preferably H2AK119, H2BK11, H2BK12, H2BK16, H2BK20, H2BK34, H3K4, H3K18, H3K23, and H3K27.

A method for detecting protein crotonylation in a sample is further provided. The detection method comprises contacting the sample with an isolated Kcr-specific affinity reagent of the present invention to form a binding complex. The Kcr-specific affinity reagent binds specifically to a protein or a fragment thereof comprising a crotonylation site when the protein or a fragment thereof is crotonylated at the crotonylation site. The method further comprises detecting the binding complex. The presence of the binding complex indicates protein crotonylation in the sample.

A kit for detecting protein crotonylation in a sample is further provided. The kit comprises an isolated Kcr-specific affinity reagent of the present invention. The Kcr-specific affinity reagent binds specifically to a protein or a fragment thereof comprising a crotonylation site when the protein or a fragment thereof is crotonylated at the crotonylation site.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 shows short-chain lysine acylations resulting in a crotonyllysine and a acetyllysine. (A) An illustration of the enzymatic reactions for lysine acetylation by lysine acetyltransferases (KATs) using acetyl-CoA as a cofactor, and a hypothesized mechanism for Kcr using crotonyl-CoA as a cofactor. (B) Ball-and-stick models of a crotonyl group and an acetyl group. The three-dimensional arrangement of four carbons and one oxygen of the crotonyl group are rigid and located in the same plane (left panel).

The two olefinic carbons of the crotonyl group are shown in yellow. In contrast, the tetrahedral CH3 in the acetyl group (right panel) can be rotated such that it is structurally very different from the crotonyl group. (C) Chemical structure of vinylacetyllysine (but-3-enoyllysine), methacryllysine, and cyclopropanecarboxyllysine. (D) Crotonyl-CoA metabolism pathways. Crotonyl-CoA was generated from butyryl-CoA or glutaryl-CoA, and oxidized to acetyl-CoA through multiple steps.

Figure 3:
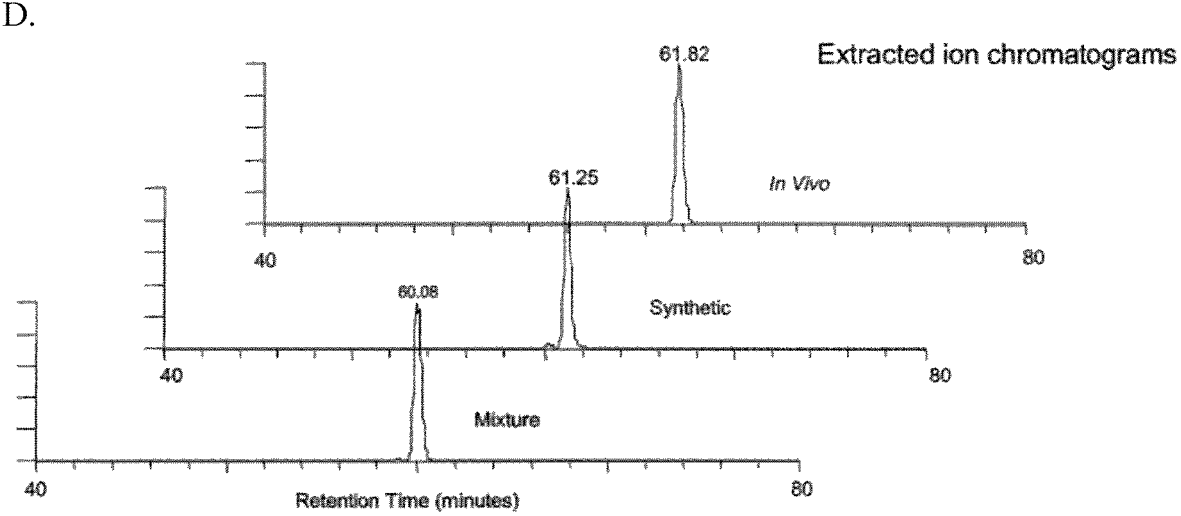

FIG. 3 shows identification and verification of a Kcr peptide, PEPAKcrSAPAPK (SEQ ID NO: 44), where "Kcr" represents a crotonyllysine residue. (A-C) High-resolution MS/MS spectrum of a tryptic peptide, PEPAKSAPAPK (SEQ ID NO: 44), with a mass of +68.0230 Da at its Lys5 residue identified from in vivo histone H2B (A), its synthetic Kcr counterpart (B), and a peptide mixture of the in vivo-derived tryptic peptide and its synthetic counterpart (C), each showing the same MS/MS fragmentation patterns and the same precursor ion mass. Inset shows their precursor ion masses. (D) Extracted ion chromatograms (XICs) of the in vivo-derived PEPAK+68.0230SAPAPK (SEQ ID NO: 44) peptide, the synthetic Kcr counterpart, and their mixture by nano-HPLC/MS/MS analysis using a reversed-phase HPLC column, showing the coelution of the two peptides.

FIG. 4 shows lysine crotonylation (Kcr) in histones. (A) Dot-spot assay using five peptide libraries, with the relative amounts as indicated, detected by an anti-Kcr pan antibody. Each peptide library contains 13 residues CXXXXXKXXXXXX (SEQ ID NO: 45), where X is a mixture of 19 amino acids (excluding cysteine), C is cysteine, and the 7th residue is a fixed lysine residue: unmodified lysine (K), Kac, propionyllysine (Kpr), butyryllysine (Kbu), or Kcr. (B) BSA, vinylacetyl-K BSA, methacryl-K BSA and crotonyl-K BSA detected by an anti-Kcr pan antibody by Western blotting (top panel) and by blue stain (bottom panel). (C) Core histone proteins H2A, H2B, H3, H4 and linker histone H1 with completion of a peptide library bearing an unmodified lysine (K), methacryl-K or Kcr as detected by Western blotting with an anti-Kcr pan antibody (top panel) or blue stain (bottom panel). (D) Lysine crotonylation signal in core histone proteins H2A, H2B, H3, H4 and linker histone H1 were detected by Western blotting with an anti-Kcr pan antibody (top panel) or blue stain (bottom panel) with competition of a peptide library bearing an unmodified lysine (K), Kac, Kpr, Kbu or Kcr.

Figure 5:
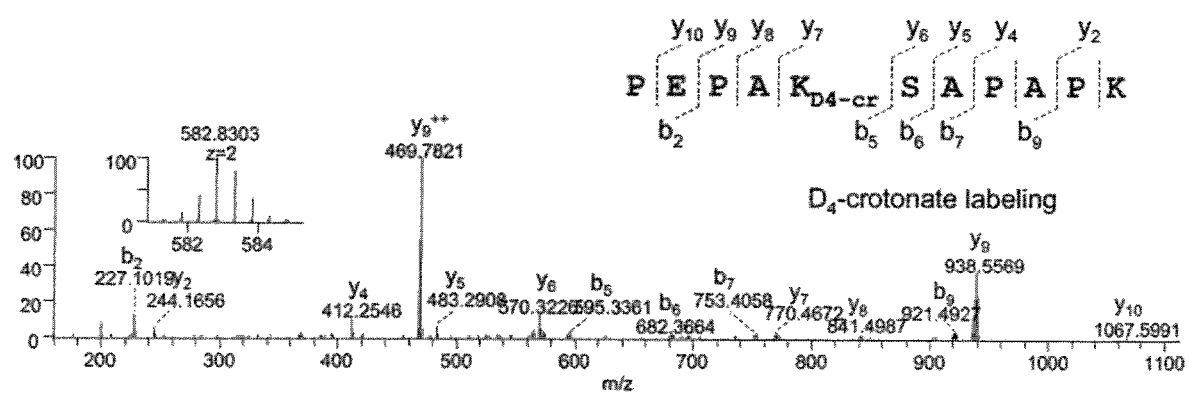

FIG. 5 shows lysine crotonylation (Kcr) in proteins by in vivo D4-crotonate isotopic labeling. (A) Dynamics of histone Kcr in response to crotonate. Histone proteins extracted from human prostate cancer cell line Du145 were incubated with 0, 50, or 100 mM crotonate for 24 hr, and then western blotted with an anti-Kcr pan antibody. (B) MS/MS spectrum of PEPAK$_{D4}$-crSAPAPK (SEQ ID NO: 44) identified from a D4-crotonate-labeled sample. A mixture of D4-, D3- and D2-crotonyl groups was used for the identification of D4-crotonyl peptide.

Figure 6:
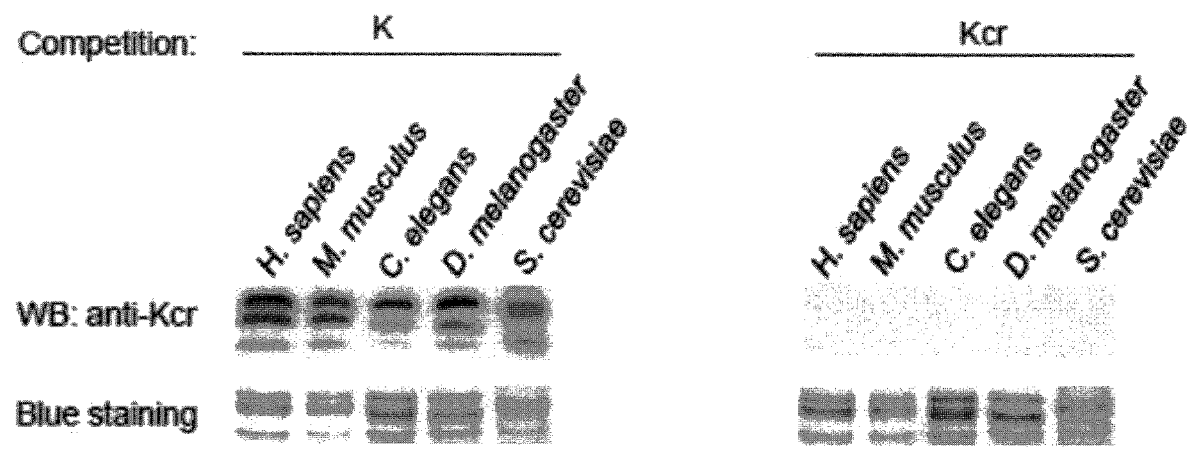

FIG. 6 shows histone crotonylation in different cell types. Kcr signals in core histones of *H. sapiens* (HeLa), *M. musculus* (MEF), *C. elegans, D. melanogaster* (S2), and *S. cerevisiae* cells by western blotting analysis with competition of lysine (K) (left panel) or crotonyllysine (Kcr) (right panel).

Figure 7:
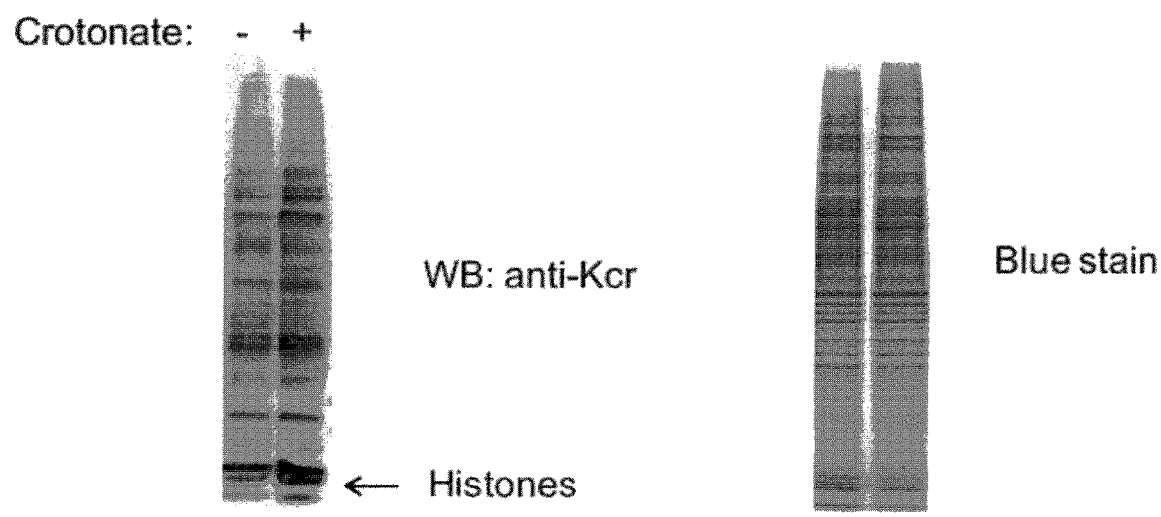

FIG. 7 shows crotonylation in HeLa cell lysates detected by Western blotting with an anti-Kcr pan antibody (left panel) and blue staining (right panel).

Figure 8:
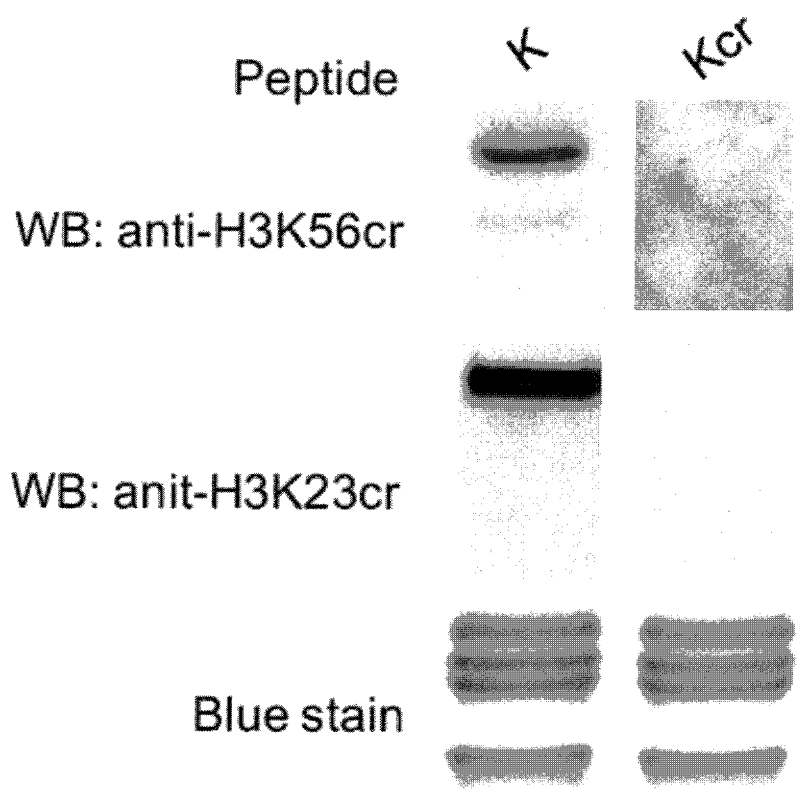

FIG. 8 shows crotonylation in Hela histones detected by Western blotting with sequence-specific antibodies against H3K56 (anti-H3K56cr; top panel) or H3K23 (anti-H3K23cr; middle panel), and by blue stain (bottom panel).

FIG. 9 shows protein sequences of human histone proteins (A) H1.2 (SEQ ID NO: 1), (B) H2A (SEQ ID NO: 2), (C) H2B (SEQ ID NO: 3), (D) H3 (SEQ ID NO: 4), and (E) H4 (SEQ ID NO: 5).

FIG. 10 shows protein sequences of mouse histone proteins (A) H1.2 (SEQ ID NO: 6), (B) H2A (SEQ ID NO: 7), (C) H2B (SEQ ID NO: 8), (D) H3 (SEQ ID NO: 9), and (E) H4 (SEQ ID NO: 10).

FIG. 11 shows detection of (A) crotonylated H2A peptide at Lys119 (lane 1), crotonylated H2A peptide at Lys118 (lane 2) and unmodified H2A peptide at Lys119 (lane 3) using anti-crotonyl-histone H2A (Lys119) rabbit pAb in dot blotting analysis, and (B) 30 µg of crude proteins from HeLa whole cell lysates without (left) or with (right) treatment of sodium crotonylate treatment (30 mM, 4 hours) using anti-crotonyl-histone H2A (Lys119) rabbit pAb (1:2000) in Western blotting analysis.

FIG. 12 shows detection of (A) crotonylated H2B peptide at Lys11 (lane 1), crotonylated H2B peptide at Lys12 (lane 2) and unmodified H2B peptide at Lys11 (lane 3) using anti-crotonyl-histone H2B (Lys11) rabbit pAb in dot blotting analysis, and (B) 30 µg of crude proteins from HeLa whole cell lysates without (left) or with (right) treatment of sodium crotonylate treatment (30 mM, 4 hours) using anti-crotonyl-histone H2B (Lys11) rabbit pAb (1:2000) in Western blotting analysis.

FIG. 13 shows detection of (A) crotonylated H2B peptide at Lys12 (lane 1), crotonylated H2B peptide at Lys12 (lane 2) and unmodified H2B peptide at Lys12 (lane 3) using anti-crotonyl-histone H2B (Lys12) rabbit pAb in dot blotting analysis, and (B) 30 µg of crude proteins from HeLa whole cell lysates without (left) or with (right) treatment of sodium crotonylate treatment (10 mM, 4 hours) using anti-crotonyl-histone H2B (Lys12) rabbit pAb (1:1000) in Western blotting analysis.

FIG. 14 shows detection of (A) crotonylated H2B peptide at Lys16 (lane 1) and unmodified H2B peptide at Lys16 (lane 2) using anti-crotonyl-histone H2B (Lys16) rabbit pAb in dot blotting analysis, and (B) 30 µg of crude proteins from HeLa whole cell lysates without (left) or with (right) treatment of sodium crotonylate treatment (30 mM, 4 hours) using anti-crotonyl-histone H2B (Lys16) rabbit pAb (1:1000) in Western blotting analysis.

FIG. 15 shows detection of (A) crotonylated H2B peptide at Lys20 (lane 1), butyrylated H2B peptide at Lys20 (lane 2), crotonylated H2B at Lys23 (lane 3) and unmodified H2B peptide at Lys12 (lane 4) using anti-crotonyl-histone H2B (Lys20) rabbit pAb in dot blotting analysis, and (B) 30 µg of crude proteins from HeLa whole cell lysates without (left) or with (right) treatment of sodium crotonylate treatment (10 mM, 4 hours) using anti-crotonyl-histone H2B (Lys20) rabbit pAb (1:2000) in Western blotting analysis.

FIG. 16 shows detection of (A) crotonylated H2B peptide at Lys34 (lane 1), succinylated H2B peptide at Lys34 (lane2) and unmodified H2B peptide at Lys34 (lane 3) using anti-crotonyl-histone H2B (Lys34) rabbit pAb in dot blotting analysis, and (B) 30 µg of crude proteins from HeLa whole cell lysates without (left) or with (right) treatment of sodium crotonylate treatment (30 mM, 4 hours) using anti-crotonyl-histone H2B (Lys34) rabbit pAb (1:2000) in Western blotting analysis.

FIG. 17 shows detection of (A) crotonylated H3 peptide at Lys4 (lane 1), crotonylated H3 peptide at Lys9 (lane 2), butyrylated H3 peptide at Lys9 (lane 3), and unmodified H3 peptide at Lys4 (lane 4) using anti-crotonyl-histone H3 (Lys4) rabbit pAb in dot blotting analysis, and (B) 30 µg of crude proteins from HeLa whole cell lysates without (left) or with (right) treatment of sodium crotonylate treatment (30 mM, 4 hours) using anti-crotonyl-histone H3 (Lys4) rabbit pAb (1:2000) in Western blotting analysis.

FIG. 18 shows detection of (A) crotonylated H3 peptide at Lys4 (lane 1), butyrylated H3 peptide at Lys9 (lane 2), crotonylated H3 peptide at Lys9 (lane 3) and unmodified H-3 peptide at Lys4 (lane 4) using anti-crotonyl-histone H3 (Lys4) mouse mAb in dot blotting analysis, and (B) 30 µg of crude proteins from HeLa whole cell lysates without (left) or with (right) treatment of sodium crotonylate treatment (30 mM, 4 hours) using anti-crotonyl-histone H3 (Lys4) mouse mAb (1:2000) in Western blotting analysis.

FIG. 19 shows detection of (A) crotonylated H 3 peptide at Lys18 (lane 1), butyrylated H3 peptide at Lys18 (lane 2), propionated H3 peptide at Lys18 (lane 3), and unmodified H3 peptide at Lys18 (lane 4) using crotonyl-histone H3 (Lys18) rabbit pAb in dot blotting analysis, and (B) 30 µg of crude proteins from HeLa whole cell lysates without (left) or with (right) treatment of sodium crotonylate treatment (30 mM, 4 hours) using anti-crotonyl-histone H3 (Lys18) rabbit pAb (1:1000) in Western blotting analysis.

FIG. 20 shows detection of (A) crotonylated H3 peptide at Lys23 (lane 1), butyrylated H3 peptide at Lys23 (lane 2), propionated H3 peptide at Lys23 (lane 3), and unmodified H3 peptide at Lys23 (lane 4) using crotonyl-histone H3 (Lys23) mouse mAb in dot blotting analysis, and (B) 30 µg of crude proteins from HeLa whole cell lysates without (left) or with (right) treatment of sodium crotonylate treatment (30 mM, 4 hours) using anti-crotonyl-histone H3 (Lys23) mouse mAb (1:1000) in Western blotting analysis.

FIG. 21 shows detection of (A) crotonylated H3 peptide at Lys23 (lane 1), butyrylated H3 peptide at Lys23 (lane 2), propionated H3 peptide at Lys23 (lane 3), and unmodified H3 peptide at Lys23 (lane 4) using crotonyl-histone H3 (Lys23) rabbit pAb in dot blotting analysis, and (B) 30 µg of crude proteins from HeLa whole cell lysates without (left) or with (right) treatment of sodium crotonylate treatment (30 mM, 4 hours) using anti-crotonyl-histone H3 (Lys23) rabbit pAb (1:1000) in Western blotting analysis.

FIG. 22 shows detection of (A) crotonylated H3 peptide at Lys27 (lane 1), acetylated H3 peptide at Lys27 (lane 2), and unmodified H3 peptide at Lys27 (lane 3) using crotonyl-histone H3 (Lys27) mouse mAb in dot blotting analysis, and (B) 30 µg of crude proteins from HeLa whole cell lysates without (left) or with (right) treatment of sodium crotonylate treatment (30 mM, 4 hours) using anti-crotonyl-histone H3 (Lys27) mouse mAb (1:2000) in Western blotting analysis.

DETAILED DESCRIPTION OF THE INVENTION

The present invention is based on the discovery of novel lysine crotonylation sites in proteins. In particular, peptides derived from histone proteins or fragments thereof comprising a crotonylation site are used to generate reagents useful for detecting protein crotonylation, especially for detecting site specific protein crotonylation.

The term "peptide" used herein refers to a linear chain of two or more amino acids linked by peptide bonds. A peptide may have about 2, 3, 4, 5, 6, 7, 8, 9, 10, 11, 12, 13, 14, 15, 16, 17, 18, 19, 20, 25, 30, 40, 50, 100, 200 or more amino acids. The amino acids of a peptide may be modified, deleted, added or substituted. A peptide may be obtained using conventional techniques known in the art. For example, a peptide may be synthesized or obtained from a native or recombinant protein by enzymatic digestion.

The term "polypeptide" used herein refers to a peptide having at least 4 amino acids, preferably at least about 20 amino acids, regardless of post-translational modification. The term "protein" used herein refers to a biological molecule consisting of one or more polypeptides, regardless of post-translational modification. Each polypeptide in a protein may be a subunit. The polypeptide or protein may be in a native or modified form, and may exhibit a biological function or characteristics.

Where a protein is a single polypeptide, the terms "protein" and "polypeptide" are used herein interchangeably. A fragment of a polypeptide or protein refers to a portion of the polypeptide or protein having an amino acid sequence that is the same as a part, but not all, of the amino acid sequence of the polypeptide or protein. Preferably, a fragment of a polypeptide or protein exhibits a biological function or characteristics identical or similar to that of the polypeptide or protein.

The term "derived from" used herein refers to the origin or source from which a biological molecule is obtained, and may include naturally occurring, recombinant, unpurified or purified molecules. A biological molecule such as a peptide (e.g., a polypeptide or protein) may be derived from an original molecule, becoming identical to the original molecule or a variant of the original molecule. For example, a peptide derived from an original peptide may have an amino acid sequence identical or similar to the amino acid sequence of its original peptide, with at least one amino acid modified, deleted, inserted, or substituted. A derived peptide may have an amino acid sequence at least about 5%, 10%, 20%, 30%, 40%, 50%, 60%, 70%, 80%, 90%, 95%, 99% or 100%, preferably at least about 50%, more preferably at least about 80%, most preferably at least about 90%, identical to the amino acid sequence of its original peptide, regardless of post-translational modification. Preferably, a derived biological molecule (e.g., a peptide) may exhibit a biological function or characteristics identical or similar to that of the original biological molecule.

The term "Kcr-specific affinity reagent" used herein refers to a molecule that is capable of binding to a protein having one or more crotonyllysine residues but not its unmodified counterpart. The Kcr-specific affinity reagent may be a peptide, polypeptide or protein. For example, the Kcr-specific affinity reagent may be an antibody.

The term "antibody" used herein includes whole antibodies, and antigen binding fragments (or antigen-binding portions) and single chains thereof. A whole antibody refers to a glycoprotein typically having two heavy chains and two light chains, and includes an antigen binding portion. The term "antigen binding portion" of an antibody used herein refers to one or more fragments of the antibody that retain the ability of specifically binding to an antigen. The term "single-chain variable fragment" of an antibody used herein refers to a fusion protein of the variable regions of the heavy and light chains of the antibody, connected with a short linker peptide, for example, of about 20-25 amino acids, that retains the ability of specifically binding to an antigen.

An isolated peptide comprising a crotonylation site is provided. The peptide may be derived from a protein, for example, a histone protein, or a fragment thereof comprising a crotonylation site. The peptide may be crotonylated or not crotonylated at the crotonylation site.

The peptide of the present invention may have at least about 3, 4, 5, 6, 7, 8, 9, 10, 11, 12, 13, 14, 15, 16, 17, 18, 19, 20, 30, 40, 50, 60, 70, 80, 90, 100, 150 or 200 amino acids. The peptide may have about 3-25 amino acids, preferably 5-20 amino acids, more preferably 6-14 amino acids.

The term "crotonylation" used herein refers to substitution of a hydrogen atom in a molecule (e.g., lysine) with a crotonyl group. For example, lysine may be crotonylated and become crotonyllysine.

A histone protein may be obtained from a eukaryotic cell. Examples of a eukaryotic cell include cells from a yeast (e.g., *S. cerevisiae*), an *C. elegans*, a Drosophila (e.g., *D. melanogaster* (S2)), a mouse (e.g., *M. musculus* (MEF)), or a human. Preferably, the eukaryotic cell is a mammalian cell, for example, a human, primate, mouse, rat, horse, cow, pig, sheep, goat, chicken, dog or cat cell. More preferably, the eukaryotic cell is a human cell.

A histone protein may be a histone linker protein or a histone core protein. A histone linker protein may be selected from the members of the H1 family, including the H1F subfamily (e.g., H1F0, H1FNT, H1FOO, and H1FX) and the H1H1 subfamily (e.g., HIST1H1A, HIST1H1B, HIST1H1C, HIST1H1D, HIST1H1E and HIST1H1T). A histone core protein may a member of the H2A, H2B, H3 or H4 family. A histone core protein in the H2A family may be a member of the H2AF subfamily (e.g., H2AFB1, H2AFB2, H2AFB3, H2AFJ, H2AFV, H2AFX, H2AFY, H2AFY2, and H2AFZ), the H2A1 subfamily (e.g., HIST1H2AA, HIST1H2AB, HIST1H2AC, HIST1H2AD, HIST1H2AE, HIST1H2AG, HIST1H2AI, HIST1H2AJ, HIST1H2AK, HIST1H2AL, and HIST1H2AM), or the H2A2 subfamily (e.g., HIST2H2AA3, and HIST2H2AC). A histone core protein in the H2B family may be a member of the H2BF subfamily (e.g., H2BFM, H2BFO, H2BFS, and H2BFWT), the H2B1 subfamily (e.g., HIST1H2BA, HIST1H2BB, HIST1H2BC, HIST1H2BD, HIST1H2BE, HIST1H2BF, HIST1H2BG, HIST1H2BH, HIST1H2BI, HIST1H2BJ, HIST1H2BK, HIST1H2BL, HIST1H2BM, HIST1H2BN, and HIST1H2BO), or the H2B2 subfamily (e.g., HIST2H2BE). A histone core protein in the H3 family may be a member of the H3A1 subfamily (e.g., HIST1H3A, HIST1H3B, HIST1H3C, HIST1H3D, HIST1H3E, HIST1H3F, HIST1H3G, HIST1H3H, HIST1H3I, and HIST1H3J), the H3A2 subfamily (e.g., HIST2H3C), or the H3A3 subfamily (e.g., HIST3H3). A histone core protein in the H4 family may be a member of the H41 subfamily (e.g., HIST1H4A, HIST1H4B, HIST1H4C, HIST1H4D, HIST1H4E, HIST1H4F, HIST1H4G, HIST1H4H, HIST1H4I, HIST1H4J, HIST1H4K, and HIST1H4L), or the H44 subfamily (e.g., HIST4H4).

The protein and gene sequences of histone proteins in various species are known in the art. The protein sequences of human H1.2, H2A, H2B, H3 and H4 histone proteins can be found in GenBank database Accession Nos. P16403 (H12_HUMAN) having SEQ ID NO: 1 (FIG. 9A), P04908 (H2A1B_HUMAN) having SEQ ID NO: 2 (FIG. 9B), P33778 (H2B1B_HUMAN) having SEQ ID NO: 3 (FIG. 9C), P84243 (H33_HUMAN) having SEQ ID NO: 4 (FIG.

9D) and P62805 (H4_HUMAN) having SEQ ID NO: 5 (FIG. 9E) respectively. The full-length protein sequences of mouse histone proteins H1.2, H2A, H2B, H3 and H4 can be found in the GenBank database Accession Nos. P15864 (H12_MOUSE) having SEQ ID NO: 6 (FIG. 10A), P22752 (H2A1_MOUSE) having SEQ ID NO: 7 (FIG. 10B), Q64475 (H2B1B_MOUSE) having SEQ ID NO: 8 (FIG. 10C), P84244 (H33_MOUSE) having SEQ ID NO: 9 (FIG. 10D) and. P62806 (H4_MOUSE) having SEQ ID NO: 10 (FIG. 10E), respectively.

A histone protein may be crotonylated at a crotonylation site. A crotonylation site may be lysine 33 (H1.2K33), lysine 63 (H1.2K63), lysine 84 (H1.2K84), lysine 89 (H1.2K89), lysine 96 (H1.2K96), lysine 158 (H1.2K158), or lysine 167 (H1.2K167) in a human H1.2 histone protein (SEQ ID NO: 1); lysine 36 (H2AK36), lysine 118 (H2AK118), lysine 119 (H2AK119), or lysine 125 (H2AK125) in human H2A histone protein (SEQ ID NO: 2); lysine 5 (H2BK5), lysine 11 (H2BK11), lysine 12 (H2BK12), lysine 15 (H2BK15), lysine 16 (H2BK16), lysine 20 (H2BK20), lysine 23 (H2BK23), or lysine 34 (H2BK34) in human H2B histone protein (SEQ ID NO: 3); lysine 4 (H3K4), lysine 9 (H3K9), lysine 18 (H3K18), lysine 23 (H3K23), lysine 27 (H3K27), or lysine 56 (H3K56) in human H3 histone protein (SEQ ID NO: 4); or lysine 5 (H4K5), lysine 8 (H4K8), lysine 12 (H4K12), or lysine 16 (H4K16) in human H4 histone protein (SEQ ID NO: 5).

Many crotonylation sites in histone proteins are conserved among different species (FIG. 1E). A mouse H1.2 histone protein (SEQ ID NO: 6) comprises crotonylation sites at lysine 33 (H1.2K33), lysine 63 (H1.2K63), lysine 84 (H1.2K84), lysine 158 (H1.2K158), and lysine 167 (H1.2K167) of SEQ ID NO: 6, corresponding to human H1.2K33, H1.2K63, H1.2K84, H1.2K158 and H1.2K167, respectively. A mouse H2A histone protein (SEQ ID NO: 7) comprises crotonylation sites at lysine 36 (H2AK36), and lysine 118 (H2AK118) of SEQ ID NO: 7, corresponding to human H2AK36 and H2AK118, respectively. A mouse H2B histone protein (SEQ ID NO: 8) comprises crotonylation sites at lysine 5 (H2BK5), lysine 11 (H2BK11), lysine 12 (H2BK12), lysine 15 (H2BK15), lysine 16 (H2BK16), lysine 20 (H2BK20), lysine 23 (H2BK23), and lysine 34 (H2BK34) of SEQ ID NO: 8, corresponding to human H2BK5, H2BK11, H2BK12, H2BK15, H2BK16, H2BK20, H2BK23, and H2BK34, respectively. A mouse H3 histone protein (SEQ ID NO: 9) comprises a crotonylation site comprises lysine 4 (H3K4), lysine 9 (H3K9), lysine 18 (H3K18), lysine 23 (H3K23), lysine 27 (H3K27), and lysine 56 (H3K56) of SEQ ID NO: 9, corresponding to human H3K4, H3K9, H3K18, H3K23, H3K27, H3K56, respectively. A mouse H4 histone protein crotonylation site (SEQ ID NO: 10) comprises crotonylation sites at lysine 5 (H4K5), lysine 8 (H4K8), and lysine 16 (H4K16) of SEQ ID NO: 10, of which mouse H4K5 and H4K8 correspond to the human H4K5 and H4K8, respectively.

A fragment of a histone protein may have an amino acid sequence that is the same as a part, not all, of the amino acid sequence of the histone protein comprising at least one crotonylation site in the histone protein. A histone protein fragment may have at least about 1, 2, 3, 4, 5, 6, 7, 8, 9, 10, 11, 12, 13, 14, 15, 16, 17, 18, 19, 20, 30, 40, 50, 60, 70, 80, 90, 100, 150 or 200 amino acids. A fragment of a histone protein may have about 3-25 contiguous amino acids, preferably about 5-20 contiguous amino acids, more preferably about 6-14 contiguous amino acids, of the histone protein covering at least one crotonylation site in the histone protein.

An isolated peptide of the present invention may be prepared using conventional techniques known in the art. The peptide may be a histone peptide derived from a histone protein or a fragment thereof comprising a crotonylation site. A histone protein may be obtained from a biological sample or prepared using recombinant techniques. A fragment of a histone protein may be prepared by recombinant techniques, or by digesting the histone protein with an enzyme (e.g., trypsin). The histone protein or a fragment thereof may be crotonylated naturally or artificially at a crotonylation site. The presence of a crotonyllysine may be confirmed by using conventional techniques known in the art, for example, mass spectrometry.

An isolated peptide of the present invention may comprise a sequence selected from the group consisting of SEQ ID NOs: 11-43. The peptides may encompass various regions and crotonylation sites in human histone proteins (Table 1). These peptides may comprise a crotonylated lysine residue (Kcr) (also known as a crotonyllysine residue). Examples of crotonylated peptides covering crotonylation sites in human histone proteins are shown in Table 1.

A method for producing a Kcr-specific affinity reagent is provided. The Kcr-specific affinity reagent specifically binds to a protein or a fragment thereof comprising a crotonyllysine. The protein may be a histone protein.

The Kcr-specific affinity reagent may be an antibody produced by different methods known in the art. For example, the production method may comprise immunizing a host with an antigenic peptide to produce the antibody. The method may further comprise collecting antisera from the host. The antigenic peptide may be derived from a histone protein or a fragment thereof comprising the crotonylation site. The antigenic peptide may comprise a peptide of the present invention. The antigenic peptide may be crotonylated or not crotonylated. Examples of the non-crotonylated antigenic peptides include QLATKAA (SEQ ID NO: 11), CQLATKAA (SEQ ID NO: 12), YQKST (SEQ ID NO: 13), CYQKSTELL (SEQ ID NO: 14), LLPKKTESHHKAK (SEQ ID NO: 15), CLLPKKTESHHKAKG (SEQ ID NO: 16), APAPKKGS (SEQ ID NO: 17), APAPKKGSC (SEQ ID NO: 18), CAPAPKKGS (SEQ ID NO: 19), GSKKA (SEQ ID NO: 20), GSKKAVTC (SEQ ID NO: 21), TKAQKKDG (SEQ ID NO: 22), AVTKAQKKDGC (SEQ ID NO: 23), ARTKQTAR (SEQ ID NO: 24), ARTKQTARC (SEQ ID NO: 25), APRKQLA (SEQ ID NO: 26), APRKQLATC (SEQ ID NO: 27), QLATKAARK (SEQ ID NO: 28), QLATKAARKC (SEQ ID NO: 29), AARKSAP (SEQ ID NO: 30), AARKSAPATGGC (SEQ ID NO: 31), CRLLRKGNYAER (SEQ ID NO: 32), CAVTKAQKKDG (SEQ ID NO: 33), CARTKQTARKSTG (SEQ ID NO: 34), CSGRGKGG (SEQ ID NO: 35) and CGLGKGGAKRHR (SEQ ID NO: 36). Examples of the crotonylated antigenic peptides include include QLATKcrAA (SEQ ID NO: 11), CQLATKcrAA (SEQ ID NO: 12), YQKcrST (SEQ ID NO: 13), CYQKcrSTELL (SEQ ID NO: 14), LLPKKcrTESHHKAK (SEQ ID NO: 15), CLLPKKcrTESHHKAKG (SEQ ID NO: 16), APAPKcrKGS (SEQ ID NO: 17), APAPKcrKGSC (SEQ ID NO: 18), APAPKKcrGS (SEQ ID NO: 17), CAPAPKKcrGS (SEQ ID NO: 19), GSKKcrA (SEQ ID NO: 20), GSKKcrAVTC (SEQ ID NO: 21), TKcrAQKKDG (SEQ ID NO: 22), AVTKcrAQKKDGC (SEQ ID NO: 23), ARTKcrQTAR (SEQ ID NO: 24), ARTKcrQTARC (SEQ ID NO: 25), APRKcrQLA (SEQ ID NO: 26), APRKcrQLATC (SEQ ID NO: 27), QLATKcrAARK (SEQ ID NO: 28), QLATKcrAARKC (SEQ ID NO: 29), AARKcrSAP (SEQ ID NO: 30), AARKcrSAPATGGC (SEQ ID NO:

31), CRLLRKcrGNYAER (SEQ ID NO: 32), CLLPKcrK-TESHHKAKG (SEQ ID NO: 16), CLLPKK-TESHHKcrAKG (SEQ ID NO: 16), CAVTKAQKcrKDG (SEQ ID NO: 33), CARTKQTARKcrSTG (SEQ ID NO: 34), CSGRGKcrGG (SEQ ID NO: 35). The N-terminal or C-terminal end of any of these peptides may be extended by 1-20 residues, depending on the proteolytic enzymes used for digestion of histone proteins.

The method may further comprise purifying the antibody from the antisera. The method may further comprise utilizing spleen cells from the host to generate a monoclonal antibody. In some embodiments, the antibody specifically binds to a histone protein or a fragment thereof when the histone protein or a fragment thereof is crotonylated at the crotonylation site, and does not bind to the histone protein or a fragment thereof when the histone protein or a fragment thereof is not crotonylated at the crotonylation site. In other embodiments, the antibody specifically binds to the histone protein or a fragment thereof when the histone protein or a fragment thereof is not crotonylated at the crotonylation site, and does not bind to the histone protein or a fragment thereof when the histone protein or a fragment thereof is crotonylated at the crotonylation site.

The host may be a mammal suitable for producing antibodies. For example, the host may be a mouse, rabbit, or goat.

The Kcr-specific affinity reagent may be a polypeptide. The polypeptide may be produced by screening a synthetic peptide library using a peptide comprising the peptide of the present invention. The synthetic peptide library may be a phage display library, a yeast display library or other synthetic peptide library comprising peptides having randomized amino acid sequences.

Also provided is an isolated Kcr-specific affinity reagent that specifically binds to a peptide of the present invention. The Kcr-specific affinity reagent may be an antibody or a polypeptide derived by screening a synthetic peptide library. In some embodiments, the Kcr-specific affinity reagent specifically binds to the peptide when crotonylated, and does not bind to the peptide when not crotonylated. The binding of the Kcr-specific affinity reagent to a peptide of the present invention may be dependent on the crotonylation site, but not its surrounding peptide sequence. For example, the Kcr-specific affinity reagent is an anti-crotonylation pan antibody.

The binding of the Kcr-specific affinity reagent to a peptide of the present invention may be dependent on the crotonylation site and its surrounding peptide sequence. It may recognize a polypeptide having a crotonyllysine residue. The recognition may depend on not only the crotonyllysine residue but also its surrounding 1-5 residues. In some embodiments, the crotonylation site specific Kcr-specific affinity reagent specifically binds to a histone protein or a fragment thereof when the histone protein or a fragment thereof is crotonylated at the crotonylation site, and does not bind to the histone protein or a fragment thereof when the histone protein or a fragment thereof is not crotonylated at the crotonylation site. Examples of crotonylation site specific Kcr-specific affinity reagents include anti-H3K23cr rabbit pAb, anti-H3K56cr rabbit pAb, anti-crotonyl-histone H2A (Lys119) rabbit pAb, anti-crotonyl-histone H2B (Lys11) rabbit pAb, anti-crotonyl-histone H2B (Lys12) rabbit pAb, anti-crotonyl-histone H2B (Lys16) rabbit pAb, anti-crotonyl-histone H2B (Lys20) rabbit pAb, anti-crotonyl-histone H2B (Lys34) rabbit pAb, anti-crotonyl-histone H3 (Lys4) rabbit pAb, anti-crotonyl-histone H3 (Lys4) mouse mAb, anti-crotonyl-histone H3 (Lys18) rabbit pAb, anti-crotonyl-histone H3 (Lys23) mouse mAb, anti-crotonyl-histone H3 (Lys23) rabbit pAb, and anti-crotonyl-histone H3 (Lys27) mouse mAb.

With respect to a Kcr-specific affinity reagent of the present invention, the crotonylation site may be any crotonylation site in any histone protein from any species. Examples of the crotonylation sites include human crotonylation sites H1.2K33, H1.2K63, H1.2K84, H1.2K89, H1.2K96, H1.2K158, H1.2K167, H2AK36, H2AK118, H2AK119, H2AK125, H2BK5, H2BK11, H2BK12, H2BK15, H2BK16, H2BK20, H2BK23, H2BK34, H3K4, H3K9, H3K18, H3K23, H3K27, H3K56, H4K5, H4K8, H4K12 and H4K16, mouse crotonylation sites H1.2K33, H1.2K63, H1.2K84, H1.2K158, H1.2K167, H2AK36, H2AK118, H2BK5, H2BK11, H2BK12, H2BK15, H2BK16, H2BK20, H2BK23, H2BK34, H3K4, H3K9, H3K18, H3K23, H3K27, H3K56, H4K5, H4K8, and H4K16, and homologous lysine sites in corresponding eukaryotic histone proteins.

The Kcr-specific affinity reagent may specifically bind to a human H1.2 histone protein (SEQ ID NO: 1) or a fragment thereof when the human H1.2 histone protein or a fragment thereof is crotonylated at a crotonylation site selected from the group consisting of human H1.2K33, H1.2K63, H1.2K84, H1.2K89, H1.2K96, H1.2K158 and H1.2K167, but not when the H1.2 histone protein or a fragment thereof is not crotonylated at the crotonylation site.

The Kcr-specific affinity reagent may specifically bind to a human H2A histone protein (SEQ ID NO: 2) or a fragment thereof when the human H2A histone protein or a fragment thereof is crotonylated at a crotonylation site selected from the group consisting of human H2AK36, H2AK118, H2AK119 (e.g., anti-crotonyl-histone H2A (Lys119) rabbit pAb) and H2AK125, but not when the H2A histone protein or a fragment thereof is not crotonylated at the crotonylation site.

The Kcr-specific affinity reagent may specifically bind to a human H2B histone protein (SEQ ID NO: 3) or a fragment thereof when the human H2B histone protein or a fragment thereof is crotonylated at a crotonylation site selected from the group consisting of human H2BK5, H2BK11 (e.g., anti-crotonyl-histone H2B (Lys11) rabbit pAb), H2BK12 (e.g., anti-crotonyl-histone H2B (Lys12) rabbit pAb), H2BK15, H2BK16 (e.g., anti-crotonyl-histone H2B (Lys16) rabbit pAb), H2BK20 (e.g., anti-crotonyl-histone H2B (Lys20) rabbit pAb), H2BK23 and H2BK34 (e.g., anti-crotonyl-histone H2B (Lys34) rabbit pAb), but not when the H2B histone protein or a fragment thereof is not crotonylated at the crotonylation site.

The Kcr-specific affinity reagent may specifically bind to a human H3 histone protein (SEQ ID NO: 4) or a fragment thereof when the human H3 histone protein or a fragment thereof is crotonylated at a crotonylation site selected from the group consisting of human H3K4 (e.g., anti-crotonyl-histone H3 (Lys4) rabbit pAb and anti-crotonyl-histone H3 (Lys4) mouse mAb), H3K9, H3K18 (e.g., anti-crotonyl-histone H3 (Lys18) rabbit pAb), H3K23 (e.g., anti-H3K23cr rabbit pAb, anti-crotonyl-histone H3 (Lys23) rabbit pAb, and anti-crotonyl-histone H3 (Lys23) mouse mAb), H3K27 (e.g., anti-crotonyl-histone H3 (Lys27) mouse mAb) and H3K56 (e.g., anti-H3K56cr rabbit pAb), but not when the H3 histone protein or a fragment thereof is not crotonylated at the crotonylation site.

The Kcr-specific affinity reagent may specifically bind to a human H4 histone protein (SEQ ID NO: 5) or a fragment thereof when the human H4 histone protein or a fragment thereof is crotonylated at a crotonylation site selected from the group consisting of human H4K5, H4K8, H4K12 and H4K16, but not when the H4 histone protein or a fragment thereof is not crotonylated at the crotonylation site.

The Kcr-specific affinity reagent may specifically bind to a mouse H1.2 histone protein (SEQ ID NO: 6) or a fragment thereof when the mouse H1.2 histone protein or a fragment thereof is crotonylated at a crotonylation site selected from the group consisting of mouse H1.2K33, H1.2K63, H1.2K84, H1.2K158 and H1.2K167, but not when the H1.2 histone protein or a fragment thereof is not crotonylated at the crotonylation site.

The Kcr-specific affinity reagent may specifically bind to a mouse H2A histone protein (SEQ ID NO: 7) or a fragment thereof when the mouse H2A histone protein or a fragment thereof is crotonylated at a crotonylation site selected from the group consisting of mouse H2AK36 and H2AK118, but not when the H2A histone protein or a fragment thereof is not crotonylated at the crotonylation site.

The Kcr-specific affinity reagent may specifically bind to a mouse H2B histone protein (SEQ ID NO: 8) or a fragment thereof when the mouse H2B histone protein or a fragment thereof is crotonylated at a crotonylation site selected from the group consisting of mouse H2BK5, H2BK11, H2BK12, H2BK15, H2BK16, H2BK20, H2BK23 and H2BK34, but not when the H2B histone protein or a fragment thereof is not crotonylated at the crotonylation site.

The Kcr-specific affinity reagent may specifically bind to a mouse H3 histone protein (SEQ ID NO: 9) or a fragment thereof when the mouse H3 histone protein or a fragment thereof is crotonylated at a crotonylation site selected from the group consisting of mouse H3K4, H3K9, H3K18, H3K23, H3K27 and H3K56, but not when the H3 histone protein or a fragment thereof is not crotonylated at the crotonylation site.

The Kcr-specific affinity reagent may specifically bind to a mouse H4 histone protein (SEQ ID NO: 10) or a fragment thereof when the mouse H4 histone protein or a fragment thereof is crotonylated at a crotonylation site selected from the group consisting of mouse H4K5, H4K8 and H4K16, but not when the H4 histone protein or a fragment thereof is not crotonylated at the crotonylation site.

The Kcr-specific affinity reagent may be polyclonal or monoclonal antibody. The polyclone or monoclonal antibody may be prepared using conventional techniques known in the art. An immortalized cell line may be prepared using conventional techniques known in the art to produce the monoclonal antibody. The monoclonal antibody may be generated by screening of a phage library, a synthetic peptide library, or a yeast library. The antibody may also be obtained from an antibody production method of the present invention.

The Kcr-specific affinity reagent of the present invention may be a whole antibody. The whole antibody consists of two heavy chains and two light chains. The heavy and light chains contain variable regions, which contribute to the specificity of antigen binding by the antibody. The whole antibody comprises an antigen binding portion. A crotonylation site specific binding domain within a whole antibody may be determined using conventional techniques known in the art.

The Kcr-specific affinity reagent of the present invention may be an antigen binding portion of a whole antibody. The antigen binding portion may specifically bind to a histone protein or a fragment thereof comprising a crotonylation site. In some embodiments, the antigen binding portion specifically binds to the histone protein or a fragment thereof when the histone protein or a fragment thereof is crotonylated, and does not bind to the histone protein or a fragment thereof when the histone protein or a fragment thereof is not crotonylated. Preferably, the antigen binding portion is crotonylation site specific. In some embodiments, the crotonylation site specific antigen binding portion specifically binds to a histone protein or a fragment thereof comprising a crotonylation site when the histone protein or a fragment thereof is crotonylated at the crotonylation site, and does not bind to the histone protein or a fragment thereof when the histone protein or a fragment thereof is not crotonylated at the crotonylation site.

The antigen binding portion may be obtained by using conventional techniques known in the art. A crotonylation site specific binding domain within an antigen binding portion may be determined using conventional techniques known in the art.

The Kcr-specific affinity reagent of the present invention may be a single-chain variable fragment that specifically binds to a protein or a fragment thereof comprising a crotonylation site. In some embodiments, the single-chain variable fragment specifically binds a histone protein or a fragment thereof when the histone protein or a fragment thereof is crotonylated, and does not bind to the histone protein or a fragment thereof when the histone protein or a fragment thereof is not crotonylated.

Preferably, the single-chain variable fragment is crotonylation site specific. In some embodiments, the crotonylation site specific single-chain variable fragment specifically binds to a histone protein or a fragment thereof comprising a crotonylation site when the histone protein or a fragment thereof is crotonylated at the crotonylation site, and does not bind to the histone protein or a fragment thereof when the histone protein or a fragment thereof is not crotonylated at the crotonylation site.

The single-chain variable fragment may be obtained as a fusion protein comprising variable regions of the heavy and light chains of a whole antibody, connected with a short linker peptide. The linker peptide may have about 1-50 amino acids, preferably about 1-30 amino acids, more preferably about 2-15 amino acids. In particular, the variable regions of the heavy and light chains may be determined by conventional techniques known in the art. A crotonylation site specific binding domain within a single-chain variable fragment may be determined using conventional techniques known in the art.

A method for detecting protein crotonylation in a sample is further provided. The method comprises (a) contacting the sample with a Kcr-specific affinity reagent of the present invention to form a binding complex, and (b) detecting the binding complex. The presence of the binding complex indicates protein crotonylation in the sample. The binding complex may be detected by using various conventional methods in the art. The protein crotonylation may be histone crotonylation. The Kcr-specific affinity reagent may specifically bind to a histone protein or a fragment thereof comprising a crotonylation site when the histone protein or a fragment thereof is crotonylated.

The sample may be a biological sample (e.g., bodily fluid or serum). The biological sample be obtained from a subject. The subject may be a mouse, rat or human. Preferably, the subject is a human, more preferably a human who has suffered from or is predisposed to a disease or disorder (e.g., cancer, neurodegenerative diseases, aging, metabolic disorder, or dysgenesis).

Any of the Kcr-specific affinity reagents of the present invention may be used for the crotonylation detection method. Preferably, the Kcr-specific affinity reagent is a crotonylation site specific antibody. More preferably, the crotonylation site specific antibody specifically binds to a histone protein or a fragment thereof when the histone protein or a fragment thereof is crotonylated at the crotonylation site, and does not bind to the histone protein or a fragment thereof when the histone protein or a fragment thereof is not crotonylated at the crotonylation site. The histone protein may be selected from the group consisting of human and mouse H1.2, H2A, H2B, H3 and H4 histone proteins. The crotonylation site may be selected from the group consisting of human H1.2K33, H1.2K63, H1.2K84, H1.2K89, H1.2K96, H1.2K158, H1.2K167, H2AK36, H2AK118, H2AK119, H2AK125, H2BK5, H2BK11, H2BK12, H2BK15, H2BK16, H2BK20, H2BK23, H2BK34, H3K4, H3K9, H3K18, H3K23, H3K27, H3K56, H4K5, H4K8, H4K12 and H4K16, and mouse H1.2K33, H1.2K63, H1.2K84, H1.2K158, H1.2K167, H2AK36, H2AK118, H2BK5, H2BK11, H2BK12, H2BK15, H2BK16, H2BK20, H2BK23, H2BK34, H3K4, H3K9, H3K18, H3K23, H3K27, H3K56, H4K5, H4K8 and H4K16, and homologous lysine sites in corresponding eukaryotic histone proteins.

The Kcr-specific affinity reagents of the present invention may be useful for detecting protein crotonylation in a sample. Exemplary Kcr-specific affinity reagents include those that specifically bind to a human H1.2 histone protein (SEQ ID NO: 1) when crotonylated at H1.2K33, H1.2K63, H1.2K84, H1.2K89, H1.2K96, H1.2K158 or H1.2K167; a human H2A histone protein (SEQ ID NO: 2) when crotonylated at H2AK36, H2AK118, H2AK119 or H2AK125; a human H2B histone protein (SEQ ID NO: 3) when crotonylated at H2BK5, H2BK11, H2BK12, H2BK15, H2BK16, H2BK20, H2BK23 or H2BK34; a human H3 histone protein (SEQ ID NO: 4) when crotonylated at H3K4, H3K9, H3K18, H3K23, H3K27 or H3K56; a human H4 histone protein (SEQ ID NO: 5) when crotonylated at H4K5, H4K8, H4K12 or H4K16; a mouse H1.2 histone protein (SEQ ID NO: 6) when crotonylated at H1.2K33, H1.2K63, H1.2K84, H1.2K158 or H1.2K167; a mouse H2A histone protein (SEQ ID NO: 7) when crotonylated at H2AK36 or H2AK118; a mouse H2B histone protein (SEQ ID NO: 8) when crotonylated at H2BK5, H2BK11, H2BK12, H2BK15, H2BK16, H2BK20, H2BK23 or H2BK34; a mouse H3 histone protein (SEQ ID NO: 9) when crotonylated at H3K4, H3K9, H3K18, H3K23, H3K27 or H3K56; or a mouse H4 histone protein (SEQ ID NO: 10) when crotonylated at H4K5, H4K8 or H4K16. Examples of suitable Kcr-specific affinity reagents include anti-H3K23cr rabbit pAb, anti-H3K56cr rabbit pAb, anti-crotonyl-histone H2A (Lys119) rabbit pAb, anti-crotonyl-histone H2B (Lys11) rabbit pAb, anti-crotonyl-histone H2B (Lys12) rabbit pAb, anti-crotonyl-histone H2B (Lys16) rabbit pAb, anti-crotonyl-histone H2B (Lys20) rabbit pAb, anti-crotonyl-histone H2B (Lys34) rabbit pAb, anti-crotonyl-histone H3 (Lys4) rabbit pAb, anti-crotonyl-histone H3 (Lys4) mouse mAb, anti-crotonyl-histone H3 (Lys18) rabbit pAb, anti-crotonyl-histone H3 (Lys23) mouse mAb, anti-crotonyl-histone H3 (Lys23) rabbit pAb, and anti-crotonyl-histone H3 (Lys27) mouse mAb.

For each protein crotonylation detection method of the present invention, a kit is provided. The kit comprises a Kcr-specific affinity reagent that specifically binds to a protein or a fragment thereof comprising a crotonylation site. The kit may include an instruction directing how to carry out the detection method. The protein crotonylation may be histone crotonylation. Preferably, the Kcr-specific affinity reagent specifically binds to a protein or a fragment thereof comprising when the protein or a fragment thereof is crotonylated at the crotonylation site. The Kcr-specific affinity reagent may be an isolated antibody of the present invention. Examples of suitable antibodies include anti-H3K23cr rabbit pAb, anti-H3K56cr rabbit pAb, anti-crotonyl-histone H2A (Lys119) rabbit pAb, anti-crotonyl-histone H2B (Lys11) rabbit pAb, anti-crotonyl-histone H2B (Lys12) rabbit pAb, anti-crotonyl-histone H2B (Lys16) rabbit pAb, anti-crotonyl-histone H2B (Lys20) rabbit pAb, anti-crotonyl-histone H2B (Lys34) rabbit pAb, anti-crotonyl-histone H3 (Lys4) rabbit pAb, anti-crotonyl-histone H3 (Lys4) mouse mAb, anti-crotonyl-histone H3 (Lys18) rabbit pAb, anti-crotonyl-histone H3 (Lys23) mouse mAb, anti-crotonyl-histone H3 (Lys23) rabbit pAb, and anti-crotonyl-histone H3 (Lys27) mouse mAb.

A fusion protein reporter is provided. The fusion protein reporter comprises a core flanked by a donor fluorescent moiety and an acceptor fluorescent moiety. The core comprises a peptide comprising a crotonylation site, and a crotonylation binding domain.

The fusion protein reporter of the present invention is useful for determining the protein crotonylation level in a sample or screening for an agent that regulates protein crotonylation by using the fluorescence resonance energy transfer (FRET). The FRET involves the transfer of photonic energy between fluorophores when in close proximity. Donor fluorescent moieties and acceptor fluorescent moieties suitable for FRET are known in the art. In the fusion protein reporter, the donor fluorescent moiety may be selected from the group consisting of cyan fluorescent protein (CFP), enhanced cyan fluorescent protein (ECFP), and A206K mutants thereof, and the acceptor fluorescent moiety may be selected from the group consisting of yellow fluorescent protein (YFP), enhanced yellow fluorescence protein (EYFP), Citrine, Venus, and A206K mutants thereof.

The peptide in the fusion protein reporter may be a peptide of the present invention. It may be a peptide derived from a histone protein or a fragment thereof comprising the crotonylation site. It may be crotonylated or not crotonylated at the crotonylation site.

The crotonylation site may be located in the N-terminus, C-terminus or the core region of a histone protein. The N-terminus, C-terminus, and core regions of histone proteins (e.g., human or mouse H1.2, H2A, H2B, H3 or H4) are known in the art.

The fusion protein reporter may comprise one or more crotonylation binding domains. A crotonylation binding domain may be derived from a Kcr-specific affinity reagent that specifically binds to a histone protein or a fragment thereof comprising a crotonylation site when the histone protein or a fragment thereof is crotonylated or not crotonylated at the crotonylation site. The crotonylation binding domain may be the crotonylation site specific binding domain within a Kcr-specific affinity reagent, for example, a whole antibody, an antigen binding portion, or a single-chain variable fragment, of the present invention. The crotonylation binding domain may be derived from a Kcr-specific affinity reagent of the present invention.

In some embodiments, the peptide is not crotonylated at the crotonylation site, and the crotonylation binding domain specifically binds to the peptide when the peptide is crotonylated at the crotonylation site, and does not bind to the peptide when the peptide is not crotonylated at the crotonylation site. Examples of the non-crotonylated peptides include QLATKAA (SEQ ID NO: 11), CQLATKAA (SEQ ID NO: 12), YQKST (SEQ ID NO: 13), CYQKSTELL (SEQ ID NO: 14), LLPKKTESHHKAK (SEQ ID NO: 15), CLLPKKTESHHKAKG (SEQ ID NO: 16), APAPKKGS (SEQ ID NO: 17), APAPKKGSC (SEQ ID NO: 18), CAPAPKKGS (SEQ ID NO: 19), GSKKA (SEQ ID NO: 20), GSKKAVTC (SEQ ID NO: 21), TKAQKKDG (SEQ ID NO: 22), AVTKAQKKDGC (SEQ ID NO: 23), ARTKQTAR (SEQ ID NO: 24), ARTKQTARC (SEQ ID NO: 25), APRKQLA (SEQ ID NO: 26), APRKQLATC (SEQ ID NO: 27), QLATKAARK (SEQ ID NO: 28), QLATKAARKC (SEQ ID NO: 29), AARKSAP (SEQ ID NO: 30), AARKSAPATGGC (SEQ ID NO: 31), CRLLRKGNYAER (SEQ ID NO: 32), CAVTKAQKKDG (SEQ ID NO: 33), CARTKQTARKSTG (SEQ ID NO: 34), CSGRGKGG (SEQ ID NO: 35) and CGLGKGGAKRHR (SEQ ID NO: 36).

In other embodiments, the peptide is crotonylated at the crotonylation site, and the crotonylation binding domain specifically binds to the peptide when the peptide is not crotonylated at the crotonylation site, and does not bind to the peptide when the peptide is crotonylated at the crotonylation site. Examples of the crotonylated peptides include QLATKcrAA (SEQ ID NO: 11), CQLATKcrAA (SEQ ID NO: 12), YQKcrST (SEQ ID NO: 13), CYQKcrSTELL (SEQ ID NO: 14), LLPKKcrTESHHKAK (SEQ ID NO: 15), CLLPKKcrTESHHKAKG (SEQ ID NO: 16), APAPKcrKGS (SEQ ID NO: 17), APAPKcrKGSC (SEQ ID NO: 18), APAPKKcrGS (SEQ ID NO: 17), CAPAPKKcrGS (SEQ ID NO: 19), GSKKcrA (SEQ ID NO: 20), GSKKcrAVTC (SEQ ID NO: 21), TKcrAQKKDG (SEQ ID NO: 22), AVTKcrAQKKDGC (SEQ ID NO: 23), ARTKcrQTAR (SEQ ID NO: 24), ARTKcrQTARC (SEQ ID NO: 25), APRKcrQLA (SEQ ID NO: 26), APRKcrQLATC (SEQ ID NO: 27), QLATKcrAARK (SEQ ID NO: 28), QLATKcrAARKC (SEQ ID NO: 29), AARKcrSAP (SEQ ID NO: 30), AARKcrSAPATGGC (SEQ ID NO: 31), CRLLRKcrGNYAER (SEQ ID NO: 32), CLLPKcrKTESHHKAKG (SEQ ID NO: 16), CLLPKKTESHHKcrAKG (SEQ ID NO: 16), CAVTKAQKcrKDG (SEQ ID NO: 33), CARTKQTARKcrSTG (SEQ ID NO: 34), CSGRGKcrGG (SEQ ID NO: 35) and CGLGKGAKcrRHR (SEQ ID NO: 36). The peptide may be conjugated to the crotonylation binding domain with a linker molecule. The linker molecule may be a peptide have any amino acid sequence, and may have about 1-50 amino acids, preferably 1-30 amino acids, more preferably 2-15. In some embodiments, the linker molecule may be -Gly-Gly-. The length and contents of a linker molecule may be adjusted to optimize potential fluorescence resonance energy transfer (FRET) between the donor fluorescent moiety and the acceptor fluorescent moiety when the peptide in the fusion protein reporter is crotonylated, or de-crotonylated, and bound by the crotonylation binding domain.

The fusion protein reporter may further comprise a targeting polypeptide. The targeting polypeptide may be selected from the group consisting of a receptor ligand, a nuclear localization sequence (NLS), a nuclear export signal (NES), a plasma membrane targeting signal, a histone binding protein, and a nuclear protein.

A method for determining the level of protein crotonylation in a sample is provided. The method comprises (a) contacting the sample with a fusion protein reporter, and (b) comparing the level of fluorescence resonance energy transfer (FRET) between the donor fluorescent moiety and the acceptor fluorescent moiety after contacting with that before contacting. The fusion protein reporter comprises a core flanked by a donor fluorescent moiety and an acceptor fluorescent moiety. The core comprises a peptide comprising a crotonylation site, and a crotonylation binding domain. The peptide is not crotonylated at the crotonylation site. Examples of the non-crotonylated peptides include QLATKAA (SEQ ID NO: 11), CQLATKAA (SEQ ID NO: 12), YQKST (SEQ ID NO: 13), CYQKSTELL (SEQ ID NO: 14), LLPKKTESHHKAK (SEQ ID NO: 15), CLLPKKTESHHKAKG (SEQ ID NO: 16), APAPKKGS (SEQ ID NO: 17), APAPKKGSC (SEQ ID NO: 18), CAPAPKKGS (SEQ ID NO: 19), GSKKA (SEQ ID NO: 20), GSKKAVTC (SEQ ID NO: 21), TKAQKKDG (SEQ ID NO: 22), AVTKAQKKDGC (SEQ ID NO: 23), ARTKQTAR (SEQ ID NO: 24), ARTKQTARC (SEQ ID NO: 25), APRKQLA (SEQ ID NO: 26), APRKQLATC (SEQ ID NO: 27), QLATKAARK (SEQ ID NO: 28), QLATKAARKC (SEQ ID NO: 29), AARKSAP (SEQ ID NO: 30), AARKSAPATGGC (SEQ ID NO: 31), CRLLRKGNYAER (SEQ ID NO: 32), CAVTKAQKKDG (SEQ ID NO: 33), CARTKQTARKSTG (SEQ ID NO: 34), CSGRGKGG (SEQ ID NO: 35) and CGLGKGGAKRHR (SEQ ID NO: 36). The crotonylation binding domain specifically binds to the peptide when the peptide is crotonylated at the crotonylation site, and does not bind to the peptide when the peptide is not crotonylated at the crotonylation site. The level of FRET indicates the level of protein crotonylation in the sample. The level of FRET may be increased or decreased after contacting. The method may further comprise adding an agent to the sample, and the agent regulates protein crotonylation. The agent may promote or inhibit protein crotonylation. The protein crotonylation may be histone crotonylation. A fusion protein reporter of the present invention may be used in this method.

In the method for determining the protein crotonylation level in a sample, the sample may be a biological sample. The biological sample may comprise a cell, a tissue biopsy, or a clinical fluid. The biological sample may be obtained from a subject (e.g., a mouse, rat, or human). The subject is healthy. The subject may have suffered from or may be predisposed to a histone crotonylation related disorder. A histone crotonylation related disorder refers to a disorder or disease linked to abnormal regulation of histone crotonylation. Examples of a histone crotonylation related disorder may include cancer, neurodegenerative diseases, aging, metabolic disorder, and dysgenesis. The method may further comprise comparing the FRET level in the sample with a control FRET level. The control FRET level may be the FRET level in a control sample obtained from a subject, and the subject has not suffered from or predisposed to a histone crotonylation related disorder. The FRET level in the sample may be higher or lower than the control FRET level.

A method for determining the level of protein de-crotonylation in a sample is provided. The method comprises (a) contacting the sample with a fusion protein reporter, and (b) comparing the level of fluorescence resonance energy transfer (FRET) between the donor fluorescent moiety and the acceptor fluorescent moiety after contacting with that before contacting. The fusion protein reporter comprises a core flanked by a donor fluorescent moiety and an acceptor fluorescent moiety. The core comprises a peptide comprising a crotonylation site that is crotonylated, and a crotonylation binding domain. The peptide is crotonylated at the crotonylation site. Examples of the crotonylated peptides include QLATKcrAA (SEQ ID NO: 11), CQLATKcrAA (SEQ ID NO: 12), YQKcrST (SEQ ID NO: 13), CYQKcrSTELL (SEQ ID NO: 14), LLPKKcrTESHHKAK (SEQ ID NO: 15), CLLPKKcrTESHHKAKG (SEQ ID NO: 16), APAPKcrKGS (SEQ ID NO: 17), APAPKcrKGSC (SEQ ID NO: 18), APAPKKcrGS (SEQ ID NO: 17), CAPAPKKcrGS (SEQ ID NO: 19), GSKKcrA (SEQ ID NO: 20), GSKKcrAVTC (SEQ ID NO: 21), TKcrAQKKDG (SEQ ID NO: 22), AVTKcrAQKKDGC (SEQ ID NO: 23), ARTKcrQTAR (SEQ ID NO: 24), ARTKcrQTARC (SEQ ID NO: 25), APRKcrQLA (SEQ ID NO: 26), APRKcrQLATC (SEQ ID NO: 27), QLATKcrAARK (SEQ ID NO: 28), QLATKcrAARKC (SEQ ID NO: 29), AARKcrSAP (SEQ ID NO: 30), AARKcrSAPATGGC (SEQ ID NO: 31), CRLLRKcrGNYAER (SEQ ID NO: 32), CLLPKcrTESHHKAKG (SEQ ID NO: 16), CLLPKK-TESHHKcrAKG (SEQ ID NO: 16), CAVTKAQKcrKDG (SEQ ID NO: 33), CARTKQTARKcrSTG (SEQ ID NO: 34), CSGRGKcrGG (SEQ ID NO: 35) and CGLGKGAKcrRHR (SEQ ID NO: 36). The crotonylation binding domain specifically binds to the peptide when the peptide is not crotonylated at the crotonylation site, and does not bind to the peptide when the peptide is crotonylated at the crotonylation site. The level of FRET indicates the level of protein de-crotonylation in the sample. The level of FRET may be increased or decreased after contacting. The method may further comprise adding an agent to the sample, and the agent regulates protein de-crotonylation. The agent may promote or inhibit protein crotonylation. Protein de-crotonylation may be histone de-crotonylation. A fusion protein reporter of the present invention may be used in this method.

In the method for determining the protein de-crotonylation level in a sample, the sample may be a biological sample. The biological sample may comprise a cell, a tissue biopsy, or a clinical fluid. The biological sample may be obtained from a subject (e.g., a mouse, rat or human). The subject is healthy. The subject may have suffered from or may be predisposed to a histone de-crotonylation related disorder. A histone de-crotonylation related disorder refers to a disorder or disease linked to abnormal regulation of histone crotonylation. Examples of a histone de-crotonylation related disorder may include cancer, neurodegenerative diseases, aging, metabolic disorder, and dysgenesis. The method may further comprise comparing the FRET level in the sample with a control FRET level. The control FRET level may be the FRET level in a control sample obtained from a subject, and the subject has not suffered from or predisposed to a histone de-crotonylation related disorder. The FRET level in the sample may be higher or lower than the control FRET level.

A method for screening an agent that regulates protein crotonylation is provided. The method comprises (a) contacting a candidate agent with a fusion protein reporter, and (b) comparing the level of fluorescence resonance energy transfer (FRET) between the donor fluorescent moiety and the acceptor fluorescent moiety after contacting with that before contacting. The fusion protein reporter comprises a core flanked by a donor fluorescent moiety and an acceptor fluorescent moiety. The core comprises a peptide comprising a crotonylation site, and a crotonylation binding domain. The peptide is not crotonylated at the crotonylation site. Examples of the non-crotonylated peptides include QLATKAA (SEQ ID NO: 11), CQLATKAA (SEQ ID NO: 12), YQKST (SEQ ID NO: 13), CYQKSTELL (SEQ ID NO: 14), LLPKKTESHHKAK (SEQ ID NO: 15), CLLPKKTESHHKAKG (SEQ ID NO: 16), APAPKKGS (SEQ ID NO: 17), APAPKKGSC (SEQ ID NO: 18), CAPAPKKGS (SEQ ID NO: 19), GSKKA (SEQ ID NO: 20), GSKKAVTC (SEQ ID NO: 21), TKAQKKDG (SEQ ID NO: 22), AVTKAQKKDGC (SEQ ID NO: 23), ARTKQTAR (SEQ ID NO: 24), ARTKQTARC (SEQ ID NO: 25), APRKQLA (SEQ ID NO: 26), APRKQLATC (SEQ ID NO: 27), QLATKAARK (SEQ ID NO: 28), QLATKAARKC (SEQ ID NO: 29), AARKSAP (SEQ ID NO: 30), AARKSAPATGGC (SEQ ID NO: 31), CRLLRKGNYAER (SEQ ID NO: 32), CAVTKAQKKDG (SEQ ID NO: 33), CARTKQTARKSTG (SEQ ID NO: 34), CSGRGKGG (SEQ ID NO: 35) and CGLGKGGAKRHR (SEQ ID NO: 36). The crotonylation binding domain specifically binds to the peptide when the peptide is crotonylated at the crotonylation site, and does not bind to the peptide when the peptide is not crotonylated at the crotonylation site. An increase in the level of FRET after contacting indicates that the candidate agent promotes protein crotonylation while a decrease in the level of FRET after contacting indicates that the candidate agent inhibits protein crotonylation. The candidate agent may be a compound or a biological molecule. The protein crotonylation may be histone crotonylation.

A method for screening an agent that regulates protein de-crotonylation is provided. The method comprises (a) contacting a candidate agent with a fusion protein reporter, and (b) comparing the level of fluorescence resonance energy transfer (FRET) between the donor fluorescent moiety and the acceptor fluorescent moiety after contacting with that before contacting. The fusion protein reporter comprises a core flanked by a donor fluorescent moiety and an acceptor fluorescent moiety. The core comprises a peptide comprising a crotonylation site that is crotonylated, and a crotonylation binding domain. The peptide is crotonylated at the crotonylation site. Examples of the crotonylated peptides include QLATKcrAA (SEQ ID NO: 11), CQLATKcrAA (SEQ ID NO: 12), YQKcrST (SEQ ID NO: 13), CYQKcrSTELL (SEQ ID NO: 14), LLPKKcrTESHHKAK (SEQ ID NO: 15), CLLPKKcrTESHHKAKG (SEQ ID NO: 16), APAPKcrKGS (SEQ ID NO: 17), APAPKcrKGSC (SEQ ID NO: 18), APAPKKcrGS (SEQ ID NO: 17), CAPAPKKcrGS (SEQ ID NO: 19), GSKKcrA (SEQ ID NO: 20), GSKKcrAVTC (SEQ ID NO: 21), TKcrAQKKDG (SEQ ID NO: 22), AVTKcrAQKKDGC (SEQ ID NO: 23), ARTKcrQTAR (SEQ ID NO: 24), ARTKcrQTARC (SEQ ID NO: 25), APRKcrQLA (SEQ ID NO: 26), APRKcrQLATC (SEQ ID NO: 27), QLATKcrAARK (SEQ ID NO: 28), QLATKcrAARKC (SEQ ID NO: 29), AARKcrSAP (SEQ ID NO: 30), AARKcrSAPATGGC (SEQ ID NO: 31), CRLLRKcrGNYAER (SEQ ID NO: 32), CLLPKcrTESHHKAKG (SEQ ID NO: 16), CLLPKK-TESHHKcrAKG (SEQ ID NO: 16), CAVTKAQKcrKDG (SEQ ID NO: 33), CARTKQTARKcrSTG (SEQ ID NO: 34), CSGRGKcrGG (SEQ ID NO: 35) and CGLGKGAKcrRHR (SEQ ID NO: 36). The crotonylation binding domain specifically binds to the peptide when the peptide is not crotonylated at the crotonylation site, and does not bind to the peptide when the peptide is crotonylated at the crotonylation site. An increase in the level of FRET after contacting indicates that the candidate agent promotes protein de-crotonylation while a decrease in the level of FRET after contacting indicates that the candidate agent inhibits protein de-crotonylation. The candidate agent may be a compound or a biological molecule. Protein de-crotonylation may be histone de-crotonylation.

A method for treating or preventing a protein crotonylation related disease in a subject in need thereof is provided. The method comprises administering to the subject an effective amount of a composition comprising an agent that regulates protein crotonylation. The agent may be identified by the screening method of the present invention. The protein crotonylation may be histone crotonylation.

A method for treating or preventing a protein de-crotonylation related disease in a subject in need thereof is provided. The method comprises administering to the subject an effective amount of a composition comprising an agent that regulates protein de-crotonylation. The agent may be identified by the screening method of the present invention. Protein de-crotonylation may be histone de-crotonylation.

EXAMPLE 1

Materials

All peptides used in this study were synthesized through customer synthesis using Fmoc-Lysine (crotonyl)-OH. All chemicals of the highest purity available or analytical grade and Flag M2 antibody were purchased from Sigma-Aldrich, Inc. (St. Louis, Mo.). HA antibody was purchased from Roche Diagnostics (Indianapolis, Ind.). The histones were extracted from *S. cerevisiae* cells, S2 cells, mouse embolic fibroblast (MEF) cells, human Caucasian fetal lung fibroblast (IMR90) cells, and HeLa cells using previously known procedures (Shechter et al., 2007; Tateishi et al., 2009). 4,4,4,3-D4-crotonic acid was prepared using D4-acetaldehyde (Cambridge Isotope Laboratories, Andover, Mass.) and malonic acid. Polyclonal pan anti-Kcr and anti-Kac antibodies were generated in house using a procedure described below.

Preparation of Histones from HeLa Cells

The process of preparing HeLa cell histones were known (Zhang et al., 2010). HeLa cells were grown in DMEM culture medium supplemented with 10% fetal bovine serum. The cells were then harvested and washed twice with ice-cold PBS containing 5 mM sodium butyrate. The cells were lysed in Triton extraction buffer (TEB; PBS containing 0.5% (v/v) Triton X-100, 2 mM PMSF, and 0.02% (w/v) NaN3). After centrifugation, the supernatant was removed. The pellet was washed, centrifuged, and resuspended in 0.4 N H2SO4 overnight at 4° C. After centrifugation, the supernatant was removed; histones in the supernatant were precipitated by the addition of 20% (v/v, final concentration) TCA to the protein solution. The suspension was incubated at −20° C. for 4 hrs. The protein precipitate was spun down, collected, and washed with acidified acetone (0.1% (v/v) HCl), followed by two washes with ice-cold acetone. After being dried at room temperature, the pellets were dissolved in water.

In-Solution Proteolytic Digestion and Chemical Derivatization of Histone Proteins In-solution tryptic digestion of histone samples was carried out using a known protocol (Kim et al., 2006; Luo et al., 2008). In vitro lysine propionylation of histone extract and tryptic histone peptides was performed as known in the art (Garcia et al., 2007a). Three different processes of proteolytic digestion were performed: histone extracts were (i) in-solution digested without chemical propionylation, (ii) chemically propionylated after in-solution digestion, or (iii) chemically propionylated before in-solution digestion.

Isoelectric Focusing (IEF) Fractionation

The histone proteolytic peptides were separated using an Agilent 3100 OFFGEL Fractionator (Agilent, Santa Clara, Calif.) according to the manufacturer's instructions and generally known in the art. Twelve fractions were obtained from each IEF fractionation experiment.

Synthesis of Bovine Serum Albumin (BSA) Derivatives

Five mg of but-3-enonylic acid, crotonic acid, or methacrylic acid was mixed with 5 mg of BSA in 4 ml of PBS buffer, followed by the addition of 25 mg of 1-ethyl-3-(3-dimethylaminopropyl) carbodiimide (EDC). The mixture was stirred at room temperature for 4 hrs to generate vinylacetyl-BSA, crotonyl-BSA, and methacryl-BSA, respectively. The unreacted EDC and other small molecules were removed from BSA derivatives by gel filtration. The modified BSAs were confirmed by SDS-PAGE.

Conjugation of Crotonyllysine-Immobilized Agarose Beads

The crotonyllysine residue was conjugated to AminoLink Plus Coupling Resin (Pierce Biotechnology, Rockford, Ill.) following the manufacturer's protocol. Two mL of resin were washed with PBS and then suspended in 6 mL PBS. The beads were then mixed with 2 mg of the crotonylysine (pre-solubilized in 2 ml PBS) and then NaCNBH3 (to a final concentration of 50 mM) was added. After incubation for 6 hrs at room temperature with agitation, the beads were washed by 4 ml of PBS and then blocked by 2 ml of 1.0 M Tris•HCl, pH 7.4 for 30 min at room temperature. The beads were sequentially washed with 10 mL of 1.0 M NaCl and 4 ml of PBS.

Generation of Pan Anti-Crotonyllysine Antibodies

The anti-crotonyllysine IgG was developed by immunizing 10 rabbits with lysine-crotonylated BSA. The rabbits were immunized with four injections. Five batches of serums were collected from each rabbit. The serum with the highest ELSA titer was used for enriching anti-crotonyllysine antibody.

The pan anti-crotonyllysine antibody was enriched using the crotonyllysine-conjugate agarose beads. About 10 mL of serum were incubated overnight with 2 mL of the crotonyllysine-conjugated agarose beads in a column. The beads were then sequentially washed with 20 mL of PBSN buffer (PBS containing 0.5% NP40), 20 mL of PBSS buffer (PBS containing 0.1% SDS), 6 mL of PBSS (PBS containing 0.8 M NaCl), and 6 mL of PBS. The bound antibodies were eluted from the beads with 0.1 M glycine (pH 3.0) and immediately neutralized with 1.0 M Tris-HCl (pH 8.5). The antibodies were dialyzed against in cold PBS overnight. Both dot-spot assay and Western blotting were performed to check quality of the antibody.

The pan anti-Kac antibodies were developed likewise using lysine-acetylated BSA as an antigen. The antibody was purified using acetyllysine-conjugated agarose by the above procedure.

FIG. 7 is the Western blot result showing the existence of lysine crotonylation in HeLa cell lysates with pan anti-Kcr antibody. HeLa cells were cultured in DMEM medium with/without crotonate (50 mM) for 12 hrs. Cells were lysed with sampling buffer. The protein from whole cell lysates were resolved on SDS-PAGE and Western blotting by anti-Kcr antibody.

Generation of Sequence-Specific Anti-Crotonyllysine Antibodies

As a particular embodiment, a sequence-specific anti-H3K23 crotonyllysine antibody (anti-H3K23cr rabbit pAb) was developed by immunizing rabbits with an antigen peptide bearing a crotonyllysine residue, CQLATKAA (SEQ ID NO: 12), where C is a cystein residue, and the underlined K indicates crotonyllysine residue. The rabbits were immunized with four injections. Five batches of serums were collected from each rabbit. The serum with the highest ELSA titer was used for enriching sequence-specific anti-crotonyllysine antibodies.

The sequence-specific anti-crotonyllysine antibodies was enriched using the antigen-conjugated agarose beads. The serums were centrifuged at 20,000 g to remove possible protein particles. About 10 mL of serum were incubated overnight with 2 mL of the crotonyllysine-containing peptide antigen conjugated agarose beads in a column. The beads were then sequentially washed with 20 mL of PBSN buffer (PBS containing 0.5% NP40), and 6 mL of PBS. The bound antibodies were eluted from the beads with 0.1 M glycine (pH 3.0) and immediately neutralized with 1.0 M Tris-HCl (pH 8.5). The antibodies were dialyzed against in cold PBS overnight. The obtained antibodies were depleted by incubating with the agarose conjugated with a peptide, CQLAT K AA (SEQ ID NO: 12), which has the same peptide sequence as the antigen peptide, but the lysine residue is not crotonylated. As it would be understood by a person with ordinary skill in the art, other antigen peptides other than the one used in this particular embodiment, i.e., CQLAT K AA (SEQ ID NO: 12), may also be used to obtain satisfactory results. The design of the antigen peptide is based on the sequence around a lysine in the protein whose crotonylation is intended as the target of detection and requires only ordinary kill in the art.

With the same method, another antigen peptide CYQ K STELL (SEQ ID NO: 14) (the underlined K is a lysine crotonylated), was used to generate sequence specific antibodies for H3K56 lysine crotonylation (anti-H3K56cr rabbit pAb). The processes are the same as described in the above except that an different antigen peptide (i.e., CYQ K STELL (SEQ ID NO: 14)) was used for targeting H3K56, that is, lysine crotonylation at position 56 of the H3 protein.

FIG. 8 shows the detection of H3K23 and H3K56 crotonylation by Western blotting using sequence-specific antibodies. Human HeLa histones were separated by SDS-PAGE and Western blotted by H3K23 crotonyllysine site specific antibody (anti-H3K23cr rabbit pAb) or H3K56 crotonyllysine site specific antibody (anti-H3K56cr rabbit pAb) competed by nonmodified (K) or crotonyllysine (Kcr) sequence specific peptide.

While in the above embodiments anti-crotonyllysine IgG was used, people with ordinary skill of the art may practice the present invention with corresponding monoclonal antibodies or single-chain variable fragments (scFvs) to obtain a satisfactory result.

Affinity enrichment of Crotonyllysine Peptides Using Anti-Kcr Antibody

The affinity-purified anti-crotonyllysine antibody was immobilized to protein A agarose beads (GE Healthcare Biosciences, Pittsburgh, Pa.) by incubation at 4° C. for 4 hrs. The supernatant was removed and the beads were washed three times with NETN buffer (50 mM Tris•HCl [pH 8.0], 100 mM NaCl, 1 mM EDTA, 0.5% NP40).

The histone tryptic peptides were resolubilized in NETN buffer. Affinity purification was carried out by incubating the peptides with 20 µl of anti-crotonyllysine antibody-immobilized protein A beads at 4° C. overnight with gentle shaking. The beads were washed three times with NETN buffer and twice with ETN buffer (50 mM Tris•HCl pH 8.0, 100 mM NaCl, 1 mM EDTA). The bound peptides were eluted from the beads by washing three times with 50 µl of 0.1% TFA. The elutes were combined and dried in SPEEDVAC.

Western Blotting with Competition with a Peptide Library

One µg of histone protein extracts were resolved in SDS-PAGE. Crotonylation signal was detected by pan anti-crotonyllysine antibody with competition by a peptide library bearing a non-modified, acetyl, propionyl, butyryl, methacrylyl, or crotonyl lysine.

In-Solution Proteolytic Digestion and Chemical Derivatization of Histone Proteins Histone tryptic peptides were generated by three methods: (i) Generation of histone peptides without in-vitro lysine propionylation. The histone pellet obtained above was suspended in 50 mM ammonium bicarbonate solution (pH 8.4) and was digested using a protocol previously described (Kim et al., 2006; Luo et al., 2008); (ii) In vitro lysine propionylation after histone tryptic digestion. The in vitro chemical reaction was performed as previously described (Garcia et al., 2007b). To generate derivatized histone peptides, 3 mg of histone tryptic digests obtained above were dissolved in 25 µl of 100 mM ammonium bicarbonate buffer (pH 8.0), and 600 µl of 50% propionic anhydride in methanol (v/v) was added into the solution. The pH of the solution was quickly adjusted to pH 8.0 with ammonium hydroxide. The mixture was then incubated at 51° C. for 20 min and dried in SPEEDVAC. The procedure was repeated once to ensure completion of the chemical reaction. (iii) In vitro lysine propionylation of core histones prior to tryptic digestion. Histones were derivatized by propionylation reaction as described above, and the derivatized histones were subjected to in-solution tryptic digestion overnight.

HPLC/MS/MS Analysis and Protein Sequence Database Searching

The dried peptide extracts were dissolved in 3 µl HPLC solvent A (0.1% formic acid in water, v/v). 1 µl sample was injected into a NanoLC-1D plus HPLC system (Eksigent Technologies, Dublin, Calif.), which was connected to a home-made capillary Jupiter C12 column (10 cm length×75 µm ID, 4 µm particle size, 90 Å pore size; Phenomenex, St. Torrance, Calif.). Peptides were eluted with a 2-hour gradient of 2% to 80% HPLC solvent B (0.1% formic acid in acetonitrile, v/v) in solvent A at a flow rate of 200 nl/min. Peptides were then ionized and analyzed by LTQ ORBITRAP Velos mass spectrometer (ThermoFisher Scientific, San Jose, Calif.) using a nano-spray source. High-resolution full scan MS spectra (from m/z 350-1400) were acquired in the ORBITRAP with resolution R=60,000 at m/z 400 and lockmass enabled (m/z at 445.120025), followed by MS/MS fragmentation of the twenty most intense ions in the linear ion trap with collisionally activated dissociation (CAD) energy of 35%. The exclusion duration for the data-dependent scan was 36 seconds, and the exclusion window was set at ±0.01% m/z.

The MS/MS data were analyzed by both non-restrictive sequence alignment by PTMap algorithm (Chen et al., 2009) and sequence alignment using limited, pre-specified PTMs by Mascot algorithm. The specific parameters for protein sequence database searching included lysine mono-, di- and tri-methylation, formylation and acetylation, arginine mono-methylation and di-methylation, tyrosine hydroxylation, methionine oxidation, and lysine crotonylation (K+68.02621 Da) as variable modifications for non-propionylated histones. For histone samples generated by tryptic digestion of propionylated histones, the specific parameters included lysine propionylmethylation (+70.04187 Da) and lysine propionylation as variable modifications. For histone samples propionylated after trypsin digestion, N-terminal propionylation was included as a fixed modification. Other parameters used in data analysis were: six allowed missing cleavages; mass error of 10 ppm for precursor ions, and 0.6 Da for fragment ions. Charge states of +1, +2, and +3 were considered for parent ions. If more than one spectrum was assigned to a peptide, only the spectrum with the highest Mascot or PTMap score was selected for manual analysis. All peptides identified with peptide scores of PTMap>0.8 and Mascot>20 were manually examined using rules known in the art (Chen et al., 2005).

Verification of Lysine Crotonylated Peptides by HPLC/MS/MS Analysis

The lysine crotonylated peptide in tryptic digest of histones, its synthetic counterpart, and their mixture were injected into nano-HPLC system and analyzed by high-resolution MS and MS/MS in the ORBITRAP mass spectrometer, respectively. Full MS scans were acquired with resolution R=30,000 at m/z 400 with lockmass enabled (m/z at 445.120025), and targeted MS/MS spectra were acquired at a resolution of 7,500 at m/z 400.

Identification of Kcr Peptides

Histone proteins have a high ratio of both lysine and arginine residues. Thus, many histone tryptic peptides are relatively small and hydrophilic, some of which cannot be retained in a C18 RP-HPLC column for subsequent detection by MS. This problem can be addressed by chemical derivatization (e.g., lysine propionylation) of amine groups in the protein (N-terminal amines, and free and monomethylated lysine ε-amino groups) before or after tryptic digestion. Similarly, lysine propionylation of core histones, before or after tryptic digestion, will generate complementary peptide sequences that boost the sequence coverage of peptide mapping by MS. Additionally, IEF separation of tryptic digest into 12 fractions will further reduce peptide complexity and improve dynamic range.

Figure 1:
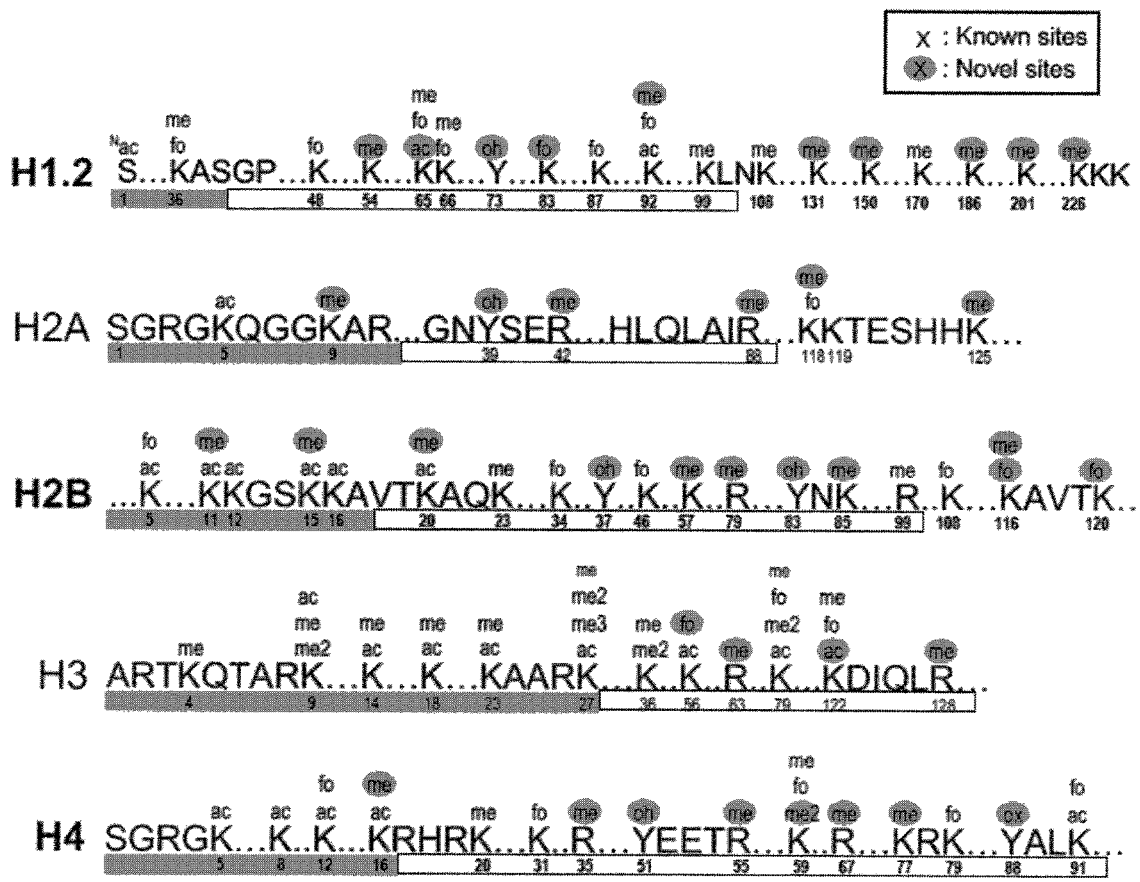
FIG. 1 summarizes an experimental strategy and results for identifying histone PTM sites according to some embodiments of the present invention. (A) A schematic diagram illustrating the experimental design for comprehensive mapping of PTM sites in linker and core histones from HeLa cells using Methods I, II, III or IV. (B) Peptide sequence coverage of linker and core histones in Methods I, II, III or IV. (C) A summary of the identified PTM sites. Abbreviations: Kme, lysine monomethylation; Kme2, lysine dimethylation; Kfo, lysine formylation; Kac, lysine acetylation; Rme, arginine monomethylation; Yoh, tyrosine hydroxylation; and Kcr, lysine crotonylation. (D) A diagram showing the identified sites of histone PTMs other than lysine crotonylation (Kcr) in human histone proteins H1.2 (SEQ ID NO: 1), H2A (SEQ ID NO: 2), H2B (SEQ ID NO: 3), H3 (SEQ ID NO: 4) and H4 (SEQ ID NO: 5). Amino acid residue number is indicated below its sequence. Gray and blank boxes indicate N-terminal and globular core domains, respectively. (E) Illustrations of histone Kcr sites in human HeLa cells (H2A (SEQ ID NO: 2), H2B (SEQ ID NO: 3), H3 (SEQ ID NO: 4), H4 (SEQ ID NO: 5), and H1.2 (SEQ ID NO: 1)) and mouse MEF cells (H2A (SEQ ID NO: 7), H2B (SEQ ID NO: 8), H3 (SEQ ID NO: 9), H4 (SEQ ID NO: 10), and H1.2 (SEQ ID NO: 6)). All newly discovered Kcr sites are shown underlined. Previously reported lysine acetylation (Kac) sites are also shown.

In the present invention, as a particular embodiment, the integrated approach was designed for systematic analysis of histone PTMs (i.e., post-translational modifications). The strategy and results for identifying histone PTM sites are shown in FIG. 1, which represented an effort to maximize both the sequence coverage and sensitivity, and to identify novel PTM sites. In this invention, MS analysis was carried out in histone proteolytic peptides that were generated by four parallel methods (see FIG. 1A): Histone extracts were in-solution tryptic digestion without chemical propionylation (Method I), chemically propionylated after in-solution tryptic digestion (Method II), chemically propionylated before in-solution tryptic digestion (Method III), and in-gel digested after SDS-PAGE gel separation. Samples from Methods I and II were further subjected to IEF fractionation to generate 12 fractions. FIG. 1B shows peptide sequence coverage of linker and core histones detected by the four methods. The PTM sites identified in the work as a particular embodiment of the invention are summarized in FIG. 1C, where abbreviations are Kme for lysine monomethylation; Kme2 for lysine dimethylation; Kfo for lysine formylation; Kac for lysine acetylation; Rme for arginine monomethylation; Yoh for tyrosine hydroxylation; and Kcr for lysine crotonylation PTMap, an algorithm capable of identifying all possible PTMs of a protein (Chen et al., 2009), was used to analyze all the acquired MS/MS data to identify histone peptides with or without a PTM. As anticipated, sequence coverage by MS mapping was significantly improved after in vitro propionylation, either before or after tryptic digestion (see FIG. 1B). Among the four methods, Method III (in vitro propionylation before tryptic digestion of histones) achieved the highest sequence coverage of histones H1.2 (100%), H2A (90.7%) and H2B (94.4%). Method IV gave the best coverage for histones H3 (87.3%) and H4 (82.3%). In aggregate, we achieved sequence coverage of 100% of H1.2, 90.7% of H2A, 100% of H2B, 91% of H3, and 87.3% of H4. To our knowledge, this represents the highest reported sequence coverage for peptide mapping in histones.

Using this approach, 130 unique PTM sites, including 28 Kcr sites (crotonylated lysine residue) were identified in the present invention. The remaining 102 non-Kcr modifications consist of 39 novel PTM sites, including 18 lysine monomethylation (Kme) sites, 1 lysine dimethylation (Kme2) site, 4 lysine formylation (Kfo) sites, 2 lysine acetylation (Kac) sites, 8 arginine monomethylation (Rme) sites and 6 tyrosine hydroxylation (Yoh) sites (see FIG. 1C).

A summary of the non-Kcr modification sites and Kcr sites identified in this study are shown in FIGS. 1D and 1E (where Kcr sites are underlined), respectively. All the MS/MS spectra for the identified histone PTM peptides were carefully verified as previously reported (Chen et al., 2005). It is confirmed the identification of Kcr peptides and 10 novel non-Kcr PTM sites by MS/MS of their corresponding synthetic peptides or by high-resolution MS/MS.

Identification of Kcr Residues in Histones

A PTM will induce structural and compositional changes in the substrate residue and therefore a change of its molecular weight. In the present invention, the analysis identified, on 28 lysine residues of the core histone peptides, a mass shift of +68 Da, which does not match the shift associated with any known PTM (see FIG. 1E), indicating a possible histone mark unknown previously.

To reveal the structure of this modification, one of these peptides, PEPAK+68SAPAPK (SEQ ID NO: 44) (modified at H2BK5), was selected for further analysis. After manual inspection of the high-resolution MS data (precursor ion mass at m/z 580.8181) of this peptide, we determined the accurate mass shift of this modification as +68.0230 Da. By setting the mass tolerance to ±0.01 Da (~9 ppm, which is within the mass accuracy of the mass spectrometer used), and specifying a maximum of 2 nitrogen atoms, it was deduced, based on the mass shift, that the possible element compositions of the modification group as either C4H4O or H6NO3. The former, C4H5O (mass shift plus one proton), is the only reasonable molecular formula of this modification. There were 4 possible structures consistent with the element composition: Kcr (FIGS. 2A and 2B), vinylacetyllysine (3-butenoyllysine), methacryllysine, and cyclopropanecarboxyllysine (FIG. 2C). As crotonyl-CoA is an important and abundant intermediate (FIG. 2D), in metabolic pathways of butyryl-CoA and acetyl-CoA, Kcr was considered as a putative PTM candidate. FIG. 2A shows the chemical structures and an illustration of the enzymatic reactions for lysine acetylation by lysine acetyltransferases (KATs) using acetyl-CoA as a cofactor and the hypothesized mechanism for Kcr using crotonyl-CoA as a cofactor. In FIG. 2B, the ball-and-stick models of a crotonyl group and an acetyl group are shown. The three-dimensional arrangement of four carbons and one oxygen of the crotonyl group that are rigid and is located in the same plane (left). The two olefinic carbons of the crotonyl group are shown in the middle. In contrast, the tetrahedral CH3 in the acetyl group (right) can be rotated that is structurally very different from the crotonyl group.

MS/MS of Synthetic Peptides and HPLC Coelution

To test if the identified mass shift of +68.0230 Da was caused by Kcr, we synthesized the Kcr peptide, PEPAKcrSAPAPK (SEQ ID NO: 44), and compared its MS/MS spectrum with that of the in vivo-derived peptide. The in vivo modified peptide bearing a lysine residue with a mass shift of +68.0230 Da, the synthetic Kcr peptide with the same peptide sequence (PEPAKcrSAPAPK) (SEQ ID NO: 44), and the mixture of the two peptides exhibited almost identical parent masses and high-resolution MS/MS spectra (FIGS. 3A to 3C). In addition, the mixture of the in vivo and synthetic peptides coeluted in HPLC/MS analysis (FIG. 3D). These results indicated that the identified mass shift of +68.0230 Da was very likely caused by Kcr.

Confirmation of Kcr Proteins by Western Blotting and Immunostaining

To further confirm Kcr in histones, a pan antibody was generated against Kcr. This pan anti-Kcr antibody specifically recognized a peptide library bearing Kcr, but not four other peptide libraries in which the fixed lysine residue was unmodified (K), acetylated(Kac), propionylated(Kpr), or butyrylated(Kbu) (FIG. 4A). The specificity of the pan anti-Kcr antibody was also shown by Western blotting with three bovine serum albumin (BSA) derivatives, whose lysines were chemically modified by a crotonyl, vinylacetyl or methacryl group, respectively. The result showed that pan anti-Kcr antibody only recognized the lysine crotonylated BSA, but not the unmodified, lysine vinylacetylated or lysine methacrylated BSA (FIG. 4B). This pan anti-Kcr antibody was used for Western blotting and immunostaining of Kcr signal.

The antibody could detect a Kcr signal among all core histone proteins, H2A, H2B, H3, H4, and linker histone H1. In each protein, the signal could be efficiently competed away by a peptide library bearing a Kcr, but not the peptide library bearing an unmodified lysine (FIG. 4C), metharcryllysine (FIG. 4C), acetyllysine, propionyllysine, or butyryllysine (FIG. 4D).

By independent confirmation based on five different methods, MS/MS and HPLC coelution of synthetic peptides, D4-crotonate labeling, Western blotting, and immunostaining, the present invention conclusively verified the existence of histone Kcr.

Confirmation of Kcr Proteins by In Vivo D4-Crotonate Isotopic Labeling

FIG. 5A shows the dynamics of histone Kcr in response to crotonate. The histone proteins extracted from human prostate cancer cell line Du145 incubated with 0, 50 or 100 mM crotonate for 24 hrs, were Western blotted with anti-Kcr pan antibody. FIG. 5B shows MS/MS spectrum of PEPAK$_{D4}$crSAPAPK (SEQ ID NO: 44) identified from D4-crotonate-labeled sample. The mixture of D4-, D3- and D2-crotonyl groups was used for the identification of D4-crotonyl peptide.

Detection of Histone Kcr as in Different Cell Types

Using the method of the present invention, it is further verified that lysine crotonylation is present in histones from other eukaryotic cells. For example, Kcr signals were detected among core histones in samples from yeast S. cerevisiae, Drosophila S2 cells, mouse embryonic fibroblast (MEF) cells, as well as human HeLa cells (FIG. 6). Taking advantage of affinity enrichment using the pan anti-Kcr antibody and HPLC/MS/MS, 24 Kcr sites were identified on mouse MEF cells. The results, therefore, revealed that Kcr is an evolutionarily conserved histone mark in eukaryotic cells.

The present invention provides an integrated approach for the systematic analysis of histone PTMs. With this unique approach, 130 PTM sites on human histones, including 63 known and 67 novel histone marks were identified as a particular embodiment of the invention, in which Yoh and Kcr were identified as two novel types of histone PTM. Therefore, the present invention has extended the catalogue of histone PTM sites in mammalian cells and provides a platform for the discovery of novel mechanisms of histone regulation and new ways of treating diseases related to histone regulation.

EXAMPLE 2

Synthetic crotonylated peptides have been designed as peptide antigens to produce histone crotonylation site specific antibodies that specifically recognize histone proteins when crotonylated at specific crotonylation sites. The synthetic crotonylated peptide may have a sequence selected from SEQ ID NOs: 11-43, and may have modifications on adjacent residues as shown in Table 2. Where an adjacent residue is modified, such modification is protected. Analysis of some exemplary histone crotonylation site specific antibodies is described below.

Anti-crotonyl-histone H2A (Lys119) rabbit pAb was produced by immunizing rabbits with a synthetic crotonyl peptide, CLLPKKcrTESHHKAKG (SEQ ID NO: 16), corresponding to residues surrounding Lys119 of human histone H2A. The antibody was purified by protein A-conjugated agarose followed by crotonylated histone H2A (Lys119) peptide affinity chromatography. This antibody detects histone H2A only when it is crotonylated at Lys119, and selectively recognizes crotonylated H2A peptide at Lys119, but not the crotonylated H2A peptide at Lys118 or the unmodified peptide (FIG. 11A).

Anti-crotonyl-histone H2B (Lys11) rabbit pAb was produced by immunizing rabbits with a synthetic crotonyl peptide, APAPKcrKGSC (SEQ ID NO: 18), corresponding to residues surrounding Lys11 of human histone H2B. The antibody was purified by protein A-conjugated agarose followed by crotonylated histone H2B (Lys11) peptide affinity chromatography. This antibody detects histone H2B only when it is crotonylated at Lys11, and selectively recognizes crotonylated H2B peptide at Lys11, but not the crotonylated H2B peptide at Lys12 or the unmodified peptide (FIG. 12A).

Anti-crotonyl-histone H2B (Lys12) rabbit pAb was produced by immunizing rabbits with a synthetic crotonyl peptide, CAPAPKKcrGS (SEQ ID NO: 19), corresponding to residues surrounding Lys12 of human histone H2B. The antibody was purified by protein A-conjugated agarose followed by crotonylated histone H2B (Lys12) peptide affinity chromatography. This antibody detects histone H2B only when it is crotonylated at Lys12, and selectively recognizes crotonylated H2B peptide at Lys12, but not the crotonylated H2B peptide at Lys11 or the unmodified peptide (FIG. 13A).

Anti-crotonyl-histone H2B (Lys16) rabbit pAb was produced by immunizing rabbits with a synthetic crotonyl peptide, GSKKcrAVTC (SEQ ID NO: 21), corresponding to residues surrounding Lys16 of human histone H2B. The antibody was purified by protein A-conjugated agarose followed by crotonylated histone H2B (Lys16) peptide affinity chromatography. This antibody detects histone H2B only when it is crotonylated at Lys16, and selectively recognizes crotonylated H2B peptide at Lys16, but not the unmodified peptide (FIG. 14A).

Anti-crotonyl-histone H2B (Lys20) rabbit pAb was produced by immunizing rabbits with a synthetic crotonyl peptide, AVTKcrAQKKDGC (SEQ ID NO: 23), corresponding to residues surrounding Lys20 of human histone H2B. The antibody was purified by protein A-conjugated agarose followed by crotonylated histone H2B (Lys20) peptide affinity chromatography. This antibody detects histone H2B only when it is crotonylated at Lys20, and selectively recognize crotonylated H2B peptide at Lys20, but with little cross-reaction to the butyrylated H2B peptide at Lys20, crotonylated H2B peptide at Lys 23 and the unmodified peptide (FIG. 15A).

Anti-crotonyl-histone H2B (Lys34) rabbit pAb was produced by immunizing rabbits with a synthetic crotonyl peptide, CRSRKcrESY (SEQ ID NO: 46), corresponding to residues surrounding Lys34 of human histone H2B. The antibody was purified by protein A-conjugated agarose followed by crotonylated histone H2B (Lys34) peptide affinity chromatography. This antibody detects histone H2B only when it is crotonylated at Lys34, and selectively recognize crotonylated H2B peptide at Lys34, but not the succinylated H2B peptide at Lys34 and the unmodified peptide (FIG. 16A).

Anti-crotonyl-histone H3 (Lys4) rabbit pAb was produced by immunizing rabbits with a synthetic crotonyl peptide, ARTKcrQTARC (SEQ ID NO: 25), corresponding to residues surrounding Lys4 of human histone H3. The antibody was purified by protein A-conjugated agarose followed by crotonylated histone H3 (Lys4) peptide affinity chromatography. This antibody detects histone H3 only when it is crotonylated at Lys4, and selectively recognizes crotonylated H3 peptide at Lys4, but not the crotonylated or butyrylated H3 peptide at Lys9 or the unmodified peptide (FIG. 17A).

Anti-crotonyl-histone H3 (Lys4) mouse mAb was produced by immunizing mice with a synthetic crotonyl peptide, ARTKcrQTARC (SEQ ID NO: 25), corresponding to residues surrounding Lys4 of human histone H3. The antibody was purified by protein G-conjugated agarose followed by crotonylated histone H3 (Lys4) peptide affinity chromatography. This antibody detects histone H3 only when it is crotonylated at Lys4, and selectively recognizes crotonylated H3 peptide at Lys4, but not the crotonylated or butyrylated H3 peptide at Lys9 or the unmodified peptide (FIG. 18A).

Anti-crotonyl-histone H3 (Lys18) rabbit pAb was produced by immunizing rabbit with a synthetic crotonyl peptide, APRKcrQLATC (SEQ ID NO: 27), corresponding to residues surrounding Lys18 of human histone H3. The antibody was purified by protein A-conjugated agarose followed by crotonylated histone H3 (Lys18) peptide affinity chromatography. This antibody detects histone H3 only when it is crotonylated at Lys18, and selectively recognizes crotonylated H3 peptide at Lys18, but not the unmodified peptide or the structurally similar butyrylated or propionylated H3 peptide at Lys18 (FIG. 19A).

Anti-crotonyl-histone H3 (Lys23) mouse mAb was produced by immunizing mice with a synthetic crotonyl peptide, QLATKcrAARKC (SEQ ID NO: 29), corresponding to residues surrounding Lys23 of human histone H3. The antibody was purified by protein G-conjugated agarose followed by crotonylated histone H3 (Lys23) peptide affinity chromatography. This antibody detects histone H3 only when it is crotonylated at Lys23, and selectively recognizes crotonylated H3 peptide at Lys23, but not the structurally similar acetylated, propionylated or butyrylated H3 peptide at Lys23 (FIG. 20A).

Anti-crotonyl-histone H3 (Lys23) rabbit pAb was produced by immunizing rabbits with a synthetic crotonyl peptide, QLATKcrAARKC (SEQ ID NO: 29), corresponding to residues surrounding Lys23 of human histone H3. Antibodies are purified by protein A-conjugated agarose followed by crotonylated histone H3 (Lys23) peptide affinity chromatography. The antibody was purified with protein A-conjugated agarose followed by crotonylated histone H3 (Lys23) peptide affinity chromatography. This antibody detects histone H3 only when it is crotonylated at Lys23, and selectively recognizes crotonylated H3 peptide at Lys23, but not the unmodified peptide and the structurally similar butyrylated or propionylated H3 peptide at Lys23 (FIG. 21A).

Anti-crotonyl-histone H3 (Lys27) mouse mAb was produced by immunizing mice with a synthetic crotonyl peptide, AARKcrSAPATGGC (SEQ ID NO; 31), corresponding to residues surrounding Lys27 of human histone H3. The antibody was purified with protein G-conjugated agarose followed by crotonylated histone H3 (Lys27) peptide affinity chromatography. This antibody detects histone H3 only when it is crotonylated at Lys27, and selectively recognizes crotonylated H3 peptide at Lys27, but not the structurally similar acetylated peptide at Lys27 or the unmodified peptide (FIG. 22A).

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate.

All documents, books, manuals, papers, patents, published patent applications, guides, abstracts, and other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

REFERENCES

Chen, Y., Chen, W., Cobb, M. H., and Zhao, Y. (2009). PTMap—a sequence alignment software for unrestricted, accurate, and full-spectrum identification of post-translational modification sites. Proc Natl Acad Sci USA 106, 761-766.

Chen, Y., Kwon, S. W., Kim, S. C., and. Zhao, Y. (2005). Integrated approach for manual evaluation of peptides identified by searching protein sequence databases with tandem mass spectra. J Proteome Res 4, 998-1005.

Chu, F., Nusinow, D. A., Chalkley, R. J., Plath, K., Panning, B., and Burlingame, A. L. (2006). Mapping post-translational modifications of the histone variant MacroH2A1 using tandem mass spectrometry. Mol Cell Proteomics 5, 194-203.

Cosgrove, M. S., Boeke, J. D., and Wolberger, C. (2004). Regulated nucleosome mobility and the histone code. Nat Struct Mol Biol 11, 1037-1043.

Garcia, B. A., Mollah, S., Ueberheide, B. M., Busby, S. A., Muratore, T. L., Shabanowitz, J., and Hunt, D. F. (2007a). Chemical derivatization of histones for facilitated analysis by mass spectrometry. Nat Protoc 2, 933-938.

Garcia, B. A., Pesavento, J. J., Mizzen, C. A., and Kelleher, N. L. (2007b). Pervasive combinatorial modification of histone H3 in human cells. Nat Methods 4, 487-489.

Garcia, B. A., Shabanowitz, J., and Hunt, D. F. (2007c). Characterization of histones and their post-translational modifications by mass spectrometry. Curr Opin Chem Biol 11, 66-73.

Johnson, L., Mollah, S., Garcia, B. A., Muratore, T. L., Shabanowitz, J., Hunt, D. F., and Jacobsen, S. E. (2004). Mass spectrometry analysis of Arabidopsis histone H3 reveals distinct combinations of post-translational modifications. Nucleic Acids Res 32, 6511-6518.

Kim, S. C., Sprung, R., Chen, Y., Xu, Y., Ball, H., Pei, J., Cheng, T., Kho, Y., Xiao, H., Xiao, L., et al. (2006). Substrate and functional diversity of lysine acetylation revealed by a proteomics survey. Mol Cell 23, 607-618.

Kouzarides, T. (2007). Chromatin modifications and their function. Cell 128, 693-705. Luo, H., Li, Y., Mu, J. J., Zhang, J., Tonaka, T., Hamamori, Y., Jung, S. Y., Wang, Y., and Qin, J. (2008). Regulation of intra-S phase checkpoint by ionizing radiation (IR)-dependent and IR-independent phosphorylation of SMC3. J Biol Chem 283, 19176-19183.

Margueron, R., Trojer, P., and Reinberg, D. (2005). The key to development: interpreting the histone code? Curr Opin Genet Dev 15, 163-176.

Martin, C., and Zhang, Y. (2007). Mechanisms of epigenetic inheritance. Curr Opin Cell Biol 19, 266-272.
Mersfelder, E. L., and Parthun, M. R. (2006). The tale beyond the tail: histone core domain modifications and the regulation of chromatin structure. Nucleic Acids Res 34, 2653-2662.
Ruthenburg, A. J., Li, H., Patel, D. J., and Allis, C. D. (2007). Multivalent engagement of chromatin modifications by linked binding modules. Nat Rev Mol Cell Biol 8, 983-994.
Sakabe, K., Wang, Z., and Hart, G. W. (2010). Beta-N-acetylglucosamine (O-GlcNAc) is part of the histone code. Proc Natl Acad Sci USA 107, 19915-19920.
Shechter, D., Dormann, H. L., Allis, C. D., and Hake, S. B. (2007). Extraction, purification and analysis of histones. Nat Protoc 2, 1445-1457.
Tateishi, K., Okada, Y., Kallin, E. M., and Zhang, Y. (2009). Role of Jhdm2a in regulating metabolic gene expression and obesity resistance. Nature 458, 757-761.
Wisniewski, J. R., Zougman, A., Kruger, S., and Mann, M. (2007). Mass spectrometric mapping of linker histone H1 variants reveals multiple acetylations, methylations, and phosphorylation as well as differences between cell culture and tissue. Mol Cell Proteomics 6, 72-87.
Wysocka, J., Swigut, T., Milne, T. A., Dou, Y., Zhang, X., Burlingame, A. L., Roeder, R. G., Brivanlou, A. H., and Allis, C. D. (2005). WDR5 associates with histone H3 methylated at K4 and is essential for H3 K4 methylation and vertebrate development. Cell 121, 859-872.
Wysocka, J., Swigut, T., Xiao, H., Milne, T. A., Kwon, S. Y., Landry, J., Kauer, M., Tackett, A. J., Chait, B. T., Badenhorst, P., et al. (2006). A PHD finger of NURF couples histone H3 lysine 4 trimethylation with chromatin remodelling. Nature 442, 86-90.
Zee, B. M., Levin, R. S., Xu, B., LeRoy, G., Wingreen, N. S., and Garcia, B. A. (2010). In vivo residue-specific histone methylation dynamics. J Biol Chem 285, 3341-3350.
Zeng, L., and Zhou, M. M. (2002). Bromodomain: an acetyl-lysine binding domain. FEBS Lett 513, 124-128.
Zhang, J., Chen, Y., Zhang, Z., Xing, G., Wysocka, J., and Zhao, Y. (2010). MS/MS/MS reveals false positive identification of histone serine methylation. J Proteome Res 9, 585-594.

TABLE 1

List of Histone Peptides

| Peptide Sequence | SEQ ID NO | Crotonylated Peptide | Crotonylation Site |
|---|---|---|---|
| QLATKAA | 11 | QLATKcrAA | H3K23 |
| CQLATKAA | 12 | CQLATKcrAA | H3K23 |
| YQKST | 13 | YQKcrST | H3K56 |
| CYQKSTELL | 14 | CYQKcrSTELL | H3K56 |
| LLPKKTESHHKAK | 15 | LLPKKcrTESHEIKAK | H2AK119 |
| CLLPKKTESHHKAKG | 16 | CLLPKKcrTESHHKAKG | H2AK119 |
| APAPKKGS | 17 | APAPKcrKGS | H2BK11 |
| APAPKKGSC | 18 | APAPKcrKGSC | H2BK11 |
| APAPKKGS | 17 | APAPKKcrGS | H2BK12 |
| CAPAPKKGS | 19 | CAPAPKKcrGS | H2BK12 |

TABLE 1-continued

List of Histone Peptides

| Peptide Sequence | SEQ ID NO | Crotonylated Peptide | Crotonylation Site |
|---|---|---|---|
| GSKKA | 20 | GSKKcrA | H2BK16 |
| GSKKAVTC | 21 | GSKKcrAVTC | H2BK16 |
| TKAQKKDG | 22 | TKcrAQKKDG | H2BK20 |
| AVTKAQKKDGC | 23 | AVTKcrAQKKDGC | H2BK20 |
| ARTKQTAR | 24 | ARTKcrQTAR | H3K4 |
| ARTKQTARC | 25 | ARTKcrQTARC | H3K4 |
| APRKQLA | 26 | APRKcrQLA | H3K18 |
| APRKQLATC | 27 | APRKcrQLATC | H3K18 |
| QLATKAARK | 28 | QLATKcrAARK | H3K23 |
| QLATKAARKC | 29 | QLATKcrAARKC | H3K23 |
| AARKSAP | 30 | AARKcrSAP | H3K27 |
| AARKSAPATGGC | 31 | AARKcrSAPATGGC | H3K27 |
| CRLLRKGNYAER | 32 | CRLLRKcrGNYAER | H2AK36 |
| CLLPKKTESHITKAKG | 16 | CLLPKcrKTESHHKAKG | H2AK118 |
| CLLPKKTESHHKAKG | 16 | CLLPKKTESHHKcrAKG | H2AK125 |
| CAVTKAQKKDG | 33 | CAVTKAQKcrKDG | H2BK23 |
| CARTKQTARKSTG | 34 | CARTKQTARKcrSTG | H3K9 |
| CSGRGKGG | 35 | CSGRG<u>Kcr</u>GG | H4K5 |
| CGLGKGGAKRHR | 36 | CGLGKGGAKcrRHR | H4K16 |
| CGTPRKASGP | 37 | CGTPRKcrASGP | H1K34 |
| LKKALAAAGYC | 38 | LKKcrALAAAGYC | H1K64 |
| CKLGLKSLVSK | 39 | CKLGLKcrSLVSK | H1K85 |
| CKSLVSKGTL | 40 | CKSLVSKcrGTL | H1K90 |
| CVQTKGTGA | 41 | CVQTKcrGTGA | H1K97 |
| CTPKKAKKPA | 42 | CTPKKAKcrKPA | H1K159 |
| VTKKVAKSPKC | 43 | VTKcrKVAKSPKC | H1K168 |
| CRSRKESY | 46 | CRSRKcrESY | H2BK34 |
| GGKGLGKC | 47 | GG<u>Kcr</u>GLGKC | H4K8 |

TABLE 2

Modifications on Adjacent Residues of Histone Kcr Peptides

| Peptide Sequence | SEQ ID NO | Crotonylated Peptide | Crotonylation Site | Peptide sequence | PTM site |
|---|---|---|---|---|---|
| CRLLRKGNYAER | 32 | CRLLRKcrGNYAER | H2AK36 | CRLLRKGNYoxAER | H2AY39 |
| CLLPKKTESHHKAKG | 16 | CLLPKcrKTESHHKAKG | H2AK118 | CLLPKKTphoESHHKAKG | H2AT120 |
| CLLPKKTESHHKAKG | 16 | CLLPKKcrTESHHKAKG | H2AK119 | | |
| CLLPKKTESHHKAKG | 16 | CLLPKKTESHHKcrAKG | H2AK125 | | |
| APAPKKGSC | 18 | APAPKcrKGSC | H2BK11 | APAPKKGSphoC | H2BS14 |
| CAPAPKKGS | 19 | CAPAPKKcrGS | H2BK12 | | |
| GSKKAVTC | 21 | GSKKcrAVTC | H2BK16 | GSK(me, ac)KAVTC | H2BK15 |
| AVTKAQKKDGC | 23 | AVTKcrAQKKDGC | H2BK20 | AVTKAQKKacDGC | H2BK24 |
| CAVTKAQKKDG | 33 | CAVTKAQKcrKDG | H2BK23 | | |
| CRSRKESY | 46 | CRSRKcrESY | H2BK34 | CRSphoRKcrESphoYox | H2BK32, 36, 37 |
| ARTKQTARC | 25 | ARTKcrQTARC | H3K4 | ARTphoKQTARmeC | H3K3, 8 |
| CARTKQTARKSTG | 34 | CARTKQTARKcrSTG | H3K9 | CARTKQTARKSphoTphoG | H3K10, 11 |
| APRKQLATC | 27 | APRKcrQLATC | H3K18 | APRmeKQLATC | H3K17 |
| QLATKAARKC | 29 | QLATKcrAARKC | H3K23 | QLATKAARmeKC | H3K26 |
| AARKSAPATGGC | 31 | AARKcrSAPATGGC | H3K27 | AARKKSphoAPATGGC | H3K28 |
| CYQKSTELL | 14 | CYQKcrSTELL | H3K56 | | |
| CSGRGKGG | 35 | CSGRGKcrGG | H4K5 | CSphoGRmeGKGG | H4K1, 3 |
| GGKGLGKC | 47 | GGKcrGLGKC | H4K8 | GGKGLGK(succ, pro, bu, ac me)C | H4K12 |
| CGLGKGGAKRHR | 36 | CGLGKGGAKcrRHR | H4K16 | | |
| CRLLRKGNYAER | 32 | CRLLRKcrGNYAER | H2AK36 | CRLLRKGNYoxAER | H2AY39 |
| CLLPKKTESHHKAKG | 16 | CLLPKcrKTESHHKAKG | H2AK118 | CLLPKKTphoESHHKAKG | H2AT120 |
| CLLPKKTESHHKAKG | 16 | CLLPKKcrTESHHKAKG | H2AK119 | | |
| CLLPKKTESHHKAKG | 16 | CLLPKKTESHHKcrAKG | H2AK125 | | |
| APAPKKGSC | 18 | APAPKcrKGSC | H2BK11 | APAPKKGSphoC | H2BS14 |
| CAPAPKKGS | 19 | CAPAPKKcrGS | H2BK12 | | |
| GSKKAVTC | 21 | GSKKcrAVTC | H2BK16 | GSK(me, ac)KAVTC | H2BK15 |
| AVTKAQKKDGC | 23 | AVTKcrAQKKDGC | H2BK20 | AVTKAQKKacDGC | H2BK24 |
| CAVTKAQKKDG | 33 | CAVTKAQKcrKDG | H2BK23 | | |
| CRSRKESY | 46 | CRSRKcrESY | H2BK34 | CRSphoRKcrESphoYox | H2BK32, 36, 37 |
| ARTKQTARC | 25 | ARTKcrQTARC | H3K4 | ARTphoKQTARmeC | H3K3, 8 |
| CARTKQTARKSTG | 34 | CARTKQTARKcrSTG | H3K9 | CARTKQTARKSphoTphoG | H3K10, 11 |
| APRKQLATC | 27 | APRKcrQLATC | H3K18 | APRmeKQLATC | H3K17 |
| QLATKAARKC | 29 | QLATKcrAARKC | H3K23 | QLATKAARmeKC | H3K26 |
| AARKSAPATGGC | 31 | AARKcrSAPATGGC | H3K27 | AARKKSphoAPATGGC | H3K28 |
| CYQKSTELL | 14 | CYQKcrSTELL | H3K56 | | |
| CSGRGKGG | 35 | CSGRGKcrGG | H4K5 | CSphoGRmeGKGG | H4K1, 3 |
| GGKGLGKC | 47 | GGKcrGLGKC | H4K8 | GGKGLGK(succ, pro, bu, ac me)C | H4K12 |

TABLE 2-continued

Modifications on Adjacent Residues of Histone Kcr Peptides

| Peptide Sequence | SEQ ID NO | Crotonylated Peptide | Crotonylation Site | Peptide sequence | PTM site |
|---|---|---|---|---|---|
| CGLGKGGAKRHR | 36 | CGLGKGGAKcrRHR | H4K16 | | |
| CGTPRKASGP | 37 | CGTPRKcrASGP | H1K34 | | |
| LKKALAAAGYC | 38 | LKKcrALAAAGYC | H1K64 | LK(me, ac)KALAAAGY(ox)C | H1K63, 71 |
| CKLGLKSLVSK | 39 | CKLGLKcrSLVSK | H1K85 | CK(fo)LGLKSLVSK(me, ac) | H1K81, 90 |
| CKSLVSKGTL | 40 | CKSLVSKcrGTL | H1K90 | | |
| CVQTKGTGA | 41 | CVQTKcrGTGA | H1K97 | | |
| CTPKKAKKPA | 42 | CTPKKAKcrKPA | H1K159 | | |
| VTKKVAKSPKC | 43 | VTKcrKVAKSPKC | H1K168 | | |

Ox: oxidation; pho: phosphorylation; me: methylation; succ: succinylation; pro: propionylation; bu: butyrylation; ac: acety.

---

What is claimed:

1. A method for detecting protein crotonylation in a sample, comprising:
   (a) immunizing a host with an isolated peptide comprising a crotonylated lysine, whereby an affinity reagent that binds specifically to the peptide is produced,
   (b) contacting the sample with the affinity reagent, whereby the affinity reagent binds to a protein or a fragment thereof in the sample, and a binding complex is formed, and
   (c) detecting the binding complex, wherein the presence of the binding complex indicates protein crotonylation in the sample.

2. The method of claim 1, wherein the peptide comprises an amino acid sequence selected from the group consisting of QLATKcrAA (SEQ ID NO: 11), CQLATKcrAA (SEQ ID NO: 12), YQKcrST (SEQ ID NO: 13), CYQKcrSTELL (SEQ ID NO: 14), LLPKKcrTESHHKAK (SEQ ID NO: 15), CLLPKKcrTESHHKAKG (SEQ ID NO: 16), APAPKcrKGS (SEQ ID NO: 17), APAPKcrKGSC (SEQ ID NO: 18), APAPKKcrGS (SEQ ID NO: 17), CAPAPKKcrGS (SEQ ID NO: 19), GSKKcrA (SEQ ID NO: 20), GSKKcrAVTC (SEQ ID NO: 21), TKcrAQKKDG (SEQ ID NO: 22), AVTKcrAQKKDGC (SEQ ID NO: 23), ARTKcrQTAR (SEQ ID NO: 24), ARTKcrQTARC (SEQ ID NO: 25), APRKcrQLA (SEQ ID NO: 26), APRKcrQLATC (SEQ ID NO: 27), QLATKcrAARK (SEQ ID NO: 28), QLATKcrAARKC (SEQ ID NO: 29), AARKcrSAP (SEQ ID NO: 30), AARKcrSAPATGGC (SEQ ID NO: 31), CRLLRKcrGNYAER (SEQ ID NO: 32), CLLPKcrKTESHHKAKG (SEQ ID NO: 16), CLLPKKTESHHKcrAKG (SEQ ID NO: 16), CAVTKAQKcrKDG (SEQ ID NO: 33), CARTKQTARKcrSTG (SEQ ID NO: 34), CSGRGKcrGG (SEQ ID NO: 35), CGLGKGGAKcrRHR (SEQ ID NO: 36), CGTPRKcrASGP (SEQ ID NO: 37), LKKcrALAAAGYC (SEQ ID NO: 38), CKLGLKcrSLVSK (SEQ ID NO: 39), CKSLVSKcrGTL (SEQ ID NO: 40), CVQTKcrGTGA (SEQ ID NO: 41), CTPKKAKcrKPA (SEQ ID NO: 42) and VTKcrKVAKSPKC (SEQ ID NO: 43).

3. The method of claim 1, wherein the peptide consists of an amino acid sequence selected from the group consisting of QLATKcrAA (SEQ ID NO: 11), CQLATKcrAA (SEQ ID NO: 12), YQKcrST (SEQ ID NO: 13), CYQKcrSTELL (SEQ ID NO: 14), LLPKKcrTESHHKAK (SEQ ID NO: 15), CLLPKKcrTESHHKAKG (SEQ ID NO: 16), APAPKcrKGS (SEQ ID NO: 17), APAPKcrKGSC (SEQ ID NO: 18), APAPKKcrGS (SEQ ID NO: 17), CAPAPKKcrGS (SEQ ID NO: 19), GSKKcrA (SEQ ID NO: 20), GSKKcrAVTC (SEQ ID NO: 21), TKcrAQKKDG (SEQ ID NO: 22), AVTKcrAQKKDGC (SEQ ID NO: 23), ARTKcrQTAR (SEQ ID NO: 24), ARTKcrQTARC (SEQ ID NO: 25), APRKcrQLA (SEQ ID NO: 26), APRKcrQLATC (SEQ ID NO: 27), QLATKcrAARK (SEQ ID NO: 28), QLATKcrAARKC (SEQ ID NO: 29), AARKcrSAP (SEQ ID NO: 30), AARKcrSAPATGGC (SEQ ID NO: 31), CRLLRKcrGNYAER (SEQ ID NO: 32), CLLPKcrKTESHHKAKG (SEQ ID NO: 16), CLLPKKTESHHKcrAKG (SEQ ID NO: 16), CAVTKAQKcrKDG (SEQ ID NO: 33), CARTKQTARKcrSTG (SEQ ID NO: 34), CSGRGKcrGG (SEQ ID NO: 35), CGLGKGGAKcrRHR (SEQ ID NO: 36), CGTPRKcrASGP (SEQ ID NO: 37), LKKcrALAAAGYC (SEQ ID NO: 38), CKLGLKcrSLVSK (SEQ ID NO: 39), CKSLVSKcrGTL (SEQ ID NO: 40), CVQTKcrGTGA (SEQ ID NO: 41), CTPKKAKcrKPA (SEQ ID NO: 42) and VTKcrKVAKSPKC (SEQ ID NO: 43).

4. The method of claim 1, wherein the affinity reagent is an antibody, a functional fragment of an antibody, or a fusion peptide containing a functional fragment of an antibody.

5. A method for detecting protein crotonylation in a sample, comprising:
   (a) screening a peptide library using an isolated peptide comprising a crotonylated lysine, whereby an affinity reagent that binds specifically to the peptide is produced,
   (b) contacting the sample with the affinity reagent, whereby the affinity reagent binds to a protein or a fragment thereof in the sample, and a binding complex is formed, and
   (c) detecting the binding complex, wherein the presence of the binding complex indicates protein crotonylation in the sample.

6. The method of claim 5, wherein the peptide comprises an amino acid sequence selected from the group consisting of QLATKcrAA (SEQ ID NO: 11), CQLATKcrAA (SEQ ID NO: 12), YQKcrST (SEQ ID NO: 13), CYQKcrSTELL (SEQ ID NO: 14), LLPKKcrTESHHKAK (SEQ ID NO: 15), CLLPKKcrTESHHKAKG (SEQ ID NO: 16), APAPKcrKGS (SEQ ID NO: 17), APAPKcrKGSC (SEQ ID NO: 18), APAPKKcrGS (SEQ ID NO: 17), CAPAPKKcrGS (SEQ ID NO: 19), GSKKcrA (SEQ ID NO: 20), GSKKcrAVTC (SEQ ID NO: 21), TKcrAQKKDG (SEQ ID NO: 22), AVTKcrAQKKDGC (SEQ ID NO: 23), ARTKcrQTAR (SEQ ID NO: 24), ARTKcrQTARC (SEQ ID NO: 25), APRKcrQLA (SEQ ID NO: 26), APRKcrQLATC (SEQ ID NO: 27), QLATKcrAARK (SEQ ID NO: 28), QLATKcrAARKC (SEQ ID NO: 29), AARKcr- SAP (SEQ ID NO: 30), AARKcrSAPATGGC (SEQ ID NO: 31), CRLLRKcrGNYAER (SEQ ID NO: 32), CLLPKcrKTESHHKAKG (SEQ ID NO: 16), CLLPKKTESHHKcrAKG (SEQ ID NO: 16), CAVTKAQKcrKDG (SEQ ID NO: 33), CARTKQTARKcrSTG (SEQ ID NO: 34), CSGRGKcrGG (SEQ ID NO: 35), CGLGKGGAKcrRHR (SEQ ID NO: 36), CGTPRKcrASGP (SEQ ID NO: 37), LKKcrALAAAGYC (SEQ ID NO: 38),CKLGLKcrSLVSK (SEQ ID NO: 39), CKSLVSKcrGTL (SEQ ID NO: 40), CVQTKcrGTGA (SEQ ID NO: 41), CTPKKAKcrKPA (SEQ ID NO: 42) and VTKcrKVAKSPKC (SEQ ID NO: 43).

7. The method of claim 5, wherein the peptide consists of an amino acid sequence selected from the group consisting of QLATKcrAA (SEQ ID NO: 11), CQLATKcrAA (SEQ ID NO: 12), YQKcrST (SEQ ID NO: 13), CYQKcrSTELL (SEQ ID NO: 14), LLPKKcrTESHHKAK (SEQ ID NO: 15), CLLPKKcrTESHHKAKG (SEQ ID NO: 16), APAPKcrKGS (SEQ ID NO: 17), APAPKcrKGSC (SEQ ID NO: 18), APAPKKcrGS (SEQ ID NO: 17), CAPAPKKcrGS (SEQ ID NO: 19), GSKKcrA (SEQ ID NO: 20), GSKKcrAVTC (SEQ ID NO: 21), TKcrAQKKDG (SEQ ID NO: 22), AVTKcrAQKKDGC (SEQ ID NO: 23), ARTKcrQTAR (SEQ ID NO: 24), ARTKcrQTARC (SEQ ID NO: 25), APRKcrQLA (SEQ ID NO: 26), APRKcrQLATC (SEQ ID NO: 27), QLATKcrAARK (SEQ ID NO: 28), QLATKcrAARKC (SEQ ID NO: 29), AARKcrSAP (SEQ ID NO: 30), AARKcrSAPATGGC (SEQ ID NO: 31), CRLLRKcrGNYAER (SEQ ID NO: 32), CLLPKcrKTESHHKAKG (SEQ ID NO: 16), CLLPKKTESHHKcrAKG (SEQ ID NO: 16), CAVTKAQKcrKDG (SEQ ID NO: 33), CARTKQTARKcrSTG (SEQ ID NO: 34), CSGRGKcrGG (SEQ ID NO: 35), CGLGKGGAKcrRHR (SEQ ID NO: 36), CGTPRKcrASGP (SEQ ID NO: 37), LKKcrALAAAGYC (SEQ ID NO: 38), CKLGLKcrSLVSK (SEQ ID NO: 39), CKSLVSKcrGTL (SEQ ID NO: 40), CVQTKcrGTGA (SEQ ID NO: 41), CTPKKAKcrKPA (SEQ ID NO: 42) and VTKcrKVAKSPKC (SEQ ID NO: 43).

8. The method of claim 5, wherein the affinity reagent is an antibody, a functional fragment of an anitbody, or a fusion peptide containing a functional fragment of an antibody.

9. The method of claim 5, wherein the peptide library is a phage display library or a yeast display library.

* * * * *

SEQUENCE LISTING

<160> NUMBER OF SEQ ID NOS: 47

<210> SEQ ID NO 1
<211> LENGTH: 213
<212> TYPE: PRT
<213> ORGANISM: Homo sapiens

<400> SEQUENCE: 1

```
Met Ser Glu Thr Ala Pro Ala Ala Pro Ala Ala Pro Ala Pro Ala Glu
1               5                   10                  15

Lys Ala Pro Val Lys Lys Lys Ala Ala Lys Lys Ala Gly Gly Thr Pro
                20                  25                  30

Arg Lys Ala Ser Gly Pro Pro Val Ser Glu Leu Ile Thr Lys Ala Val
            35                  40                  45

Ala Ala Ser Lys Glu Arg Ser Gly Val Ser Leu Ala Ala Leu Lys Lys
50                  55                  60

Ala Leu Ala Ala Ala Gly Tyr Asp Val Glu Lys Asn Asn Ser Arg Ile
65                  70                  75                  80

Lys Leu Gly Leu Lys Ser Leu Val Ser Lys Gly Thr Leu Val Gln Thr
                85                  90                  95

Lys Gly Thr Gly Ala Ser Gly Ser Phe Lys Leu Asn Lys Lys Ala Ala
            100                 105                 110

Ser Gly Glu Ala Lys Pro Lys Val Lys Lys Ala Gly Gly Thr Lys Pro
        115                 120                 125

Lys Lys Pro Val Gly Ala Ala Lys Lys Pro Lys Lys Ala Ala Gly Gly
130                 135                 140

Ala Thr Pro Lys Lys Ser Ala Lys Lys Thr Pro Lys Lys Ala Lys Lys
145                 150                 155                 160

Pro Ala Ala Ala Thr Val Thr Lys Lys Val Ala Lys Ser Pro Lys Lys
                165                 170                 175

Ala Lys Val Ala Lys Pro Lys Lys Ala Ala Lys Ser Ala Ala Lys Ala
            180                 185                 190

Val Lys Pro Lys Ala Ala Lys Pro Lys Val Val Lys Pro Lys Lys Ala
        195                 200                 205

Ala Pro Lys Lys Lys
    210
```

<210> SEQ ID NO 2
<211> LENGTH: 130
<212> TYPE: PRT
<213> ORGANISM: Homo sapiens

<400> SEQUENCE: 2

Met Ser Gly Arg Gly Lys Gln Gly Gly Lys Ala Arg Ala Lys Ala Lys
1               5                   10                  15

Thr Arg Ser Ser Arg Ala Gly Leu Gln Phe Pro Val Gly Arg Val His
            20                  25                  30

Arg Leu Leu Arg Lys Gly Asn Tyr Ser Glu Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
65                  70                  75                  80

Pro Arg His Leu Gln Leu Ala Ile Arg Asn Asp Glu Glu Leu Asn Lys
                85                  90                  95

Leu Leu Gly Arg Val Thr Ile Ala Gln Gly Gly Val Leu Pro Asn Ile
            100                 105                 110

Gln Ala Val Leu Leu Pro Lys Lys Thr Glu Ser His His Lys Ala Lys
        115                 120                 125

Gly Lys
    130

<210> SEQ ID NO 3
<211> LENGTH: 126
<212> TYPE: PRT
<213> ORGANISM: Homo sapiens

<400> SEQUENCE: 3

Met Pro Glu Pro Ser Lys Ser Ala Pro Ala Pro Lys Lys Gly Ser Lys
1               5                   10                  15

Lys Ala Ile Thr Lys Ala Gln Lys Lys Asp Gly Lys Lys Arg Lys Arg
            20                  25                  30

Ser Arg Lys Glu Ser Tyr Ser Ile Tyr Val Tyr Lys Val Leu Lys Gln
        35                  40                  45

Val His Pro Asp Thr Gly Ile Ser Ser Lys Ala Met Gly Ile Met Asn
    50                  55                  60

Ser Phe Val Asn Asp Ile Phe Glu Arg Ile Ala Gly Glu Ala Ser Arg
65                  70                  75                  80

Leu Ala His Tyr Asn Lys Arg Ser Thr Ile Thr Ser Arg Glu Ile Gln
                85                  90                  95

Thr Ala Val Arg Leu Leu Leu Pro Gly Glu Leu Ala Lys His Ala Val
            100                 105                 110

Ser Glu Gly Thr Lys Ala Val Thr Lys Tyr Thr Ser Ser Lys
        115                 120                 125

<210> SEQ ID NO 4
<211> LENGTH: 136
<212> TYPE: PRT
<213> ORGANISM: Homo sapiens

<400> SEQUENCE: 4

Met Ala Arg Thr Lys Gln Thr Ala Arg Lys Ser Thr Gly Gly Lys Ala
1               5                   10                  15

-continued

```
Pro Arg Lys Gln Leu Ala Thr Lys Ala Ala Arg Lys Ser Ala Pro Ser
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ala Ala Ile Gly Ala Leu Gln Glu Ala
                85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 5
<211> LENGTH: 103
<212> TYPE: PRT
<213> ORGANISM: Homo sapiens

<400> SEQUENCE: 5

Met Ser Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys
            20                  25                  30

Pro Ala Ile Arg Arg Leu Ala Arg Arg Gly Gly Val Lys Arg Ile Ser
        35                  40                  45

Gly Leu Ile Tyr Glu Glu Thr Arg Gly Val Leu Lys Val Phe Leu Glu
    50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100

<210> SEQ ID NO 6
<211> LENGTH: 212
<212> TYPE: PRT
<213> ORGANISM: Mus musculus

<400> SEQUENCE: 6

Met Ser Glu Ala Ala Pro Ala Ala Pro Ala Ala Pro Pro Ala Glu
1               5                   10                  15

Lys Ala Pro Ala Lys Lys Lys Ala Ala Lys Lys Pro Ala Gly Val Arg
            20                  25                  30

Arg Lys Ala Ser Gly Pro Pro Val Ser Glu Leu Ile Thr Lys Ala Val
        35                  40                  45

Ala Ala Ser Lys Glu Arg Ser Gly Val Ser Leu Ala Ala Leu Lys Lys
    50                  55                  60

Ala Leu Ala Ala Ala Gly Tyr Asp Val Glu Lys Asn Asn Ser Arg Ile
65                  70                  75                  80

Lys Leu Gly Leu Lys Ser Leu Val Ser Lys Gly Ile Leu Val Gln Thr
                85                  90                  95
```

```
Lys Gly Thr Gly Ala Ser Gly Ser Phe Lys Leu Asn Lys Ala Ala
            100                 105                 110

Ser Gly Glu Ala Lys Pro Gln Ala Lys Lys Ala Gly Ala Ala Lys Ala
        115                 120                 125

Lys Lys Pro Ala Gly Ala Ala Lys Lys Pro Lys Lys Ala Thr Gly Ala
    130                 135                 140

Ala Thr Pro Lys Lys Ala Ala Lys Lys Thr Pro Lys Lys Ala Lys Lys
145                 150                 155                 160

Pro Ala Ala Ala Ala Val Thr Lys Lys Val Ala Lys Ser Pro Lys Lys
                165                 170                 175

Ala Lys Val Thr Lys Pro Lys Lys Val Lys Ser Ala Ser Lys Ala Val
            180                 185                 190

Lys Pro Lys Ala Ala Lys Pro Lys Val Ala Lys Ala Lys Lys Val Ala
        195                 200                 205

Ala Lys Lys Lys
    210
```

<210> SEQ ID NO 7
<211> LENGTH: 130
<212> TYPE: PRT
<213> ORGANISM: Mus musculus

<400> SEQUENCE: 7

```
Met Ser Gly Arg Gly Lys Gln Gly Gly Lys Ala Arg Ala Lys Ala Lys
1               5                   10                  15

Thr Arg Ser Ser Arg Ala Gly Leu Gln Phe Pro Val Gly Arg Val His
            20                  25                  30

Arg Leu Leu Arg Lys Gly Asn Tyr Ser Glu Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
65                  70                  75                  80

Pro Arg His Leu Gln Leu Ala Ile Arg Asn Asp Glu Glu Leu Asn Lys
                85                  90                  95

Leu Leu Gly Arg Val Thr Ile Ala Gln Gly Gly Val Leu Pro Asn Ile
            100                 105                 110

Gln Ala Val Leu Leu Pro Lys Lys Thr Glu Ser His His Lys Ala Lys
        115                 120                 125

Gly Lys
    130
```

<210> SEQ ID NO 8
<211> LENGTH: 126
<212> TYPE: PRT
<213> ORGANISM: Mus musculus

<400> SEQUENCE: 8

```
Met Pro Glu Pro Ser Lys Ser Ala Pro Ala Pro Lys Lys Gly Ser Lys
1               5                   10                  15

Lys Ala Ile Ser Lys Ala Gln Lys Lys Asp Gly Lys Lys Arg Lys Arg
            20                  25                  30

Ser Arg Lys Glu Ser Tyr Ser Val Tyr Val Tyr Lys Val Leu Lys Gln
        35                  40                  45

Val His Pro Asp Thr Gly Ile Ser Ser Lys Ala Met Gly Ile Met Asn
    50                  55                  60
```

-continued

Ser Phe Val Asn Asp Ile Phe Glu Arg Ile Ala Ser Glu Ala Ser Arg
 65                  70                  75                  80

Leu Ala His Tyr Asn Lys Arg Ser Thr Ile Thr Ser Arg Glu Ile Gln
                 85                  90                  95

Thr Ala Val Arg Leu Leu Leu Pro Gly Glu Leu Ala Lys His Ala Val
            100                 105                 110

Ser Glu Gly Thr Lys Ala Val Thr Lys Tyr Thr Ser Ser Lys
        115                 120                 125

<210> SEQ ID NO 9
<211> LENGTH: 136
<212> TYPE: PRT
<213> ORGANISM: Mus musculus

<400> SEQUENCE: 9

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ser
                20                  25                  30

Thr Gly Gly Val Lys Lys Pro His Arg Tyr Arg Pro Gly Thr Val Ala
            35                  40                  45

Leu Arg Glu Ile Arg Arg Tyr Gln Lys Ser Thr Glu Leu Leu Ile Arg
        50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ala Ala Ile Gly Ala Leu Gln Glu Ala
                85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 10
<211> LENGTH: 103
<212> TYPE: PRT
<213> ORGANISM: Mus musculus

<400> SEQUENCE: 10

Met Ser Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys
                20                  25                  30

Pro Ala Ile Arg Arg Leu Ala Arg Arg Gly Gly Val Lys Arg Ile Ser
            35                  40                  45

Gly Leu Ile Tyr Glu Glu Thr Arg Gly Val Leu Lys Val Phe Leu Glu
        50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100

<210> SEQ ID NO 11
<211> LENGTH: 7

<212> TYPE: PRT
<213> ORGANISM: Artificial Sequence
<220> FEATURE:
<223> OTHER INFORMATION: Synthetic

<400> SEQUENCE: 11

Gln Leu Ala Thr Lys Ala Ala
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic

<400> SEQUENCE: 12

Cys Gln Leu Ala Thr Lys Ala Ala
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic

<400> SEQUENCE: 13

Tyr Gln Lys Ser Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic

<400> SEQUENCE: 14

Cys Tyr Gln Lys Ser Thr Glu Leu Leu
1               5

<210> SEQ ID NO 15
<211> LENGTH: 13
<212> TYPE: PRT
<213> ORGANISM: Artificial Sequence
<220> FEATURE:
<223> OTHER INFORMATION: Synthetic

<400> SEQUENCE: 15

Leu Leu Pro Lys Lys Thr Glu Ser His His Lys Ala Lys
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Synthetic

<400> SEQUENCE: 16

Cys Leu Leu Pro Lys Lys Thr Glu Ser His His Lys Ala Lys Gly
1               5                   10                  15

<210> SEQ ID NO 17
<211> LENGTH: 8
<212> TYPE: PRT

```
<213> ORGANISM: Artificial Sequence
<220> FEATURE:
<223> OTHER INFORMATION: Synthetic

<400> SEQUENCE: 17

Ala Pro Ala Pro Lys Lys Gly Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Ala Pro Ala Pro Lys Lys Gly Ser Cys
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic

<400> SEQUENCE: 19

Cys Ala Pro Ala Pro Lys Lys Gly Ser
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic

<400> SEQUENCE: 20

Gly Ser Lys Lys Ala
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic

<400> SEQUENCE: 21

Gly Ser Lys Lys Ala Val Thr Cys
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Thr Lys Ala Gln Lys Lys Asp Gly
1               5

<210> SEQ ID NO 23
<211> LENGTH: 11
<212> TYPE: PRT
<213> ORGANISM: Artificial Sequence
```

```
<220> FEATURE:
<223> OTHER INFORMATION: Synthetic

<400> SEQUENCE: 23

Ala Val Thr Lys Ala Gln Lys Lys Asp Gly Cys
1               5                   10

<210> SEQ ID NO 24
<211> LENGTH: 8
<212> TYPE: PRT
<213> ORGANISM: Artificial Sequence
<220> FEATURE:
<223> OTHER INFORMATION: Synthetic

<400> SEQUENCE: 24

Ala Arg Thr Lys Gln Thr Ala Arg
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic

<400> SEQUENCE: 25

Ala Arg Thr Lys Gln Thr Ala Arg Cys
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic

<400> SEQUENCE: 26

Ala Pro Arg Lys Gln Leu Ala
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic

<400> SEQUENCE: 27

Ala Pro Arg Lys Gln Leu Ala Thr Cys
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic

<400> SEQUENCE: 28

Gln Leu Ala Thr Lys Ala Ala Arg Lys
1               5

<210> SEQ ID NO 29
<211> LENGTH: 10
<212> TYPE: PRT
<213> ORGANISM: Artificial Sequence
<220> FEATURE:
```

<223> OTHER INFORMATION: Synthetic

<400> SEQUENCE: 29

Gln Leu Ala Thr Lys Ala Ala Arg Lys Cys
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Synthetic

<400> SEQUENCE: 30

Ala Ala Arg Lys Ser Ala Pro
1               5

<210> SEQ ID NO 31
<211> LENGTH: 21
<212> TYPE: PRT
<213> ORGANISM: Artificial Sequence
<220> FEATURE:
<223> OTHER INFORMATION: Synthetic

<400> SEQUENCE: 31

Ser Tyr Asn Thr His Glu Thr Ile Cys Ala Ala Arg Lys Ser Ala Pro
1               5                   10                  15

Ala Thr Gly Gly Cys
            20

<210> SEQ ID NO 32
<211> LENGTH: 12
<212> TYPE: PRT
<213> ORGANISM: Artificial Sequence
<220> FEATURE:
<223> OTHER INFORMATION: Synthetic

<400> SEQUENCE: 32

Cys Arg Leu Leu Arg Lys Gly Asn Tyr Ala Glu Arg
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Synthetic

<400> SEQUENCE: 33

Cys Ala Val Thr Lys Ala Gln Lys Lys Asp Gly
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Synthetic

<400> SEQUENCE: 34

Cys Ala Arg Thr Lys Gln Thr Ala Arg Lys Ser Thr Gly
1               5                   10

<210> SEQ ID NO 35
<211> LENGTH: 8
<212> TYPE: PRT

```
<213> ORGANISM: Artificial Sequence
<220> FEATURE:
<223> OTHER INFORMATION: Synthetic

<400> SEQUENCE: 35

Cys Ser Gly Arg Gly Lys Gly Gly
1               5

<210> SEQ ID NO 36
<211> LENGTH: 12
<212> TYPE: PRT
<213> ORGANISM: Artificial Sequence
<220> FEATURE:
<223> OTHER INFORMATION: Synthetic

<400> SEQUENCE: 36

Cys Gly Leu Gly Lys Gly Gly Ala Lys Arg His Arg
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Synthetic

<400> SEQUENCE: 37

Cys Gly Thr Pro Arg Lys Ala Ser Gly Pro
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Synthetic

<400> SEQUENCE: 38

Leu Lys Lys Ala Leu Ala Ala Ala Gly Tyr Cys
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Synthetic

<400> SEQUENCE: 39

Cys Lys Leu Gly Leu Lys Ser Leu Val Ser Lys
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthetic

<400> SEQUENCE: 40

Cys Lys Ser Leu Val Ser Lys Gly Thr Leu
1               5                   10

<210> SEQ ID NO 41
<211> LENGTH: 9
<212> TYPE: PRT
<213> ORGANISM: Artificial Sequence
```

<220> FEATURE:
<223> OTHER INFORMATION: Synthetic

<400> SEQUENCE: 41

Cys Val Gln Thr Lys Gly Thr Gly Ala
1               5

<210> SEQ ID NO 42
<211> LENGTH: 10
<212> TYPE: PRT
<213> ORGANISM: Artificial Sequence
<220> FEATURE:
<223> OTHER INFORMATION: Synthetic

<400> SEQUENCE: 42

Cys Thr Pro Lys Lys Ala Lys Lys Pro Ala
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Synthetic

<400> SEQUENCE: 43

Val Thr Lys Lys Val Ala Lys Ser Pro Lys Cys
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Synthetic

<400> SEQUENCE: 44

Pro Glu Pro Ala Lys Cys Arg Ser Ala Pro Ala Pro Lys
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: X
<222> LOCATION: (2)..(6)
<223> OTHER INFORMATION: X may be any naturally occuring amino acid
      except cysteine
<220> FEATURE:
<221> NAME/KEY: X
<222> LOCATION: (8)..(13)
<223> OTHER INFORMATION: X may be any naturally occuring amino acid
      except cysteine

<400> SEQUENCE: 45

Cys Xaa Xaa Xaa Xaa Xaa Lys Xaa Xaa Xaa Xaa Xaa Xaa
1               5                   10

<210> SEQ ID NO 46
<211> LENGTH: 8
<212> TYPE: PRT
<213> ORGANISM: Artificial Sequence
<220> FEATURE:
<223> OTHER INFORMATION: Synthetic

<400> SEQUENCE: 46

```
Cys Arg Ser Arg Lys Glu Ser Tyr
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic

<400> SEQUENCE: 47

Gly Gly Lys Gly Leu Gly Lys Cys
1               5
```